(12) United States Patent
Bethune et al.

(10) Patent No.: US 12,071,438 B2
(45) Date of Patent: Aug. 27, 2024

(54) CRYSTAL FORMS OF AN ALK2 INHIBITOR

(71) Applicant: Keros Therapeutics, Inc., Lexington, MA (US)

(72) Inventors: Sarah Bethune, Longmont, CO (US); Krista Diaz, Longmont, CO (US); Catherine A. Evans, Somerville, MA (US)

(73) Assignee: Keros Therapeutics, Inc., Lexington, MA (US)

( * ) Notice: Subject to any disclaimer, the term of this patent is extended or adjusted under 35 U.S.C. 154(b) by 680 days.

(21) Appl. No.: 17/238,986

(22) Filed: Apr. 23, 2021

(65) Prior Publication Data

US 2021/0238185 A1 Aug. 5, 2021

Related U.S. Application Data

(63) Continuation of application No. PCT/US2019/058062, filed on Oct. 25, 2019.

(60) Provisional application No. 62/751,255, filed on Oct. 26, 2018.

(51) Int. Cl.
| | | |
|---|---|---|
| C07C 55/10 | (2006.01) | |
| A61P 19/02 | (2006.01) | |
| A61P 19/08 | (2006.01) | |
| A61P 35/00 | (2006.01) | |
| A61P 35/04 | (2006.01) | |
| A61P 37/00 | (2006.01) | |
| A61P 43/00 | (2006.01) | |
| C07D 487/04 | (2006.01) | |

(52) U.S. Cl.
CPC ........ C07D 487/04 (2013.01); C07B 2200/13 (2013.01)

(58) Field of Classification Search
CPC ... C07D 487/04; C07B 2200/13; C07C 55/10; A61P 19/02; A61P 19/08; A61P 35/04; A61P 37/00; A61P 43/00; A61P 35/00
See application file for complete search history.

(56) References Cited

U.S. PATENT DOCUMENTS

| | | |
|---|---|---|
| 8,507,501 B2 | 8/2013 | Yu et al. |
| 9,045,484 B2 | 6/2015 | Yu et al. |
| 9,682,983 B2 | 6/2017 | Alimardanov et al. |
| 10,017,516 B2 | 7/2018 | Alimardanov et al. |
| 10,233,186 B2 | 3/2019 | Brooijmans et al. |
| 10,513,521 B2 | 12/2019 | Lee et al. |
| 10,669,277 B2 | 6/2020 | Wilson et al. |
| 11,026,947 B2 | 6/2021 | Yu et al. |
| 11,654,147 B2 | 5/2023 | Yu et al. |
| 2012/0030780 A1 | 2/2012 | Ma |
| 2016/0115167 A1 | 4/2016 | Yu et al. |
| 2017/0183411 A1 | 6/2017 | Lin et al. |
| 2018/0057586 A1 | 3/2018 | Westerman et al. |
| 2018/0171005 A1 | 6/2018 | Cong et al. |
| 2019/0055192 A1 | 2/2019 | Dalton et al. |
| 2020/0095251 A1 | 3/2020 | Vechorkin et al. |
| 2020/0179389 A1 | 6/2020 | Yu et al. |
| 2020/0331908 A1 | 10/2020 | Brubaker et al. |
| 2021/0154195 A1 | 5/2021 | Chen et al. |
| 2021/0253720 A1 | 8/2021 | Seehra et al. |
| 2022/0401445 A1 | 12/2022 | Seehra et al. |
| 2023/0372390 A1 | 11/2023 | Seehra et al. |
| 2023/0398118 A1 | 12/2023 | Seehra et al. |
| 2023/0406956 A1 | 12/2023 | Seehra et al. |

FOREIGN PATENT DOCUMENTS

| | | |
|---|---|---|
| WO | WO-2006/052913 A1 | 5/2006 |
| WO | WO-2009/114180 A1 | 9/2009 |
| WO | WO-2012/064805 A1 | 5/2012 |
| WO | WO-2014/160203 A2 | 10/2014 |
| WO | WO-2018/200855 A1 | 11/2018 |
| WO | WO-2018/232094 A1 | 12/2018 |
| WO | WO-2019/102256 A1 | 5/2019 |
| WO | WO-2020/068729 A1 | 4/2020 |
| WO | WO-2020/086963 A1 | 4/2020 |
| WO | WO-2021/030386 A1 | 2/2021 |
| WO | WO-2021/067670 A1 | 4/2021 |
| WO | WO-2023/081212 A1 | 5/2023 |

OTHER PUBLICATIONS

Berge, M., "Pharmaceutical Salts" Journal of Pharmaceutical Sciences 1977 66:1-19.*
Stieger, N., "Recrystallization of active pharmaceutical ingredients." Crystallization-Science and Technology [Internet]. InTech (2012): 183-201.*
Saal, C., "Pharmaceutical salts: A summary on doses of salt formers from the Orange Book." European Journal of Pharmaceutical Sciences 49.4 (2013): 614-623.*
International Search Report and Written Opinion for Patent Application No. PCT/US2019/058062, mailed Dec. 24, 2019 (4 pages).
Ensan et al., "Targeting ALK2: An Open Science Approach to Developing Therapeutics for the Treatment of Diffuse Intrinsic Pontine Glioma," J Med Chem. 63(9):4978-4996 (2020).
Morrell et al., "Targeting BMP signalling in cardiovascular disease and anaemia," Nat Rev Cardiol. 13(2):106-20 (2016).
Saeed et al., "Remnant-Like Particle Cholesterol, Low-Density Lipoprotein Triglycerides, and Incident Cardiovascular Disease," J Am Coll Cardiol. 72(2):156-169 (Jul. 2018).
Ali et al., "Bone morphogenetic proteins and their antagonists: current and emerging clinical uses," Br J Pharmacol. 171(15):3620-32 (2014).
Vela, Driton, "Balance of cardiac and systemic hepcidin and its role in heart physiology and pathology," Lab Invest. 98(3):315-326 (Mar. 2018).

(Continued)

*Primary Examiner* — John M Mauro
(74) *Attorney, Agent, or Firm* — Clark & Elbing LLP

(57) ABSTRACT

The invention relates to crystalline forms of an ALK2 inhibitor, methods of their preparation, and related pharmaceutical preparations thereof. The invention also relates to pharmaceutical uses of the crystalline forms.

17 Claims, 26 Drawing Sheets

(56) References Cited

OTHER PUBLICATIONS

Asshoff et al., "Momelotinib inhibits ACVR1/ALK2, decreases hepcidin production, and ameliorates anemia of chronic disease in rodents," Blood. 129(13):1823-1830 (2017).
Abdelmahmuod et al., "Iron Deficiency Anemia-Induced Lymphocytopenia in a Young Female," Case Rep Oncol. 13(2):793-797 (2020).
Barton et al., "Iron overload and prolonged ingestion of iron supplements: clinical features and mutation analysis of hemochromatosis-associated genes in four cases," Am J Hematol. 81(10):760-7 (2006).
"Sideroblastic anemia," Wikipedia, <https://en.wikipedia.org/w/index.php?title=Sideroblastic_anemia&oldid=1056240400>, retrieved May 12, 2023 (Nov. 20, 2021) (6 pages).

* cited by examiner

CRYSTAL FORMS OF AN ALK2 INHIBITOR

BACKGROUND

The BMP signaling family is a diverse subset of the TGF-β superfamily. Over twenty known BMP ligands are recognized by three distinct type II (BMPRII, ActRIIa, and ActRIIb) and at least four type I (ALK1, ALK2, ALK3, and ALK6) receptors. Dimeric ligands facilitate assembly of receptor heteromers, allowing the constitutively-active type II receptor serine/threonine kinases to phosphorylate type I receptor serine/threonine kinases. Activated type I receptors phosphorylate BMP-responsive (BR-) SMAD effectors (SMADs 1, 5, and 8) to facilitate nuclear translocation in complex with SMAD4, a co-SMAD that also facilitates TGF signaling. In addition, BMP signals can activate intracellular effectors such as MAPK p38 in a SMAD-independent manner. Soluble BMP inhibitors, such as noggin, chordin, gremlin, and follistatin, limit BMP signaling by ligand sequestration.

A role for BMP signals in regulating expression of hepcidin, a peptide hormone and central regulator of systemic iron balance, has also been suggested. Hepcidin binds and promotes degradation of ferroportin, the sole iron exporter in vertebrates. Loss of ferroportin activity prevents mobilization of iron to the bloodstream from intracellular stores in enterocytes, macrophages, and hepatocytes. The link between BMP signaling and iron metabolism represents a potential target for therapeutics.

Given the tremendous structural diversity of the BMP and TGF-β superfamily at the level of ligands (>25 distinct ligands at present) and receptors (four type I and three type II receptors that recognize BMPs), and the heterotetrameric manner of receptor binding, traditional approaches for inhibiting BMP signals via soluble receptors, endogenous inhibitors, or neutralizing antibodies are not practical or effective. Endogenous inhibitors such as noggin and follistatin have limited specificity for ligand subclasses. Single receptors have limited affinity for ligand, whereas receptors heterotetramers exhibit more specificity for particular ligands. Neutralizing antibodies which are specific for particular ligands or receptors have been previously described, and are also limited by the structural diversity of this signaling system. Thus, there is a need in the art for pharmacologic agents that specifically antagonize BMP signaling pathways and that can be used to manipulate these pathways in therapeutic or experimental applications, such as those listed above.

SUMMARY OF INVENTION

One aspect of the invention relates to crystalline compounds having the structure of Formula (I),

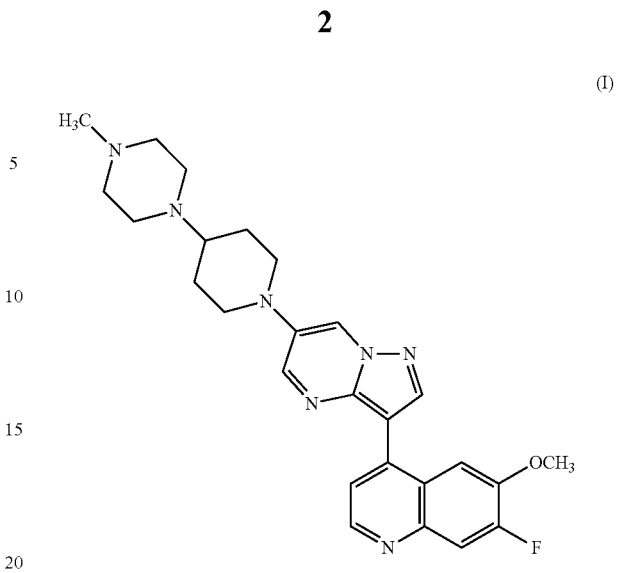

and salts thereof.

Another aspect of the invention relates to methods for preparing the crystalline compounds of Formula (I).

In certain embodiments, the present invention provides a pharmaceutical preparation suitable for use in a subject, comprising a crystalline compound of Formula (I), and one or more pharmaceutically acceptable excipients. In certain embodiments, the pharmaceutical preparations may be for use in treating or preventing a condition or disease as described herein.

DETAILED DESCRIPTION OF THE DRAWINGS

DETAILED DESCRIPTION OF THE INVENTION

In certain embodiments, the invention provides crystalline compounds having the structure of Formula (I),

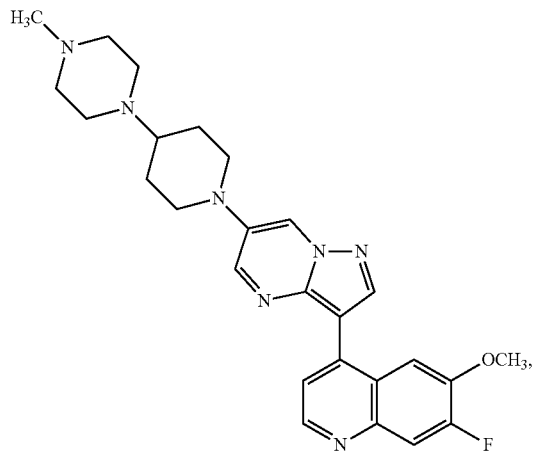

(I)

and salts thereof.

In certain embodiments, a crystalline compound of Formula (I) is not solvated (e.g., the crystal lattice does not comprise molecules of a solvent). In certain such embodiments, the crystalline compound of Formula (I) is anhydrous, or substantially anhydrous.

In certain embodiments, the compound of Formula (I) is in the form of a salt with an anion selected from chloride, bromide, succinate, xinafoate, citrate, malate, hemi-malate, tartrate, malonate, mesylate, phosphate, tosylate, sulfate, and bis-sulfate. In preferred embodiments, the compound of Formula (I) is in the form of a succinate salt, such as a mono-succinate salt.

Any crystalline compound described herein may be used in the manufacture of a medicament for the treatment of any diseases or conditions disclosed herein.

The mono-succinate salt of the compound of Formula (I) exists at least as "Form A," "Form B," "Form C," and "Form D," as described in detail below. These different forms are understood as "polymorphs" herein.

A polymorph of the crystalline compound may be characterized by powder X-ray diffraction (XRPD). θ represents the diffraction angle, measured in degrees. In certain embodiments, the diffractometer used in XRPD measures the diffraction angle as two times the diffraction angle θ. Thus, in certain embodiments, the diffraction patterns described herein refer to X-ray intensity measured against angle 2θ.

In certain embodiments, a first anhydrous crystalline form of a compound of Formula (I) mono-succinate salt has 2θ values of about 7.05±0.2, 15.16±0.2, 21.05±0.2, 21.26±0.2, and 24.47±0.2. In further embodiments, an anhydrous crystalline compound of Formula (I) mono-succinate salt has 2θ values of about 3.58±0.2, 7.05±0.2, 13.8±0.2, 14.16±0.2, 15.16±0.2, 16.18±0.2, 16.80±0.2, 17.15±0.2, 17.69±0.2, 18.29±0.2, 18.84±0.2, 20.29±0.2, 21.05±0.2, 21.26±0.2, 22.68±0.2, 23.84±0.2, 24.47±0.2, 24.84±0.2, and 28.47±0.2. In yet further embodiments, the anhydrous crystalline compound of Formula (I) mono-succinate salt has 2θ values of about 3.58±0.2, 7.05±0.2, 10.59±0.2, 10.75±0.2, 13.80±0.2, 14.16±0.2, 15.16±0.2, 15.68±0.2, 16.18±0.2, 16.80±0.2, 17.15±0.2, 17.69±0.2, 17.97±0.2, 18.29±0.2, 18.59±0.2, 18.84±0.2, 19.27±0.2, 20.29±0.2, 21.05±0.2, 21.26±0.2, 21.56±0.2, 21.78±0.2, 22.68±0.2, 23.84±0.2, 24.47±0.2, 24.84±0.2, 25.15±0.2, 26.10±0.2, 27.12±0.2, 27.78±0.2, 28.47±0.2, and 29.06±0.2.

Figure 1:
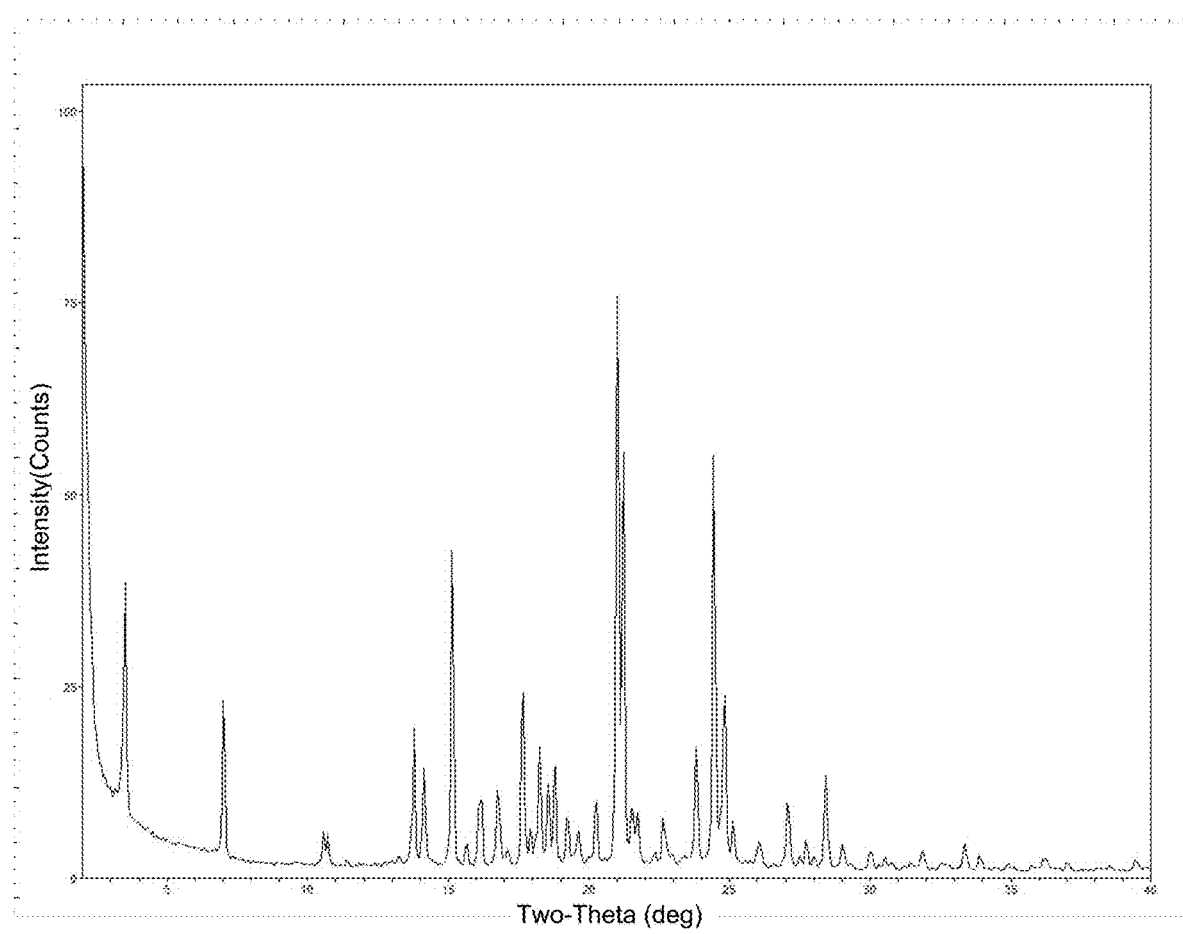
FIG. 1 shows the XRPD pattern of the compound of Formula (I) mono-succinate salt Form A.

In certain embodiments, an anhydrous crystalline form of a compound of Formula (I) mono-succinate salt has an XRPD pattern substantially as shown in FIG. 1, labeled Form A.

In certain embodiments, a second anhydrous crystalline form of a compound of Formula (I) mono-succinate salt has 2θ values of about 9.79±0.2, 13.05±0.2, 22.91±0.2, 23.60±0.2, and 26.25±0.2. In further embodiments, an anhydrous crystalline compound of Formula (I) mono-succinate salt has 2θ values of about 3.25±0.2, 9.79±0.2, 13.05±0.2, 16.75±0.2, 19.50±0.2, 22.91±0.2, 23.60±0.2, and 26.25±0.2. In yet further embodiments, an anhydrous crystalline compound of Formula (I) mono-succinate salt has 2θ values of about 3.25±0.2, 9.79±0.2, 13.05±0.2, 13.61±0.2, 14.39±0.2, 16.75±0.2, 18.50±0.2, 19.50±0.2, 22.91±0.2, 23.60±0.2, and 26.25±0.2.

Figure 2:
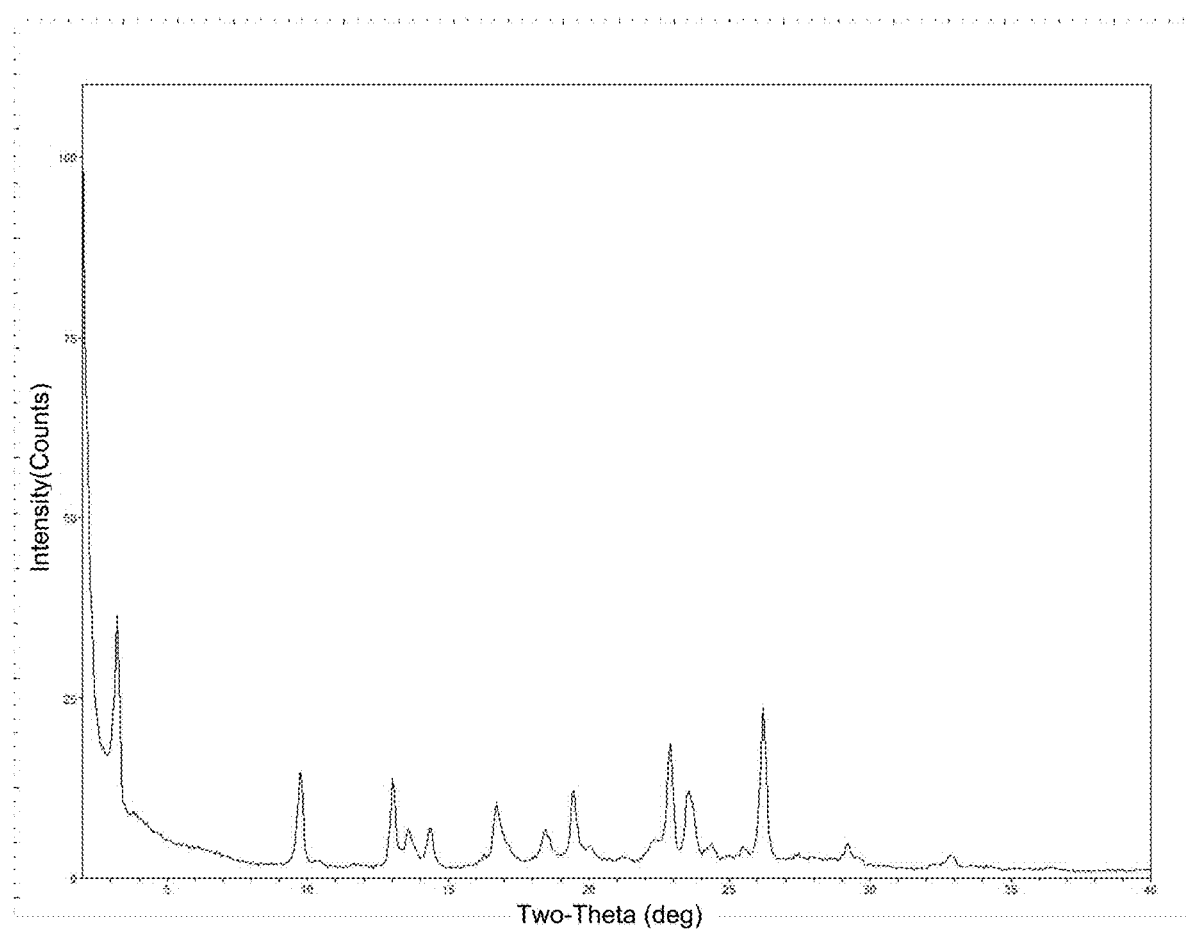
FIG. 2 shows the XRPD pattern of the compound of Formula (I) mono-succinate salt Form B.

The certain embodiments, an anhydrous crystalline form of a compound of Formula (I) mono-succinate salt has an XRPD pattern substantially as shown in FIG. 2, labeled Form B.

Figure 3:
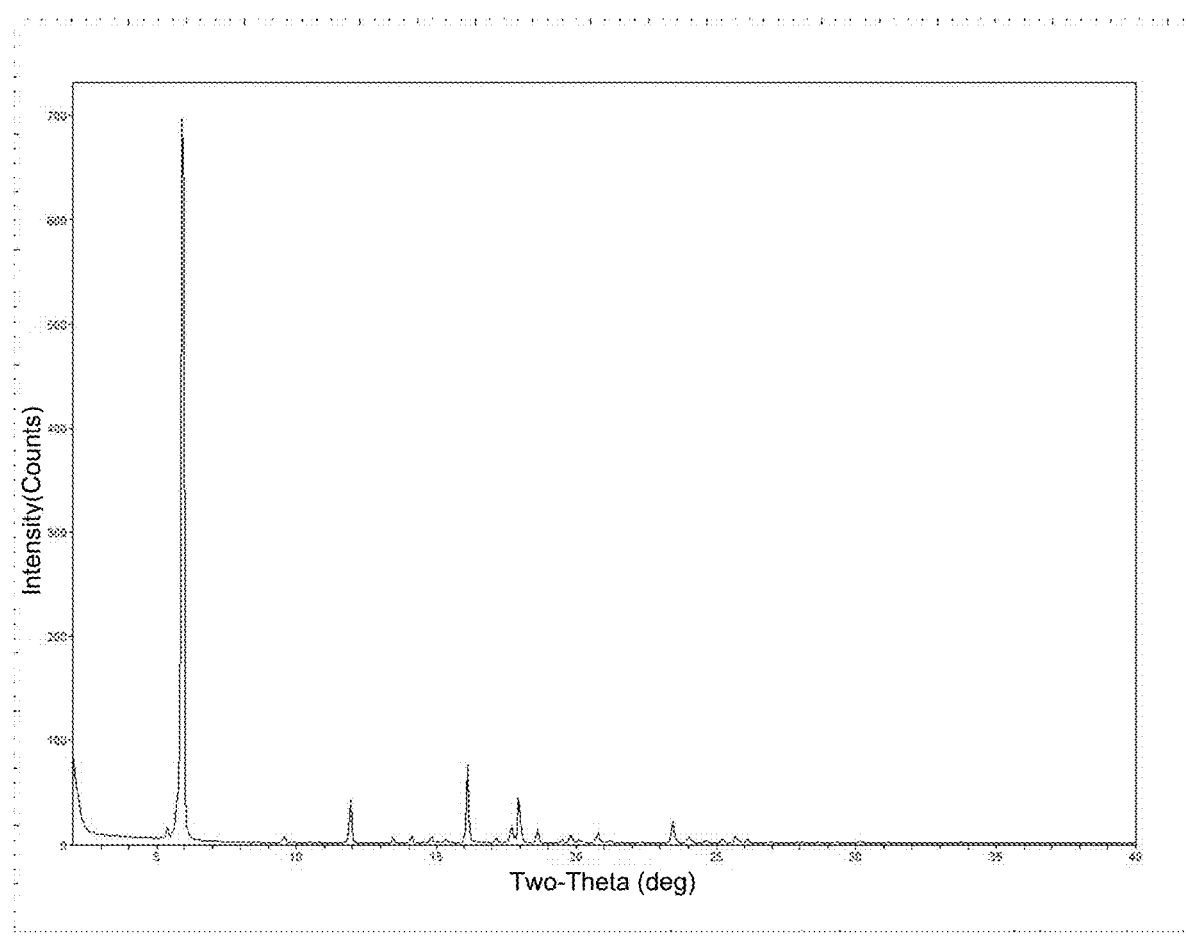
FIG. 3 shows the XRPD pattern of the compound of Formula (I) free base.

In certain embodiments, a third anhydrous crystalline form of a compound of Formula (I) free base has 2θ values of about 6.00±0.2, 12.00±0.2, 16.14±0.2, 17.72±0.2, 18.00±0.2, 18.64±0.2, and 23.50±0.2. In certain embodiments, an anhydrous crystalline form of a compound of Formula (I) mono-succinate salt has an XRPD pattern substantially as shown in FIG. 3, labeled free base.

In certain embodiments, the invention relates to a pharmaceutical composition comprising a crystalline compound of Formula (I) mono-succinate salt and one or more pharmaceutically acceptable excipients. In certain embodiments, the pharmaceutical composition is selected from tablets, capsules, and suspensions.

The term "substantially pure" as used herein, refers to a crystalline polymorph that is greater than 90% pure, meaning that contains less than 10% of any other compound, including the corresponding amorphous compound or an alternative polymorph of the crystalline salt. Preferably, the crystalline polymorph is greater than 95% pure, or even greater than 98% pure.

Methods of Making the Crystalline Forms of the Compound of Formula (I)

In certain embodiments, the invention relates to a method for the preparation of a crystalline compound having the structure of Formula (I), comprising
 a) providing a compound of Formula (I);
 b) adding an acid to form a mixture; and
 c) crystallizing the compound of Formula (I) from the mixture comprising the compound of Formula (I).

In certain embodiments, the crystalline compound made by the methods of the invention is anhydrous. In other embodiments, the crystalline compound made by the methods of the invention is a hydrate.

In certain embodiments, the compound of Formula (I) is present in at least one solvent. In certain embodiments, the acid is present in at least one solvent.

In certain embodiments, the compound of Formula (I) and the at least one solvent forms a solution. In certain embodiments, the compound of Formula (I) and the at least one solvent forms a slurry or a suspension. In certain embodiments, the acid and the at least one solvent forms a solution. In certain embodiments, the acid and the at least one solvent forms a slurry or a suspension.

In certain embodiments, the acid is selected from HCl, HBr, succinic acid, 1-OH-2-napthoic acid, citric acid, malic acid, tartaric acid, malonic acid, methanesulfonic acid, phosphoric acid, toluenesulfonic acid, and sulfuric acid. In preferred embodiments, the acid is succinic acid.

In certain embodiments, the solvent comprises acetone, acetonitrile, N,N-dimethylacetamide (DMA), dimethylformamide (DMF), dimethylsulfoxide (DMSO), dioxane, ethanol, ethyl acetate, heptanes, hexanes, isopropyl acetate, methanol, methylethyl ketone, N-methyl-2-pyrrolidone (NMP), tetrahydrofuran (THF), toluene, 2-propanol, 1-butanol, water, or any combination thereof. In certain preferred embodiments, for example to achieve Form A, the solvent is THF, ethanol or a mixture thereof. In other preferred embodiments, for example to achieve Form B, the solvent is ethanol.

In certain embodiments, the acid is present in at least one solvent and is added to the compound of Formula (I) to form a slurry, and the step of crystallizing the compound from the slurry comprises precipitating the compound from the slurry.

In certain embodiments, the compound of Formula (I), the acid, and at least one solvent form a solution, and the step of crystallizing the compound from the mixture comprises bringing the solution to supersaturation to cause the compound of Formula (I) to precipitate out of solution.

In certain embodiments, bringing the mixture comprising the compound of Formula (I) to supersaturation comprises the slow addition of an anti-solvent, such as heptanes, hexanes, ethanol, or another polar or non-polar liquid miscible with the organic solvent, allowing the solution to cool (with or without seeding the solution), reducing the volume of the solution, or any combination thereof. In certain embodiments, bringing the mixture comprising the compound of Formula (I) to supersaturation comprises adding an anti-solvent, cooling the solution to ambient temperature or lower, and reducing the volume of the solution, e.g., by evaporating solvent from the solution. In certain embodiments, allowing the solution to cool may be passive (e.g., allowing the solution to stand at ambient temperature) or active (e.g., cooling the solution in an ice bath or freezer).

In certain embodiments, the preparation method further comprises isolating the crystals, e.g., by filtering the crystals, by decanting fluid from the crystals, or by any other suitable separation technique. In further embodiments, the preparation method further comprises washing the crystals.

In certain embodiments, the mixture comprising the compound of Formula (I) is a slurry, and the step of crystallizing the compound from the mixture comprises precipitating the compound from the slurry. In some embodiments, the crystalline compound is isolated by centrifugation.

In certain embodiments, the preparation method further comprises inducing crystallization. The method can also comprise drying the crystals, for example under reduced pressure. In certain embodiments, inducing precipitation or crystallization comprises secondary nucleation, wherein nucleation occurs in the presence of seed crystals or interactions with the environment (crystallizer walls, stirring impellers, sonication, etc.).

In certain embodiments, washing the crystals comprises washing with a liquid selected from anti-solvent, acetonitrile, ethanol, heptanes, hexanes, methanol, tetrahydrofuran, toluene, water, or a combination thereof. As used herein, "anti-solvent" means a solvent in which the salt crystals are insoluble, minimally soluble, or partially soluble. In practice, the addition of an anti-solvent to a solution in which the salt crystals are dissolved reduces the solubility of the salt crystals in solution, thereby stimulating precipitation of the salt. In certain embodiments, the crystals are washed with a combination of anti-solvent and the organic solvent. In certain embodiments, the anti-solvent is water, while in other embodiments it is an alkane solvent, such as hexane or pentane, or an aromatic hydrocarbon solvent, such as benzene, toluene, or xylene. In certain embodiments, the anti-solvent is methanol.

In certain embodiments, washing the crystals comprises washing the crystalline compound of Formula (I) with a solvent or a mixture of one or more solvents, which are described above. In certain embodiments, the solvent or mixture of solvents is cooled prior to washing.

Uses of Crystal Forms of Compounds of Formula (I)

In various embodiments, the present invention provides compounds that inhibit the BMP signaling pathway, as well as methods to treat or prevent a disease or condition in a subject that would benefit by inhibition of BMP signaling. In various embodiments, compounds of the present invention include compounds of Formula (I) as disclosed herein and their salts (including pharmaceutically acceptable salts).

All references cited herein are incorporated by reference in their entirety as though fully set forth. Unless defined otherwise, technical and scientific terms used herein have the same meaning as commonly understood by one of ordinary skill in the art to which this invention belongs. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, NY 2006); Smith, *March's Advanced Organic Chemistry Reactions, Mechanisms and Structure* 7$^{th}$ ed., J. Wiley & Sons (New York, NY 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, NY 2012), provide one skilled in the art with a general guide to many of the terms used in the present application. For references on how to prepare antibodies, see Greenfield, *Antibodies A Laboratory Manual* 2$^{nd}$ ed., Cold Spring Harbor Press (Cold Spring Harbor NY, 2013); Köhler and Milstein, *Derivation of specific antibody producing tissue culture and tumor lines by cell fusion*, Eur. J. Immunol. 1976 Jul., 6(7):511-9; Queen and Selick, *Humanized immunoglobulins*, U.S. Pat. No. 5,585,089 (1996 Dec); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

Unless stated otherwise, the terms "a" and "an" and "the" and similar references used in the context of describing one or more embodiments of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g.," is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the term "soft tissue" is used to refer to tissues that connect, support or surround other structures and organs of the body. The term "soft tissue" can refer to muscles, ligaments, tendons, fascia, skin, fibrous tissues, fat, synovial membranes, nerves and/or blood vessels.

As used herein, the term "abnormal bone formation" refers to the generation or bone in an area, such as a soft tissue, where bone normally does not exist.

The terms "patient," "subject" and "individual" are used interchangeably herein, and refer to an animal, particularly a human, to whom treatment, including prophylactic treatment is provided. The term "subject" as used herein refers to human and non-human animals. The term "non-human animals" and "non-human mammals" are used interchangeably herein and includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In some embodiments, the subject is human. In another embodiment, the subject is an experimental animal or animal substitute as a disease model. In another embodiment, the subject is a domesticated animal including companion animals (e.g., dogs, cats, rats, guinea pigs, hamsters etc.).

As used herein, the term "at risk of having abnormal bone formation" refers to a subject that has been exposed to conditions that are known to cause abnormal bone formation in a population of subjects. While not every subject exposed to such conditions will go on to have abnormal bone formation, but all subjects exposed to these conditions can be considered to be "at risk." Such conditions typically include a trauma, for example, a musculoskeletal trauma, a central nervous system injury or a spinal cord injury.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

The terms "decrease," "reduced," "reduction," and "inhibit" are all used herein to mean a decrease or lessening of a property, level, or other parameter by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased," "increase," "enhance" and "activate" are all used herein to generally mean an increase of a property, level, or other parameter by a statically significant amount; for the avoidance of any doubt, the terms "increased," "increase," "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

The term "pharmaceutically acceptable" can refer to compounds and compositions which can be administered to a subject (e.g., a mammal or a human) without undue toxicity.

As used herein, the term "pharmaceutically acceptable carrier" can include any material or substance that, when combined with an active ingredient allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. The term "pharmaceutically acceptable carriers" excludes tissue culture media.

The phrase "activity of ALK2" means ALK-2 enzymatic activity (e.g., such as kinase activity; the ability of ALK-2 to phosphorylate BMP-responsive SMAD proteins) and/or ALK-2-mediated signaling (e.g., such as the ability of ALK-2 to mediate downstream signal transduction and transcriptional activity following activation of ALK-2 by binding of BMP ligands). In some embodiments, "activity of ALK2" means ALK2-mediated BMP signaling. In some embodiments, "activity of ALK2" means ALK2-mediated BMP-responsive gene transcription (e.g., transcriptional activity mediated by BMP/ALK2 signal transduction).

The phrase "activity of ALK5" means ALK-5 enzymatic activity (e.g., such as kinase activity; the ability of ALK-5 to phosphorylate TGF-β responsive SMAD proteins; the ability of ALK-5 to phosphorylate SMAD2 or SMAD3) and/or ALK-5-mediated signaling (e.g., such as the ability of ALK-5 to mediate downstream signal transduction and transcriptional activity following activation of ALK-5 by binding of TGF-β ligands). In some embodiments, "activity of ALK5" means ALK5-mediated TGF-β signaling. In some embodiments, "activity of ALK5" means ALK5-mediated TGF-β-responsive gene transcription (e.g., transcriptional activity mediated by TGF β/ALK5 signal transduction).

The phrase "activity of ALK1" means ALK-1 enzymatic activity (e.g., such as kinase activity; the ability of ALK-1 to phosphorylate BMP-responsive SMAD proteins) and/or ALK-1-mediated signaling (e.g., such as the ability of ALK-1 to mediate downstream signal transduction and transcriptional activity following activation of ALK-1 by binding of BMP ligands). In some embodiments, "activity of ALK1" means ALK1-mediated BMP signaling. In some embodiments, "activity of ALK1" means ALK1-mediated BMP-responsive gene transcription (e.g., transcriptional activity mediated by BMP/ALK1 signal transduction).

The phrase "activity of ALK4" means ALK-4 enzymatic activity (e.g., such as kinase activity; the ability of ALK-4 to phosphorylate activin-responsive SMAD proteins; the ability of ALK-4 to phosphorylate SMAD 2 or SMAD 3) and/or ALK-4-mediated signaling (e.g., such as the ability of ALK-4 to mediate downstream signal transduction and transcriptional activity following activation of ALK-4 by binding of activin ligands). In some embodiments, "activity of ALK4" means ALK4-mediated activin signaling. In some embodiments, "activity of ALK4" means ALK4-mediated activin-responsive gene transcription (e.g., transcriptional activity mediated by activin/ALK4 signal transduction).

The phrase "activity of ALK6" means ALK-6 enzymatic activity (e.g., such as kinase activity; the ability of ALK-6 to phosphorylate BMP-responsive SMAD proteins) and/or ALK-6-mediated signaling (e.g., such as the ability of ALK-6 to mediate downstream signal transduction and transcriptional activity following activation of ALK-6 by binding of BMP ligands). In some embodiments, "activity of ALK6" means ALK6-mediated BMP signaling. In some embodiments, "activity of ALK6" means ALK6-mediated GDF5 signaling. In some embodiments, "activity of ALK6" means ALK6-mediated BMP-responsive gene transcription (e.g., transcriptional activity mediated by BMP/ALK6 signal transduction).

Human ALK2 is a 509 amino acid protein. The protein sequence is published, for example, as GenBank accession number NP_001104537.1, (with corresponding nucleotide sequence at NM_001111067.2) UniProt entry Q04771.

Human ALK5 has, at least, two isoforms: a 503 amino acid protein (isoform 1) and a 426 amino acid protein. The protein sequence for human ALK5 isoform 1 is published, for example, as GenBank accession number NP_004603.1 (with corresponding nucleotide sequence at NM 004612.2). The protein sequence for the 426 amino acid isoform is published, for example, as GenBank accession number NP_001124388.1 with corresponding nucleotide sequence at NM 001130916.1). Information regarding both isoforms is also published as UniProt entry P36897.

Human ALK1 is a 503 amino acid protein. The protein sequence is published, for example, as GenBank accession number NP_001070869.1 (with corresponding nucleotide sequence at NM_001077401.1; transcript variant 2) and NP_000011.2 (with corresponding nucleotide sequence at NM 000020.2; transcript variant 1), UniProt entry P37023.

Human ALK3 is a 532 amino acid protein. The protein sequence is published, for example as GenBank accession number NP_004320 (with corresponding nucleotide sequence at NM 004329.2), UniProt entry P36894.

Human ALK4 has at least three isoforms. Isoform a is a 505 amino acid protein. The protein sequence is published, for example, as GenBank accession number NP_004293 (with corresponding nucleotide sequence at NM 004302), UniProt entry P36896.

Isoform a of human ALK6 is a 532 amino acid protein and isoform b is a 502 amino acid protein. The protein sequence for human ALK6 isoform a is published, for example, as GenBank accession number NP_001243722 (with corresponding nucleotide sequence at NM_001256793.1). The protein sequence for human ALK6 isoform b is published, for example, as GenBank accession number NP_001194 (with corresponding nucleotide sequence at NM 01203.2).

Note that each of the foregoing proteins are further processed in vivo, such as by the cleaving of a signal sequence, to yield a mature form.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that aspect of the invention.

The term "consisting of" refers to compositions, methods, and respective components thereof as described herein, which are exclusive of any element not recited in that description of the embodiment.

"Optional" or "optionally" means that the subsequently described circumstance may or may not occur, so that the description includes instances where the circumstance occurs and instances where it does not.

Alteration in Expression: An alteration in expression refers to a change in the level of a gene transcript (for example, mRNA) or gene product (for example, protein) that is detectable in a biological sample (such as a sample from a patient with Sjögren's syndrome, for example, in a salivary gland biopsy) relative to a control (such as a healthy subject). An "alteration" in expression includes an increase in expression (up-regulation) or a decrease in expression (down-regulation).

Bone Morphogenetic Protein 6 (BMP6): A member of the TGF-β superfamily of growth factors. Expression of BMP6 has been detected in several different mammalian tissues and cell types, including smooth muscle cells, growth plate chondrocytes, bronchiolar epithelium, cornea, epidermis, salivary gland and cells of the nervous system (Blessing et al., *J Cell Biol* 135(1):227-239, 1996). In vitro, BMP6 has been shown to inhibit cell division, promote terminal epithelial differentiation, and induce endochondral bone formation, osteoblastic differentiation and neuronal maturation (Heikinheimo et al., *Cancer Res* 59:5815-5821, 1999). BMP6 is also known as vegetal related growth factor (TGFB-related), VGR, VGR1 and VG-1-related protein. Genomic, mRNA and protein sequences for BMP6 from a number of different species are publically available, such as in the GenBank database from the National Center for Biotechnology Information.

Control: A "control" refers to a sample or standard used for comparison with an experimental sample, such as a salivary gland sample obtained from a patient with Sjögren's syndrome. In some embodiments, the control is a sample obtained from a healthy volunteer (also referred to herein as a "normal" control). In some embodiments, the control is a historical control or standard value (i.e. a previously tested control sample or group of samples that represent baseline or normal values).

Diagnosis: The process of identifying a disease by its signs, symptoms and/or results of various tests. The conclusion reached through that process is also called "a diagnosis." Forms of testing commonly performed include physical examination, blood tests, medical imaging, genetic analysis, urinalysis, and biopsy.

Diagnostically Significant Amount: In some embodiments, a "diagnostically significant amount" refers to an increase or decrease in the level of BMP6 (or any other gene or protein) in a biological sample that is sufficient to allow one to distinguish one patient population from another (such as a Sjögren's syndrome patient population from a group of healthy individuals). In some examples, the diagnostically significant increase or decrease is at least 2-fold, at least 3-fold, at least 4-fold, at least 5-fold, at least 6-fold, at least 8-fold, at least 10-fold, at least 15-fold, at least 20-fold, at least 30-fold or at least 40-fold. RT-PCR is provided herein as one example of how BMP6 expression can be detected. Immunoassays, such as an ELISA, are another example of a method for detecting expression of BMP6. However, one of skill in the art will recognize that other methods exist to measure gene expression and variation in detected expression levels can occur depending on the method that is used. Thus, the diagnostically significant amount may vary if another method of detection is used. In other embodiments, a "diagnostically significant amount" refers to an increase or decrease in electrical potential of a salivary gland that is sufficient to allow one to distinguish one patient population from another (such as a Sjögren's syndrome patient population from a group of healthy controls). In some examples, the diagnostically significant increase or decrease is about 10%, about 20%, about 30%, about 40% or about 50%.

Immunosuppressive Drug: Includes any agent or compound having the ability to decrease the body's immune system responses. In some embodiments, the immunosuppressive drug is a corticosteroid. In other embodiments, the immunosuppressive drug is a small molecule (such as cyclosporine) or a monoclonal antibody (such as a cytokine blocker).

Inhibitor: Any chemical compound, nucleic acid molecule, small molecule, peptide or polypeptide (such as an antibody) that can reduce activity of a gene product or interfere with expression of a gene. In some examples, an inhibitor can reduce or inhibit the activity of a protein that is encoded by a gene either directly or indirectly. Direct inhibition can be accomplished, for example, by binding to a protein and thereby preventing the protein from binding an intended target, such as a receptor. Indirect inhibition can be accomplished, for example, by binding to a protein's intended target, such as a receptor or binding partner, thereby blocking or reducing activity of the protein. In some examples, an inhibitor of the disclosure can inhibit a gene by reducing or inhibiting expression of the gene, inter alia by interfering with gene expression (transcription, processing, translation, post-translational modification), for example, by interfering with the gene's mRNA and blocking translation of the gene product or by post-translational modification of a gene product, or by causing changes in intracellular localization. In various embodiments of the present invention, an inhibitor is one or more compounds of Formula (I).

Inhibit Expression or Activity: As used herein, an agent that inhibits expression or activity of a gene (such as BMP6) is an agent that reduces the level of mRNA or protein expressed by the gene (such as BMP6) in a cell or tissue, or reduces (including eliminates) one or more activities of the gene or encoded protein (such as BMP6). Similarly, an agent that inhibits BMP signaling is any compound that inhibits, blocks or prevents signaling events in the BMP signaling pathway, such as phosphorylation of downstream targets, for example phosphorylation of SMAD1/5/8.

Measuring the Level of Expression: Quantifying the amount of a gene product present in a sample. Quantification can be either numerical or relative. Detecting expression of the gene product (such as BMP6 mRNA or protein) can be achieved using any method known in the art or described herein, such as by RT-PCR, antibody-binding (e.g., ELISA), or immunohistochemistry. In some embodiments, the change detected is an increase or decrease in expression as compared to a control. In some examples, the detected increase or decrease is an increase or decrease of at least two-fold, at least three fold or at least four-fold compared with the control. In other embodiments of the methods, the increase or decrease is of a diagnostically significant amount, which refers to a change of a sufficient magnitude to provide a statistical probability of the diagnosis.

Methyl CpG Binding Protein 2 (MECP2): DNA methylation is the major modification of eukaryotic genomes and plays an essential role in mammalian development. Human proteins MECP2, MBD1, MBD2, MBD3, and MBD4 comprise a family of nuclear proteins related by the presence in each of a methyl-CpG binding domain (MBD). Each of these proteins, with the exception of MBD3, is capable of binding specifically to methylated DNA. MECP2, MBD1 and MBD2 can also repress transcription from methylated gene promoters. In contrast to other MBD family members, MECP2 is X-linked and subject to X inactivation. MECP2 is dispensable in stem cells, but is essential for embryonic development. MECP2 gene mutations are the cause of most cases of Rett syndrome, a progressive neurologic developmental disorder and one of the most common causes of mental retardation in females. MECP2 is also known as RS; RTS; RTT; PPMX; MRX16; MRX79; MRXSL; AUTSX3; MRXS13; and DKFZp686A24160. Genomic, mRNA and protein sequences for MECP2 are publically available, such as in the GenBank database from the National Center for Biotechnology Information.

Noggin (NOG): A secreted protein that binds and inactivates members of the transforming growth factor-beta (TGF-beta) superfamily signaling proteins, such as BMP4 and BMP6. By diffusing through extracellular matrices more efficiently than members of the TGF-beta superfamily, this protein may have a principal role in creating morphogenic gradients. The protein appears to have pleiotropic effect, both early in development as well as in later stages. Nucleotide and amino acid sequences of noggin are publically available, such as in the GenBank database (see NCBI Gene ID 9241 for human noggin).

Non-Steroidal Anti-Inflammatory Drug (NSAID): A type of anti-inflammatory agent that works by inhibiting the production of prostaglandins. NSAIDS exert anti-inflammatory, analgesic and antipyretic actions. Examples of NSAIDS include ibuprofen, ketoprofen, piroxicam, naproxen, sulindac, aspirin, choline subsalicylate, diflunisal, fenoprofen, indomethacin, meclofenamate, salsalate, tolmetin and magnesium salicylate.

Restoring Salivary Flow (or Increasing Salivary Flow): The process of increasing salivary production in a subject with diminished salivary flow, such as may result from Sjögren's syndrome and/or an increase in BMP6 expression. An increase in salivary flow can be indicated by, for example, an increase in salivary flow rate and/or an increase in salivary flow volume. In some embodiments, restoring salivary flow can be accomplished by administering a therapeutic agent. In some examples, the therapeutic agent is a pharmaceutical, such as pilocarpine (Salagen™) or cevimeline (Evoxac™). In other examples, the therapeutic agent is an inhibitor of BMP6 expression or activity.

Restoring Tear Production: The process of increasing tear production in a subject with diminished tearing, such as may result from Sjögren's syndrome. In some embodiments, restoring tear production can be accomplished by administering a therapeutic agent. In particular examples, the therapeutic agent is an inhibitor of BMP6 expression or activity.

Salivary Glands: Exocrine glands that produce saliva. As used herein, a "salivary gland" includes any salivary gland in a human subject, including, for example, the parotid glands, minor salivary glands, submandibular glands, sublingual glands and Von Ebner's glands. There are over 600 minor salivary glands located throughout the oral cavity.

Sjögren's Syndrome (SS): An autoimmune disorder characterized by immune cells that attack and destroy the glands that produce tears and saliva. Sjögren's syndrome is not life-threatening or life-shortening, but can significantly reduce quality of life. The hallmark symptoms of the disorder are dry mouth and dry eyes. Sjögren's syndrome may also cause skin, nose and vaginal dryness, and can affect other organs of the body including the kidneys, blood vessels, lungs, liver, pancreas and brain. Sjögren's syndrome affects 1-4 million people in the United States, with women being nine times more likely to develop the disease. The majority of Sjögren's sufferers are at least 40 years old at the time of diagnosis.

A number of different criteria can be used to identify a subject having Sjögren's syndrome and include one or more of: (i) ocular symptoms (for example, persistent dry eyes and/or recurrent sensation of sand or gravel in eyes); (ii) oral symptoms (for example, daily feeling of dry mouth, persistently swollen salivary glands, and/or drinking liquids to swallow dry food); (iii) objective evidence of ocular involvement defined as a positive result of a Schirmer's test performed without anesthesia (≤5 mm in 5 minutes) and/or Rose bengal score or other ocular surface staining score (≥4 according to van Bijsterveld's scoring system; (iv) histopathology in minor salivary glands (measuring focus score or Tarpley score); (v) salivary gland involvement demonstrated with objective evidence of salivary gland involvement by a positive result for unstimulated whole salivary flow (≤1.5 ml in 15 minutes), parotid sialography showing the presence of diffuse sialectasias (punctate, cavitary, or destructive pattern) without evidence of obstruction in the major ducts, and/or salivary scintigraphy showing delayed uptake, reduced concentration and/or delayed excretion of tracer; or (vi) autoantibodies (presence in the serum of antibodies to Ro (SSA) or La (SSB) antigens, or both. Thus, in some embodiments, a subject exhibiting one or more of the above signs or symptoms is selected for treatment according to the methods disclosed herein.

The presence of sicca (dryness) symptoms (sicca symptomology) in the absence of another connective tissue disease is designated "primary Sjögren's syndrome." Primary Sjögren's syndrome can also be characterized in subjects having a positive result for any four of the six criteria listed above, as long as either histopathology (item iv) or serology (item vi) is positive, or the presence of any three of the four objective criteria listed above (that is, items iii, iv, v, vi). Patients with an autoimmune process (such as rheumatoid arthritis, systemic lupus erythematosus, progressive systemic sclerosis, scleroderma, or polymyositis), in the presence of item i or item ii listed above, plus any two criteria from items iii, iv, and v, are characterized as having "secondary Sjögren's syndrome."

Therapeutically Effective Amount: A quantity of a specified pharmaceutical or therapeutic agent sufficient to achieve a desired effect in a subject, or in a cell, being treated with the agent. The effective amount of the agent will be dependent on several factors, including, but not limited to the subject or cells being treated, and the manner of administration of the therapeutic composition.

X (Inactive)-Specific Transcript (Non-Protein Coding) (XIST): X inactivation is an early developmental process in mammalian females that transcriptionally silences one of the pair of X chromosomes, thus providing dosage equivalence between males and females. The process is regulated by several factors, including a region of chromosome X called the X inactivation center (XIC). The XIST gene is expressed exclusively from the XIC of the inactive X chromosome. The transcript is spliced but does not encode a protein. The transcript remains in the nucleus where it coats the inactive X chromosome. XIST is also known as XCE, XIC and SXI1. Genomic and RNA sequences for XIST are publically available, such as in the GenBank database from the National Center for Biotechnology Information.

| Abbreviations | |
|---|---|
| AAV | adeno-associated virus |
| ATP | adenosine triphosphate |
| BMP6 | bone morphogenetic protein 6 |
| BSA | bovine serum albumin |
| BW | body weight |
| CGH | comparative genomic hybridization |
| ELISA | enzyme-linked immunosorbent assay |
| EP | electrical potential |
| FS | focus score |
| HIF-1 alpha | hypoxia-inducible factor 1-alpha |
| HO | heterotopic ossification |
| HTS | hypotonic solution |
| HV | healthy volunteer |
| IFN | interferon |
| IL | interlukin |
| IM | intramuscular |
| IPA | Ingenuity Pathway Analysis |
| MECP2 | methyl CpG binding protein 2 |
| MyD88 | myeloid differentiation primary response gene 88 |
| NOD | non-obese diabetic |
| OD | optical density |
| O/N | overnight |
| PDGF | platelet-derived growth factor |
| pSS | primary Sjögren's syndrome |
| qPCR | quantitative polymerase chain reaction |
| RIN | RNA integrity number |
| RT | room temperature |
| RT-PCR | reverse transcriptase polymerase chain reaction |
| Runx2 | runt-related transcription factor 2 |
| RVD | regulated volume decrease |
| SFR | salivary flow rate |
| SG | salivary gland |
| SMG | submandibular gland |
| SS | Sjögren's syndrome |
| TEER | trans epithelial electric resistance |
| TGF | transforming growth factor |
| TRIF | TIR-domain-containing adapter-inducing interferon-β |
| WT | wild type |
| XIST | X (inactive)-specific transcript (non-protein coding) |

Further, unless otherwise required by context, singular terms shall include pluralities and plural terms shall include the singular.

It should be understood that this invention is not limited to the particular methodologies, protocols, and reagents, etc., described herein and as such can vary therefrom. The terminology used herein is for the purpose of describing particular embodiments only, and is not intended to limit the scope of the present invention, which is defined solely by the claims.

The methods and compositions provided herein are based, in part, on the discovery that one or more crystalline compounds or compositions described herein act as a BMP inhibitor by inhibiting signaling through ALK2, a BMP type I receptor. In addition, one or more crystalline compounds or compositions described herein is shown herein to be effective in the treatment and/or prevention of abnormal bone formation in soft tissue. Accordingly, provided herein are methods and compositions for the treatment of abnormal bone formation in soft tissue, comprising treatment with one or more crystalline compounds or compositions described herein.

In various embodiments, the present invention provides a method for treating the formation of abnormal bone in a soft tissue of a subject, the method comprising: administering a therapeutically effective amount of one or more crystalline compounds or compositions described herein. In some embodiments, the subject is determined to have or be at risk of having abnormal bone formation prior to treatment. In some embodiments, the subject has been subjected to a musculoskeletal trauma, a spinal cord injury or a central nervous system injury. In some embodiments, the formation of abnormal bone is associated with a heterotopic ossification disease. In some embodiments, the heterotopic ossification disease is selected from the group consisting of: acquired heterotopic ossification, fibrodysplasia ossificans progressive, anklyosing spondylosis, traumatic heterotopic ossification, burn- or blast-injury associated heterotopic ossification, and joint replacement surgery associated heterotopic ossification. In some embodiments, the soft tissue comprises muscles, tendons, ligaments and/or fascia. In some embodiments, at least one additional agent is administered to the subject. In some embodiments, the at least one additional agent comprises a corticosteroid, a non-steroidal anti-inflammatory drug (NSAID), a lipoxygenase inhibitor, a leukotriene inhibitor, a mast cell stabilizing agent, an anti-histamine, a TNF inhibitor, an IL-23 blocker, or an inhibitor of IL-1 signaling. In some embodiments, the therapeutically effective amount of one or more crystalline compounds or compositions described herein comprises a dose within the range of 5 mg/kg to 250 mg/kg. In some embodiments, the therapeutically effective amount of one or more crystalline compounds or compositions described herein does not cause weight loss greater than 20% of total body mass.

In various embodiments, the present invention provides a method for treating the formation of abnormal bone in a soft tissue of a subject, the method comprising: administering a therapeutically effective amount of an inhibitor of a BMP type I serine-threonine kinase receptor to the subject, wherein the inhibitor of a BMP type I serine-threonine kinase receptor is one or more crystalline compounds or compositions described herein. In some embodiments, the BMP type I serine-threonine receptor is ALK2, ALK3, or ALK6. In some embodiments, the BMP type I serine-threonine receptor is ALK2 or ALK3.

In various embodiments, the present invention provides a method for treating the formation of abnormal bone in a soft tissue of a subject, the method comprising: administering a therapeutically effective amount of an inhibitor of a BMP type II serine-threonine kinase receptor to the subject, wherein the inhibitor of a BMP type II serine-threonine kinase receptor is a one or more crystalline compounds or compositions described herein. In some embodiments, the BMP type II serine-threonine receptor is ACVR2A, ACVR2B, BMPR2, or TGFβR2.

In various embodiments, the present invention provides a method for inhibiting a serine-threonine kinase receptor in a subject, the method comprising: administering an inhibitor of the serine-threonine kinase receptor to the subject under conditions effective to inhibit the serine-threonine kinase receptor, wherein the inhibitor of the serine-threonine kinase receptor is one or more crystalline compounds or compositions described herein. In some embodiments, the serine-threonine kinase receptor is a BMP type I receptor, a BMP type II receptor, or a TGF-β type I receptor. In some embodiments, the serine-threonine kinase receptor is a BMP type I receptor. In some embodiments, the BMP type I receptor is ALK2, ALK3, or ALK6. In some embodiments, the BMP type I receptor is ALK2 or ALK3. In some embodiments, the serine-threonine kinase receptor is a BMP type II receptor. In some embodiments, the BMP type II receptor is ACVR2A, ACVR2B, BMPR2, or TGFβR2. In some embodiments, the serine-threonine kinase receptor is a TGF-β type I receptor. In some embodiments, the TGF-β type I receptor is ALK5.

In various embodiments, the present invention provides a method for identifying one or more compounds for inhibiting a serine-threonine kinase receptor, the method comprising: a) providing a sample comprising the serine-threonine kinase receptor; b) contacting the sample with one or more crystalline compounds or compositions described herein; and c) performing an assay to identify the one or more compounds that inhibit the serine-threonine kinase receptor, wherein the assay is an in vitro assay, an in vivo assay, or an ex vivo assay. In some embodiments, the serine-threonine kinase receptor is a BMP type I receptor, a BMP type II receptor, or a TGF-β type I receptor. In some embodiments, the assay is an in vitro assay.

In various embodiments, the present invention provides a method of treating a subject with Sjögren's syndrome, comprising: a) selecting a subject with increased expression of BMP6 in a salivary gland of the subject relative to a control; and b) administering to the subject a therapeutically effective amount of an agent that inhibits expression or activity of BMP6, thereby treating the subject with Sjögren's syndrome, wherein the agent that inhibits expression or activity of BMP6 is one or more crystalline compounds or compositions described herein. In some embodiments, the salivary gland is a minor labial salivary gland, parotid gland, or a submandibular gland.

In various embodiments, the present invention provides a method for treating a subject with diffuse intrinsic pontine glioma (DIPG), comprising selecting the subject with diffuse intrinsic pontine glioma (DIPG), and administering to the subject a therapeutically effective amount of one or more crystalline compounds or compositions described herein, thereby treating the subject with diffuse intrinsic pontine glioma (DIPG).

In various embodiments, the present invention provides a method for treating the formation of abnormal bone in a soft tissue of a subject, the method comprising: administering a therapeutically effective amount of an inhibitor of a TGF-β type I receptor serine-threonine kinase receptor to the subject, wherein the inhibitor of the TGF-β type I serine-threonine kinase receptor is a one or more crystalline compounds or compositions described herein. In some embodiments, the TGF-β type I receptor is ALK5.

In various embodiments, the present invention provides a method for inhibiting a serine-threonine kinase receptor in a subject, the method comprising: administering an inhibitor of the serine-threonine kinase receptor to the subject under conditions effective to inhibit the serine-threonine kinase receptor, wherein the inhibitor of the serine-threonine kinase receptor is one or more crystalline compounds or compositions described herein. In some embodiments, the serine-threonine kinase receptor is a BMP type I receptor, a BMP type II receptor, or a TGF-β type I receptor. In some embodiments, the serine-threonine kinase receptor is a BMP type I receptor. In some embodiments, the BMP type I receptor is ALK2, ALK3, or ALK6. In some embodiments, the BMP type I receptor is ALK2 or ALK3. In some embodiments, the serine-threonine kinase receptor is a BMP type II receptor. In some embodiments, the BMP type II receptor is ACVR2A, ACVR2B, BMPR2, or TGFβR2. In some embodiments, the serine-threonine kinase receptor is a TGF-β type I receptor. In some embodiments, the TGF-β type I receptor is ALK5.

In various embodiments, the present invention provides a method of increasing salivary flow in a subject, comprising: a) selecting a subject with increased expression of BMP6 in a salivary gland of the subject relative to a control; and b) administering to the subject a therapeutically effective amount of an agent that inhibits expression or activity of BMP6, thereby increasing salivary flow in the subject, wherein the agent that inhibits expression or activity of BMP6 is one or more crystalline compounds or compositions described herein, or a submandibular gland.

In various embodiments, the present invention provides method of increasing salivary flow in a subject, comprising: a) selecting a subject with increased expression of BMP6 in a salivary gland of the subject relative to a control; and b) administering to the subject a therapeutically effective amount of an agent that inhibits BMP signaling, thereby increasing salivary flow in the subject, wherein the agent that inhibits BMP signaling is one or more crystalline compounds or compositions described herein. In some embodiments, the salivary gland is a minor labial salivary gland, parotid gland, or a submandibular gland.

Heterotopic Ossification Diseases

The term "heterotopic ossification" refers to the abnormal formation of bone in soft tissue where bone typically does not exist. Acquired heterotopic ossification can occur with essentially any musculoskeletal trauma, spinal cord injury, central nervous system injury, head injury, cerebrovascular accident, sickle cell anemia, hemophilia, tetanus, poliomyelitis, multiple sclerosis, toxic epidermal necrolysis and burns. Examples of musculoskeletal trauma include, but are not limited to, hip, knee, shoulder, or elbow arthroplasty; fractures; joint dislocations; or soft-tissue trauma, with the *musculus* quadriceps femoris and *musculus brachialis*. Acquired heterotopic ossification can also be associated with fever, swelling, and erythema (e.g., local, patchy reddening of the skin). In one embodiment, neurogenic heterotopic ossification is not associated with local trauma.

Genetic diseases fibrodysplasia ossificans progressiva (FOP) and progressive osseous heterplasia (POH) are the most severe manifestations of heterotopic bone formation. FOP occurs rarely and is a result of a mutation in ACVR1, which encodes a bone morphogenetic protein type I receptor. Patients with POH have inactivating mutations of the GNAS gene, which also can give rise to Albright's hereditary osteodystrophy (AHO) when the mutations are inherited from the mother.

Myositis ossificans circumscripta is characterized by the intramuscular proliferation of fibroblasts, new bone, and/or cartilage.

HO typically occurs between 3 weeks and 12 weeks following an injury. Heterotopic ossification can be reliably diagnosed by computed tomography, bone scintigraphy and ultrasonography. Two to six weeks later, the abnormal bone formation has progressed to the point that it is detectable by radiography. Bony maturation typically occurs within six months.

Conventional treatment of Heterotopic ossification: Conventional treatment usually involves non-steroidal anti-inflammatory drugs (indomethecin, rofecoxib), or bisphosphonate (etidronate, pamidronate), Coumadin/warfarin, salicylates, and/or local radiation can also be administered. Often, surgery is the only option for treatment.

Outcome of treatment can be measured by a standard radiological grading system for HO, which includes measurements related to changes in range of motion in the affected joint measured by goniometry, mean length of time to objective improvement of HO-related clinical symptoms or signs, changes in standardized functional or joint-specific measures.

Uses

BMPs and TGF-beta signaling pathways are essential to normal organogenesis and pattern formation, as well as the normal and pathological remodeling of mature tissues. Defects in the BMP signaling pathway are implicated in a number of congenital and acquired disease processes, including Hereditary Hemorrhagic Telangectasia syndrome, Primary Pulmonary Hypertension, Juvenile Familial Polyposis, as well as sporadic renal cell and prostate carcinomas. It has been suggested that in certain disease states associated with defective signaling components, attenuated BMP signaling might be a cause, while other findings have suggested that in some contexts excess BMP signaling might be pathogenic (Waite et al. *Nat. Rev. Genet.* 4:763-773, 2005; Yu et. *J Biol. Chem.* 280:24443-24450, 2003). The ability to modulate BMP signaling experimentally would provide a means for investigating therapy, and for determining the root causes of these conditions. One or more crystalline compounds or compositions described herein are inhibitors of ALK2, a BMP type 1 receptor and can be used to disrupt signaling through the BMP pathway.

Treatment of Anemia, Including Iron Deficiency and Anemia of Chronic Disease

For a review, see Weiss et al. *N. Engl. J Med.* 352:1011-1023, 2005. Anemia of inflammation (also called anemia of chronic disease) can be seen in patients with chronic infections, autoimmune diseases (such as systemic lupus erythematosis and rheumatoid arthritis, and Castleman's disease), inflammatory bowel disease, cancers (including multiple myeloma), and renal failure. Anemia of inflammation is often caused by maladaptive expression of the peptide hormone hepcidin. Hepcidin causes degradation of ferroportin, a critical protein that enables transport of iron from intracellular stores in macrophages and from intestinal epithelial cells. Many patients with renal failure have a combination of erythropoietin deficiency and excess hepcidin expression. BMP signaling induces expression of hepcidin and inhibiting hepcidin expression with BMP antagonists increases iron levels. Compounds as described herein can be used to treat anemia due to chronic disease or inflammation and associated hyperhepcidinemic states.

The inflammatory cytokine IL-6 is thought to be the principal cause of elevated hepcidin expression in inflammatory states, based upon the elevation of IL-6 in anemia of inflammation of diverse etiologies, the effects of chronic IL-6 administration in vivo, and the protection against anemia in rodents deficient in IL-6 (Weiss et al. *N. Engl. J Med.* 352:1011-1023, 2005). It has been shown that stimulating hepatoma cell lines with IL-6 induces hepcidin expression, while treatment with a BMP antagonist abrogates IL-6-induced hepcidin expression (Yu et al. *Nat. Chem. Biol.* 4:33-41, 2008). Moreover, BMP antagonists can inhibit hepcidin expression induced by injection of pathogenic bacteria in vivo. It has also been shown that systemic iron administration in mice and zebrafish rapidly activates BMP-responsive-SMADs and hepcidin expression in the liver, and that BMP antagonism effectively blocks these responses (Yu et al. *Nat. Chem. Biol.* 4:33-41, 2008). The functional importance of BMP signaling in iron regulation is supported by the previous finding that BMP antagonists can inhibit hepcidin expression and raise serum iron levels in vivo (data not shown). Taken together these data indicate that iron- and inflammation-mediated regulation of hepcidin and circulating iron levels require BMP signaling. Thus, one or more crystalline compounds or compositions described herein which disrupt BMP signaling through ALK2 can be used to alter iron availability in diverse circumstances for therapeutic benefit.

Compounds and/or pharmaceutical compositions as described herein can be used in anemic states to (i) augment the efficacy of dietary iron or oral iron supplementation (which is safer than intravenous administration of iron) to increase serum iron concentrations; (ii) augment build-up of hemoglobin in the blood in anticipation of surgery or to enable blood donation for self in anticipation of surgery; and (iii) enhance the efficacy of erythropoietin and its relatives, thereby enabling lower doses of erythropoietin to be administered for anemia while minimizing known toxicities and side effects of erythropoietin (i.e., hypertension, cardiovascular events, and tumor growth).

B. Treatment of Fibrodysplasia Ossificans Progressiva (FOP)

In various embodiments, the present disclosure relates to the treatment and/or prevention of a disease or disorder comprising abnormal bone growth in a soft tissue of a subject. Heterotopic ossification (HO) involves unwanted bone growth that may be characterized by inappropriate differentiation of cells into bone-forming cells. This condition leads to bone formation, usually near joints, where the bone formation often limits the mobility of the joint. HO may follow neurological injury and direct injury to soft tissue such as muscles or connective tissue around the joint in which HO later develops.

There are three recognized etiologies of HO: traumatic, neurogenic, and genetic. Traumatic HO typically follows fractures, dislocations, operative procedures, and severe burns. Most commonly, HO is seen around the hip after fracture and open reduction-internal fixation (ORIF) procedures or total hip arthroplasties (THA). As well, HO is often associated with pathologies such as traumatic brain injury (TBI), spinal cord injury (SCI), infections of the central nervous system (CNS), tumors, strokes, tetanus, polio, tabes *dorsalis*, multiple sclerosis, and selective posterior rhizotomy. The presence of idiopathic muscle spasticity is also associated with the development of HO.

Bone morphogenetic proteins (BMP) exhibit broad spectrum of biological activities in various tissues, including bone, cartilage, blood vessels, heart, kidney, neurons, liver and lung. BMPs are members of the transforming growth factor-β (TGF-β) family that bind to type II and type I serine-threonine kinase receptors, and transduce signals through Smad and non-Smad signaling pathways. Fibrodysplasia ossificans progressiva (FOP), one type of heterotopic ossification disease, is an autosomal-dominant rare disease that affects one person in every 1-2 million. It is characterized by malformation of the great (big) toes during embryonic development and by progressive heterotopic endochondral ossification (HEO) postnatally, which leads to the formation of a second skeleton of heterotopic bone. Individuals with the classical features of FOP have the identical heterozygous activating mutation (R206H) in the gene encoding ACRV1 (also known as ALK2), a BMP type 1 receptor. No effective treatment currently exists for this rare and devastating disease. As such, there remains a need for compositions and methods for treating heterotopic ossification and heterotopic ossification diseases and disorders.

FOP is caused by the presence of a constitutively-active mutant form of ALK2 in affected individuals (Shore et al. *Nat. Genet.* 38:525-527, 2006). A specific inhibitor of BMP signaling such as one or more crystalline compounds or compositions described herein can be used to prevent excessive bone formation in response to trauma, musculoskeletal stress or inflammation. Such compounds can also be used to aid in regression of pathologic bone. One or more crystalline compounds or compositions described herein can be administered systemically or locally to concentrate or limit effects to areas of trauma or inflammation.

One or more crystalline compounds or compositions described herein, ALK2 inhibitors, can be used as chronic therapy to suppress spontaneous bone formation in individuals who are highly susceptible. One or more crystalline compounds or compositions described herein can be used as a chronic therapy to suppress spontaneous bone formation in individuals who are highly susceptible. Transient therapy can be used to prevent abnormal bone formation in FOP individuals who develop osteomas or pathologic bone most frequently in association with trauma by administration before, during, or even after the traumatic incident. Transient therapy with BMP inhibitors (e.g., one or more crystalline compounds or compositions described herein as described herein can be used before, during or immediately after necessary or emergent medical or surgical procedures (and even important immunizations and tooth extractions) in individuals with FOP, to prevent pathologic calcification. Combination therapy with other bone inhibiting agents, immune modulatory or anti-inflammatory drugs (such as NSAIDs, steroids, cyclosporine, cyclophosphamide, azathioprine, methotrexate, rituxumab, etanercept, or similar drugs) may increase the effectiveness of BMP antagonists in inhibiting heterotopic bone formation in this disorder.

Provided herein are methods and compositions for the treatment and/or prevention of abnormal bone formation in a soft tissue. In certain embodiments, the methods and compositions treat and/or prevent a disease or disorder comprising abnormal bone formation in soft tissue. Exemplary diseases or disorders that can be treated with the methods and compositions described herein include, but are not limited to, heterotopic ossification diseases such as fibrodysplasia ossificans progressiva, anklyosing spondylosis, traumatic heterotopic ossification, burn- or blast-injury associated heterotopic ossification, and joint replacement surgery associated heterotopic ossification.

Accordingly, provided herein in one aspect is a method for treating and/or preventing the formation of abnormal bone in a soft tissue of a subject, the method comprising: administering a therapeutically effective amount of a pharmaceutical composition comprising one or more crystalline compounds or compositions described herein.

C. Treatment of Cancers

Excessive BMP signaling, which could arise due to over-expression of BMPs, or, paradoxically, as a result of loss of BMP type II receptor expression, may contribute to the oncogenesis, growth or metastasis of certain solid tumors, including breast, prostate carcinomas, bone, lung, and renal cell carcinomas (Yu et al. *J. Biol. Chem.* 280:24443-24450, 2008; Waite et al. *Nat. Rev. Genet.* 4:763-773, 2003; Alarmo et al. *Genes, Chromosomes Cancer* 45:411-419, 2006; Kim et al. *Cancer Res.* 60:2840-2844, 2000; Kim et al. *Cl/n. Cancer Res.* 9:6046-6051, 2003; Kim et al. *Oncogene* 23:7651-7659, 2004). If increased BMP activity associated with BMP over-expression or BMP type II receptor deficiency contributes to the pathogenesis of disease, then inhibiting BMP signaling activity using compounds as described herein at the level of BMP type I receptors (downstream of both ligands and type II receptor) could be an effective means of normalizing BMP signaling activity and potentially inhibiting tumor growth or metastasis.

One or more crystalline compounds or compositions described herein are contemplated herein for use in treating cancer, for example, they can be used to slow or arrest the growth or metastasis of such tumor cells (as well as other tumor constituent cell types) for clinical benefit, either as adjunctive or primary chemotherapy. Also, BMP inhibitors as described herein can be used to interfere with the bone metastatic properties of certain types of cancers (e.g., adenocarcinoma, such as prostate and breast carcinomas). In addition, one or more crystalline compounds or compositions described herein as described herein can be used to inhibit osteoblastic activity in tumors that either form bone or are bone-derived, such as osteosarcomas (as adjunctive or primary chemotherapy). Further, one or more crystalline compounds or compositions described herein as described herein can be used to inhibit osteoclastic activity (also regulated by BMPs through the action of its target gene RANKL), which is pathologically increased in conditions such as multiple myeloma and other bone-targeted tumors. Application of BMP inhibitors in these conditions may reduce the presence of osteolytic lesions and bone fractures due to tumor involvement. In some embodiments, the cancer is diffuse intrinsic pontine glioma (DIPG).

D. Treatment of Pathologic Bone Formation

Compositions comprising one or more crystalline compounds or compositions described herein as described herein can be used to treat or ameliorate pathologic bone formation/bone fusion in inflammatory disorders, such as ankylosing spondylitis or other "seronegative" spondyloarthropathies, in which autoimmunity and inflammation in such disorders appear to stimulate bone formation. One application of the compounds would be to prevent excess bone formation after joint surgery, particularly in patients with ankylosing spondylitis or rheumatoid arthritis. Compositions comprising one or more crystalline compounds or compositions described herein as described herein can also be used to prevent calcinosis (dystrophic soft-tissue calcification) in diseases such as systemic lupus erythematosus, scleroderma, or dermatomyositis.

Blunt traumatic injury to muscles can cause abnormal bone formation within muscle in certain individuals, resulting in a disorder called myositis ossificans traumatica (Cushner et al. *Orthop. Rev.* 21:1319-1326, 1992.). Head trauma and burn injury can also induce heterotopic bone formation markedly impairing patient rehabilitation and recovery. Treatment with one or more crystalline compounds or compositions described herein as described herein, optionally in addition to anti-inflammatory medications usually prescribed for such a condition (e.g., non-steroidal anti-inflammatory drugs such as indomethacin or ibuprofen) can help to prevent the formation of pathologic bone in predisposed individuals, or to help lessen or regress lesions in individuals recently or remotely affected. Very rarely other muscles have been described to develop ossification in the presence of injury or trauma, including heart muscle, and similar treatment with a BMP inhibitor as described herein could be helpful in those circumstances.

E. Treatment of Ectopic or Maladaptive Bone Formation

BMP signals and their transcriptional targets are implicated in intimal and medial vascular remodeling and calcification in Monckeberg's vascular calcification disease and in atheromatous vascular disease (Bostrom et al. *J. Clin. Invest.* 91:1800-1809, 1993; Tyson et al. *Arterioscler. Thromb. Vasc. Biol.* 23:489-494, 2003). BMPs and BMP-induced osteodifferentation are also implicated in cardiac valvular calcification. Native cardiac valves can calcify particularly when they are already abnormal. A classic example is bicuspid aortic valve—these valves typically become calcified leading to stenosis. Patients with calcific aortic valve stenosis often require cardiac surgery for valve replacement. Abnormal calcification can adversely affect the function of prosthetic vascular grafts or cardiac valves. For example, prosthetic heart valves become calcified leading to narrowing and often leakage.

One or more crystalline compounds or compositions described herein as described herein can be used to inhibit vascular or valvular calcific disease alone or in combination with atheromatous disease, renal disease, renal osteodystrophy or parathyroid disease.

Pharmaceutical compositions comprising one or more compounds of Formula I as described herein can be used to inhibit vascular or valvular calcific disease alone or in combination with atheromatous disease, renal disease, renal osteodystrophy or parathyroid disease.

One or more crystalline compounds or compositions described herein as described herein can be used to inhibit calcification of prosthetic vascular or valvular materials by systemic or local administration or direct incorporation into prosthesis materials or other implants (e.g., in admixture with a polymer that coats or constitutes all or part of the implant or prosthesis).

Pharmaceutical compositions comprising one or more crystalline compounds or compositions described herein as described herein can be used to inhibit calcification of prosthetic vascular or valvular materials by systemic or local administration or direct incorporation into prosthesis materials or other implants (e.g., in admixture with a polymer that coats or constitutes all or part of the implant or prosthesis In some instances, it is desired to delay fracture healing following a bone fracture, or to purposely inhibit fracture healing in certain locations to prevent impairment of function by maladaptive bone formation. For example, if a fracture occurs and for medical or practical reasons surgery cannot be performed immediately, fracture healing can be temporarily "suspended" by use of one or more crystalline compounds or compositions described herein as described herein, until definitive surgery or manipulation can be performed. This could prevent the need for subsequent intentional re-fracture in order to ensure correct apposition of bone fragments, for example. It is expected that upon stopping administration of one or more crystalline compounds or compositions described herein normal fracture healing processes would ensue if the period of treatment is relatively short. In other cases, any amount of novel bone growth might impair function, such as when fracture affects a joint directly. In these cases, global or local inhibition of BMP activity (by systemic or local delivery of a BMP antagonist as described herein via diffusion from a local implant or matrix) can be used to inhibit fracture healing or prevent fracture calluses at the critical areas.

F. Immune Modulation Via BMP Antagonists

BMPs have been reported to attenuate the inflammatory or immune response (Choi et al. *Nat. Immunol.* 7:1057-1065, 2006; Kersten et al. BMC Immunol. 6:9, 2005), which can impair an individual's ability to fight infections (i.e., viral, bacterial, fungal, parasitic, or tuberculosis). One or more crystalline compounds or compositions described herein, inhibitors of BMP signaling through ALK2, can be used to augment the inflammatory or immune response enabling individuals to clear infections more rapidly. One or more crystalline compounds or compositions described herein can be used to augment the inflammatory or immune response enabling individuals to clear infections more rapidly.

Lymphocytes and other immune cells express BMP receptors on their cell surfaces, and there is growing evidence that BMPs regulate the development and maturation of various humoral and cellular immunologic compartments, and regulate humoral and cellular immune responses in mature organisms. The effects of BMP signals on immune cells are likely to be context-specific, as is commonly known for the effects of numerous cytokines of immunologic importance, and thus whether they augment or diminish the development or function of particular lymphocyte populations must be empirically determined. BMP antagonism using compounds as described herein may be an effective strategy for intentionally biasing the development of cellular, innate, or humoral immune compartments for therapy, or a strategy for the therapeutic deviation of immune responses in mature immune systems. These strategies may target inborn disorders of cellular, innate, or humoral immunity, or target disorders in which immune responses are inappropriately weak (e.g., as an adjuvant to promote successful antigen sensitization when immunization is difficult or ineffective by other means), or target disorders in which immune responses are excessive or inappropriate (e.g., autoimmunity and autosensitization). BMP antagonists as described herein may also be effective in some contexts for the intentional induction of immune tolerance (i.e., in allotransplantation or autoimmunity).

G. Treatment of Skin Diseases

Expansion of cultured keratinocytes—In vitro, BMPs inhibit keratinocyte proliferation and promote differentiation (reviewed in Botchkarev et al. Differentiation 72:512-526, 2004). In patients in need of skin grafting (e.g., after burns), skin grafts are made from cultured keratinocytes. The keratinocytes can be derived from other animals (xenografts), but these are only temporary as they are typically rejected by the immune system. Keratinocytes can be derived from the patient themselves and can be grown into sheets of cells in the laboratory (cultured epithelial autografts). It is unlikely that the patient will reject keratinocytes derived from his/her own body. Addition of BMP antagonists as described herein to keratinocyte cultures can be used to facilitate keratinocyte proliferation enabling patients to receive grafts sooner.

Improved epithelialization—BMP6 is highly expressed in skin injury, and high levels of BMP6 are detected in chronic human wounds of different etiologies (Kaiser et al. J. Invest. Dermatol. 111:1145-1152, 1998). In mice overexpressing BMP6 in their skin, reepithelialization and healing skin wounds were significantly delayed (Kaiser et al. J. Invest. Dermatol. 111:1145-1152, 1998). Improved epithelialization can reduce scar formation. Topical or systemic administration of one or more crystalline compounds or compositions described herein is contemplated herein to augment epithelialization of skin wounds, for example, in the treatment of pressure ulcers (bed sores) or non-healing or poorly-healing skin ulcers (e.g., in patients with peripheral vascular disease, diabetes mellitus, venous incompetence). Compounds would also be expected to decrease scar formation.

Promotion of hair growth—Growth of hair follicles on the scalp is cyclic with three phases: anagen (the growth phase), catagen (the involutional phase), and telogen (resting phase). Recent evidence indicates that BMP signals delay the transition from telogen to anagen (Plikus et al. Nature 451:340-344, 2008). Inhibition of BMP signaling using one or more crystalline compounds or compositions described herein as described herein can shorten the telogen phase and increase the number of follicles in the anagen phase. One or more crystalline compounds or compositions described herein can be used to treat circumstances wherein hair follicles are insufficient or when hairs are being lost more frequently than they are grown. These circumstances include androgenic alopecia (male pattern balding), alopecia greata, and telogen effluvium.

Treatment of psoriasis—Psoriasis is an inflammatory skin disorder which can occur following skin trauma and the ensuing repair and inflammation (Koebner phenomenon). BMPs can participate in repair and inflammatory mechanisms that cause psoriasis, since over-expression of BMP6 in the skin of mice leads to skin lesions similar to those seen in patients with psoriasis (Blessing et al. J. Cell. Biol. 135:227-239, 1996). One or more crystalline compounds or compositions described herein can be administered topically or systemically to treat established psoriasis or prevent its development after skin injury.

Treatment of corneal scarring—BMP6 expression is associated with conjunctival scarring (Andreev et al. Exp. Eye Res. 83:1162-1170, 2006). One or more crystalline compounds or compositions described herein can be used to prevent or treat corneal scarring and the resulting blindness.

H. Treatment of Systemic Hypertension

Infusion of BMP4 induces systemic hypertension in mice (Miriyala et al. Circulation 113:2818-2825, 2006). Vascular smooth muscle cells express a variety of BMP ligands. BMPs increase the expression of voltage gated potassium channels and thereby increase constriction of vascular smooth muscle (Fantozzi et al. Am. J. Physiol. Lung Cell. Mol. Physiol. 291: L993-1004, 2006). Thus, one or more crystalline compounds or compositions described herein are contemplated herein to inhibit BMP signaling, which can be used to reduce blood pressure. Sustained reduction of blood pressure in patients with hypertension is expected to prevent myocardial infarction, congestive heart failure, cerebrovascular accidents, and renal failure. Treatment as described herein can be used to target the hypertension in specific vascular beds, such as in pulmonary hypertension via local delivery (e.g., via aerosol).

Treatment of Pulmonary Hypertension

BMP signaling contributes to the pathogenesis of pulmonary hypertension. For example, mice with decreased BMP4 levels are protected from the pulmonary hypertension and pulmonary vascular remodeling induced by breathing low oxygen concentrations for prolonged periods (Frank et al. Circ. Res. 97:496-504, 2005). Moreover, mutations in the gene encoding the type II BMP receptor (BMPRII) are frequently found in patients with sporadic and familial pulmonary arterial hypertension. It might be anticipated that decreased BMP signaling might cause pulmonary hypertension. However, Yu and colleagues (Yu et al. J. Biol. Chem. 280:24443-24450, 2008) reported that BMPRII deficiency paradoxically increases BMP signaling by subsets of BMP ligands, and thus increased BMP signaling may actually contribute to the development of pulmonary hypertension.

One or more crystalline compounds or compositions described herein can be used to prevent the development of pulmonary arterial hypertension in patients at risk for the disease (e.g., patients with BMPRII mutations) or to treat patients with idiopathic or acquired pulmonary arterial hypertension. Decreased pulmonary hypertension in individuals treated as described herein are expected to have a decrease in shortness of breath, right ventricular hypertrophy, and right ventricular failure.

Pharmaceutical compositions comprising one or more crystalline compounds or compositions described herein can be used to prevent the development of pulmonary arterial hypertension in patients at risk for the disease (e.g., patients with BMPRII mutations) or to treat patients with idiopathic or acquired pulmonary arterial hypertension. Decreased pulmonary hypertension in individuals treated as described herein are expected to have a decrease in shortness of breath, right ventricular hypertrophy, and right ventricular failure.

Treatment of Ventricular Hypertrophy

BMP-10 levels are increased in the hypertrophied ventricles of rats with hypertension, and this BMP ligand induces hypertrophy in cultured neonatal rat ventricular myocytes (Nakano et al. Am. J. Physiol. Heart. Circ. Physiol. 293: H3396-3403, 2007). Inhibition of BMP-10 signaling can be used to prevent/treat ventricular hypertrophy. Ventricular hypertrophy can lead to congestive heart failure due to diastolic dysfunction. Pharmaceutical compositions comprising one or more crystalline compounds or compositions described herein may prevent/treat congestive heart failure.

Treatment of Neurologic Disorders

Treatment of spinal cord injury and neuropathy—BMPs are potent inhibitors of axonal regeneration in the adult spinal cord after spinal cord injury (Matsuura et al. J. Neurochem. 2008). Expression of BMPs is reported to be elevated in oligodendrocytes and astrocytes around the injury site following spinal cord contusion. Intrathecal administration of noggin, a BMP inhibitor, led to enhanced locomotor activity and significant regrowth of the corticospinal tract after spinal cord contusion.

RGMa inhibits axonal growth and recovery after spinal cord injury, as well as synapse re formation, effects which are blocked by an antibody directed against RGMa (Hata et al. J. Cell. Biol. 173:47-58, 2006; Kyoto et al. Brain Res. 1186:74-86, 2007). RGMa enhances BMP signaling (Babitt et al. J. Biol. Chem. 280:29820-29827, 2005) suggesting that BMP signaling may be responsible for preventing axonal growth and recovery.

Based on these considerations, treatment with one or more crystalline compounds or compositions described herein as described herein would be expected to increase axonal growth and recovery after spinal cord injury. Treatment as described herein would be expected to prevent/treat neuropathies associated with a wide spectrum of disorders including diabetes mellitus. In addition, treatment with one or more crystalline compounds or compositions described herein as described herein can be used treat both the pain and motor dysfunction associated with neuropathies.

Treatment of neurologic disorders associated with central nervous system inflammation—BMP4 and 5 have been detected in multiple sclerosis and Creutzfeldt-Jakob disease lesions (Deininger et al. Acta Neuropathol. 90:76-79, 1995). BMPs have also been detected in mice with experimental autoimmune encephalomyelitis, an animal model of multiple sclerosis (Ara et al. J. Neurosci. Res. 86:125-135, 2008). Treatment as described herein can be used to prevent or treat multiple sclerosis as well as other neurologic disorders associated with central nervous system inflammation, or maladaptive injury repair processes mediated by BMP signals.

Treatment of dementias-Inhibitors of BMP signaling can promote neurogenesis in mouse neural precursor cells (Koike et al. J. Biol. Chem. 282: 15843-15850, 2007). Treatment with one or more crystalline compounds or compositions described herein as described herein can be used to augment neurogenesis in a variety of neurologic disorders associated with accelerated loss of neurons including cerebrovascular accidents and Alzheimer's Disease, as well as other dementias.

Altering memory and learning—BMP signaling has an important role in the development and maintenance of neurons involved in memory and cognitive behavior. For example, mice deficient in the BMP antagonist, chordin, have enhanced spatial learning but less exploratory activity in a novel environment (Sun et al. J. Neurosci. 27:7740-7750, 2007). Treatment with one or more crystalline compounds or compositions described herein as described herein can be used to alter or prevent memory or learning, for example, inducing amnesia for anesthesia or in other situations likely to cause distress, or to prevent Post-Traumatic Stress Disorder.

Treatment of Atherosclerosis

Abundant evidence indicates that BMP ligands are pro-inflammatory and pro-atherogenic in the blood vessel wall (Chang et al. Circulation 116:1258-1266, 2007). Knocking-down expression of BMP4 decreased inflammatory signals, whereas knocking-down BMP antagonists (eg follistatin or noggin) increased inflammatory signals. Treatment with one or more crystalline compounds or compositions described herein as described herein can be used to reduce vascular inflammation associated with atherosclerosis, autoimmune disease, and other vasculitides. By decreasing atherosclerosis, treatment as described herein would decrease acute coronary syndromes (angina pectoris and heart attack), transient ischemic attacks, stroke, peripheral vascular disease, and other vascular ischemic events. Moreover, in so far as atherosclerosis contributes to the pathogenesis of aneurysm formation, compounds as described herein can be used to slow the progression of aneurysm formation decreasing the frequency of aneurismal structure and the requirement for vascular surgery.

As BMPs and many of the BMP-induced gene products that affect matrix remodeling are overexpressed in early atherosclerotic lesions, BMP signals can promote plaque formation and progression (Bostrom et al. J Clin Invest. 91: 1800-1809. 1993; Dhore et al. Arterioscler Thromb Vasc Biol. 21: 1998-2003. 2001). BMP signaling activity in the atheromatous plaque can thus represent a form of maladaptive injury-repair, or can contribute to inflammation. Over time, BMP signals can also induce resident or nascent vascular cell populations to differentiate into osteoblast-like cells, leading to intimal and medial calcification of vessels (Hruska et al. Circ Res. 97: 105-112. 2005). Calcific vascular disease, or arteriosclerosis, is associated with decreased vascular distensibility, and increased risk of cardiovascular events and mortality, and is particularly problematic when associated with underlying atherosclerotic disease (Bostrom et al. Crit Rev Eukaryot Gene Expr. 10: 151-158. 2000). Both atherosclerotic and calcific lesions may be amenable to regression, however, if signals which contribute to their progression can be intercepted (Sano et al. Circulation. 103: 2955-2960. 2001). In certain aspects, treatment with one or more crystalline compounds or compositions described herein as described herein can be used to limit the progression of atheromatous plaques and vascular calcification in vivo.

Treatment of Sjögren's Syndrome

Sjögren's syndrome is an autoimmune disorder in which immune cells attack and destroy the glands that produce tears and saliva. Sjögren's syndrome is considered a rheumatic disorder, meaning it causes inflammation in the joints, muscles, skin and/or other organs. The hallmark symptoms of the disorder are dry mouth and dry eyes. Sjögren's syndrome may also cause skin, nose and vaginal dryness, and can affect other organs of the body including the kidneys, blood vessels, lungs, liver, pancreas and brain. Sjögren's syndrome affects 1-4 million people in the United States, and is currently the second most common autoimmune rheumatic disease in the United States. The majority of Sjögren's sufferers are at least 40 years old at the time of diagnosis, and women are nine times more likely to develop the disease. Sjögren's syndrome can occur as a primary rheumatic condition or as a secondary disorder in association with other rheumatic diseases, such as systemic lupus erythematosus ("lupus"), scleroderma biliary cirrhosis or rheumatoid arthritis.

Sjögren's syndrome can damage vital organs of the body with symptoms that may remain stable, worsen, or go into remission. Some patients experience only the mild symptoms of dry eyes and mouth, while others go through cycles of good health followed by severe disease. While many patients are able to treat problems symptomatically, others suffer from blurred vision, constant eye discomfort, recurrent mouth infections, swollen parotid glands, hoarseness, and difficulty in swallowing and eating. Debilitating fatigue and joint pain can seriously impair quality of life.

There is currently no known cure for Sjögren's syndrome, nor is there a specific treatment to restore gland secretion. Treatment is generally symptomatic and supportive, including moisture replacement therapies to relieve the symptoms of eye and mouth dryness. Non-steroidal anti-inflammatory drugs can be used to treat musculoskeletal symptoms. For individuals with severe complications, corticosteroids or immunosuppressive drugs are often prescribed. These drugs can have serious side effects. Moreover, diagnosis of the disease is currently based on a combination of indications, such as objective and subjective dryness, autoantibodies, and mononuclear infiltrates and is primarily a process of elimination of other known diseases to arrive at the diagnosis of Sjögren's syndrome. Therefore, a need exists to not only accurately diagnose patients with Sjögren's syndrome, but to identify viable therapeutic targets for treatment of the disease.

Bone morphogenetic protein 6 (BMP6) is a member of the TGF-β superfamily of growth factors. Expression of BMP6 has been detected in several different mammalian tissues and cell types, including smooth muscle cells, growth plate chondrocytes, bronchiolar epithelium, cornea, epidermis, salivary gland and cells of the nervous system (Blessing et al., *J Cell Biol* 135(1):227-239, 1996). In vitro, BMP6 has been shown to inhibit cell division, promote terminal epithelial differentiation, and induce endochondral bone formation, osteoblastic differentiation and neuronal maturation (Heikinheimo et al., *Cancer Res* 59:5815-5821, 1999).

DNA methylation is the major modification of eukaryotic genomes and plays an essential role in mammalian development. The human proteins MECP2, MBD1, MBD2, MBD3, and MBD4 comprise a family of nuclear proteins related by the presence in each of a methyl-CpG binding domain (MBD). Each of these proteins, with the exception of MBD3, is capable of binding specifically to methylated DNA. MECP2, MBD1 and MBD2 can also repress transcription from methylated gene promoters. In contrast to other MBD family members, MECP2 is X-linked and subject to X inactivation.

X inactivation is an early developmental process in mammalian females that transcriptionally silences one of the pair of X chromosomes, thus providing dosage equivalence between males and females. The process is regulated by several factors, including a region of chromosome X called the X inactivation center (XIC). The XIST gene (X (inactive)-specific transcript (non-protein coding)) is expressed exclusively from the XIC of the inactive X chromosome. The transcript is spliced but does not encode a protein. The transcript remains in the nucleus where it coats the inactive X chromosome.

Also provided herein is a method of treating a subject with Sjögren's syndrome by selecting a subject with increased BMP6 expression and administering to the subject a therapeutically effective amount of an agent that inhibits expression or activity of BMP6, wherein the agent is one or more crystalline compounds or compositions described herein. Also provided herein is a method of treating a subject with Sjögren's syndrome comprising administering to the subject a therapeutically effective amount of one or more crystalline compounds or compositions described herein, thereby treating the subject.

Male Sjögren's syndrome patients express XIST, a non-coding RNA that is typically not expressed in males. Also described is the finding that male Sjögren's syndrome patients down-regulate MECP2, as well as other proteins involved in DNA methylation. In some embodiments, the biological sample is a salivary gland, such as a minor salivary gland.

A subset of male Sjögren's syndrome patients, Y-chromosome gene expression is down-regulated, as is expression of ribosomal proteins that regulate RNA processing and viral replication, and proteins that regulate DNA methylation. These findings provide additional markers that can be utilized for the diagnosis and treatment of Sjögren's syndrome.

Further provided is a method of treating a male subject with Sjögren's syndrome by selecting a male subject with increased expression of XIST, and administering to the subject a therapeutically effective amount of an agent that inhibits expression of XIST. Also provided is a method of treating a male subject with Sjögren's syndrome by selecting a male subject with increased expression of XIST, and administering to the subject a therapeutically effective amount of one or more crystalline compounds or compositions described herein. Also provided is a method of treating a male subject with Sjögren's syndrome by selecting a male subject with decreased expression of MECP2 and administering to the subject a therapeutically effective amount of one or more crystalline compounds or compositions described herein. Also provided is a method of treating a male subject with Sjögren's syndrome comprising administering to the male subject a therapeutically effective amount of one or more crystalline compounds or compositions described herein, thereby treating the male subject.

Sjögren's syndrome patients exhibit a statistically significant increase in expression of BMP6 in salivary glands compared to healthy control subjects. Overexpression of BMP6 in the salivary gland increases electrical potential across the salivary gland. Disclosed herein is the finding that administration of an inhibitor of BMP6 signaling increases salivary flow in the salivary gland, wherein the inhibitor is one or more crystalline compounds or compositions described herein.

Provided herein are methods of increasing salivary flow in a subject. In some embodiments, the method includes administering to the subject an inhibitor of BMP6 signaling, wherein the inhibitor is one or more crystalline compounds or compositions described herein. In other embodiments, the method includes selecting a subject with increased expression of BMP6 in a salivary gland of the subject relative to a control, and administering to the subject an inhibitor of BMP6 signaling, wherein the inhibitor is one or more crystalline compounds or compositions described herein. In some cases, the subject has Sjögren's syndrome.

In some embodiments, the salivary gland exhibiting increased expression of BMP6 is a minor labial salivary gland, a parotid gland or a submandibular gland.

In some embodiments, the inhibitor of BMP6 is administered locally to the salivary gland, wherein the inhibitor is one or more crystalline compounds or compositions described herein.

In some embodiments, the inhibitor of BMP6 signaling inhibits BMP type I receptor ALK2 and/or BMP type I receptor ALK3, wherein the inhibitor is one or more crystalline compounds or compositions described herein.

In some embodiments, the biological sample is a tissue sample, such as salivary gland tissue (for example, tissue obtained by biopsy of a salivary gland). In some examples, the salivary gland is a minor labial salivary gland, parotid gland or a submandibular gland. In other embodiments, the biological sample is a bodily fluid sample, such as a saliva, tear, blood or serum sample.

In some embodiments, the disclosed methods further include providing an appropriate therapy to the subject diagnosed with Sjögren's syndrome. In some examples, the appropriate therapy comprises administering an agent that promotes salivary production (e.g., one or more crystalline compounds or compositions described herein administering a corticosteroid, administering an immunosuppressive drug, administering a non-steroidal anti-inflammatory drug, administering an agent that inhibits expression or activity of BMP6, administering an agent that inhibits BMP signaling (e.g., one or more crystalline compounds or compositions described herein, or any combination thereof.

Also provided is a method of increasing salivary flow in a subject by selecting a subject with increased expression of BMP6 in a salivary gland and administering to the subject a therapeutically effective amount of an agent that inhibits expression or activity of BMP6. In some examples, the agent is one or more crystalline compounds or compositions described herein. In some embodiments, the salivary gland is a minor labial salivary gland, parotid gland or a submandibular gland.

In some embodiments, the agent that inhibits BMP signaling is one or more crystalline compounds or compositions described herein.

In some embodiments, the agent that inhibits expression or activity of BMP6, or inhibits BMP signaling, is administered locally to the salivary gland, wherein the agent is one or more crystalline compounds or compositions described herein. In other embodiments, the agent that inhibits expression or activity of BMP6, or inhibits BMP signaling, is administered systemically, wherein the agent is one or more crystalline compounds or compositions described herein.

In some embodiments, the method further includes providing an appropriate therapy to the subject diagnosed with Sjögren's syndrome. In some examples, the appropriate therapy comprises administering an agent that promotes salivary production (e.g., one or more crystalline compounds or compositions described herein), administering a corticosteroid, administering an immunosuppressive drug, administering a non-steroidal anti-inflammatory drug, administering an agent that inhibits expression or activity of BMP6, administering an agent that inhibits BMP signaling (e.g., one or more compounds of Formula I, or any combination thereof.

In some embodiments, the disclosed methods further include providing an appropriate therapy to the male subject diagnosed with Sjögren's syndrome. In some examples, the appropriate therapy comprises administering an agent that promotes salivary production (e.g, one or more crystalline compounds or compositions described herein, administering a corticosteroid, administering an immunosuppressive drug, administering a non-steroidal anti-inflammatory drug, administering an agent that inhibits expression or activity of BMP6, administering an agent that inhibits BMP signaling (e.g, one or more crystalline compounds or compositions described herein, administering an agent that inhibits expression of XIST, administering a nucleic acid molecule encoding MECP2, or any combination thereof.

Further provided are methods of treating a male subject with Sjögren's syndrome by selecting a male subject with increased expression of XIST and/or decreased expression of MECP2, and (i) administering to the subject a therapeutically effective amount of an agent that inhibits expression of XIST, or (ii) administering to the subject a therapeutically effective amount of nucleic acid molecule encoding MECP2, or both (i) and (ii).

Also provided are methods of increasing salivary flow in a male subject by selecting a subject with increased expression of XIST and/or decreased expression of MECP2, and administering to the subject (i) a therapeutically effective amount of an agent that inhibits expression of XIST, or (ii) a therapeutically effective amount of a nucleic acid molecule encoding MECP2 (such as a vector encoding MECP2), or both (i) and (ii).

Exemplary XIST inhibitors include, for example, antisense oligonucleotides or siRNA molecules that specifically hybridize with a XIST nucleic acid molecule. XIST nucleic acid sequences are publically available, such as the human XIST RNA sequence deposited under GenBank™ Accession No. NR-001564. Appropriate antisense oligonucleotides or siRNAs targeting XIST can be designed by one of skill in the art using publically available XIST sequences. The XIST antisense transcript Tsix is a known inhibitor of XIST (Senner and Brockdorff, *Curr Opin Genet Dev* 19(2):122-126, 2009; Stavropoulos et al., *Proc Natl Acad Sci USA* 98(18):10232-10237, 2001) that can be used with the disclosed methods.

As described herein, significant alterations in sex-chromosome gene expression were identified in male SS patients, including XIST expression, decreased MECP2 expression and apparent silencing of Y-chromosome gene expression. This gene expression pattern, called Autoimmune Xist Y-chromosome Inactivation Syndrome (AXYIS), was also identified in affected tissues from males diagnosed with autoimmune diseases associated with pSS, including rheumatoid arthritis, type II diabetes mellitus, systemic sclerosis and lymphoma.

In particular, described herein is the finding that in a subset of male Sjögren's syndrome patients, Y-chromosome gene expression is down-regulated (for example, expression of the genes RPS4Y1, RPS4Y2, JAR1D1D, CYORF15B and CYORF14 is down-regulated), as is expression of ribosomal proteins that regulate RNA processing and viral replication (e.g., RPS4Y1, RPS4Y2 and RPS4X), and proteins that regulate DNA methylation (such as MDB6 and NASP). In addition, a significant number of duplications and/or deletions were identified in the opsin (OPN1LW, OPN1MW and OPN1MW2) and tex28 region of the X-chromosomes of male patients with Sjögren's syndrome. These findings provide additional markers that can be utilized for the diagnosis and treatment of Sjögren's syndrome in men.

Provided herein are methods of treating Sjögren's syndrome in a subject in need of treatment (such as a subject with increased expression of BMP6 in a salivary gland), by administering to the subject an agent that inhibits BMP6, such as a compound that inhibits expression (mRNA or protein expression) or at least one biological activity of BMP6, wherein the agent or compound is one or more crystalline compounds or compositions described herein. The agent or compound can also be an agent or compound that inhibits BMP signaling, such as one or more crystalline compounds or compositions described herein.

In various embodiments, the present invention provides a method of treating a subject with Sjogren's syndrome, or a method of increasing salivary flow in a subject comprising selecting a subject with increased expression of BMP6 in a salivary gland of the subject relative to a control, and administering to the subject a therapeutically effective amount of an agent that inhibits expression or activity of BMP6, or an agent that inhibits BMP signaling, thereby treating the subject with Sjogren's syndrome, or increasing salivary flow in the subject, wherein the agent is one or more crystalline compounds or compositions described herein. In some embodiments, the salivary gland is a minor labial salivary gland, parotid gland or a submandibular gland. In some embodiments, the agent that inhibits expression or activity of BMP6 is one or more crystalline compounds or compositions described herein.

Treatment of Diffuse Intrinsic Pontine Glioma (DIPG)

Diffuse Intrinsic Pontine Glioma (DIPG) (also known as diffuse intrinsic pontine glioma) is a tumor located in the pons (middle) of the brain stem. The brain stem is the bottommost portion of the brain, connecting the cerebrum with the spinal cord. Diffuse Intrinsic Pontine Glioma has been associated with the same gain of function mutations in ACVR1 as fibrodysplasia ossificans progressiva.

In various embodiments, the present invention provides a method for treating a subject with diffuse intrinsic pontine glioma (DIPG), comprising selecting the subject with diffuse intrinsic pontine glioma (DIPG), and administering to the subject a therapeutically effective amount of one or more crystalline compounds or compositions described herein, thereby treating the subject with diffuse intrinsic pontine glioma (DIPG).

Propagation, Engraftment and Differentiation of Progenitor Cells Including Embryonic and Adult Stem Cells In vitro and In vivo BMP signals are important for regulating the differentiation and regeneration of precursor and stem cell populations, in some contexts and tissues preventing (while in other contexts directing) differentiation towards a lineage. Treatment with one or more crystalline compounds or compositions described herein as described herein can be used to (i) maintain a pluripotential state in stem cell or multipotent cell populations in vivo or in vitro; (ii) expand stem cell or multipotent cell populations in vivo or in vitro; (iii) direct differentiation of stem cell or multipotent cell populations in vivo or in vitro; (iv) manipulate or direct the differentiation of stem cell or multipotent cell populations in vivo or in vitro, either alone or in combination or in sequence with other treatments; and (v) modulate the de-differentiation of differentiated cell populations into multipotent or progenitor populations.

Numerous stem cell and precursor lineages require BMP signals in order to determine whether they will expand, differentiate towards specific tissue lineages, home in and integrate with particular tissue types, or undergo programmed cell death. Frequently BMP signals interact with signals provided by growth factors (bFGF, PDGF, VEGF, HBEGF, PIGF, and others), Sonic Hedgehog (SHH), notch, and Wnt signaling pathways to effect these changes (Okita et al. Curr. Stem Cell Res. Ther. 1:103-111, 2006). Treatment with one or more crystalline compounds or compositions described herein as described herein can be used to direct the differentiation of stem cells (e.g., embryonic stem cells) or tissue progenitor cells towards specific lineages for therapeutic application (Park et al. Development 131:2749-2762, 2004; Pashmforoush et al. Cell 117:373-386, 2004). Alternatively for certain cell populations, BMP inhibitors as described herein may be effective in preventing differentiation and promoting expansion, in order to produce sufficient numbers of cells to be effective for a clinical application. The exact dose and/or combination of one or more crystalline compounds or compositions described herein and other BMP antagonists or growth factor(s) or signaling molecule (s) may be highly specific to each cell and tissue type.

For example, certain embryonic stem cell lines require co-culture with leukemia inhibitory factor (LIF) to inhibit differentiation and maintain the pluripotency of certain cultured embryonic stem cell lines (Okita et al. Curr. Stein Cell Res. Ther. 1:103-111, 2006). Use of one or more crystalline compounds or compositions described herein as described herein may be used to maintain pluripotency in the absence of LIF. Other ES cell lines require coculture with a specific feeder cell layer in order to maintain pluripotency. Use of one or more crystalline compounds or compositions described herein as described herein, alone or in combination with other agents, may be effective in maintaining pluripotency when concerns of contamination with a feeder cell layer, or its DNA or protein components would complicate or prevent use of cells for human therapy.

In another example, in some circumstances antagonizing BMP signals with a protein such as noggin shortly before cessation of LIF in culture is able to induce differentiation into a cardiomyocyte lineage (Yuasa et al. Nat. Biotechnol. 23:607-611, 2005). Use of a pharmacologic BMP antagonist, such as one or more crystalline compounds or compositions described herein as described herein may achieve similar if not more potent effects. Such differentiated cells could be introduced into diseased myocardium therapeutically. Alternatively, such treatment may actually be more effective on engrafted precursor cells which have already homed in to diseased myocardium. Systemic therapy with a protein antagonist of BMP such as noggin would be prohibitively expensive and entail complicated dosing. Delivery of a BMP antagonist as described herein, systemically or locally, could bias the differentiation of such precursor cells into functioning cardiomyocytes in situ.

Applications of Compounds in Mammals

Pharmaceutical compositions comprising one or more crystalline compounds or compositions described herein as described herein can be used to treat subjects (e.g., humans, domestic pets, livestock, or other animals) by use of dosages and administration regimens that are determined to be appropriate by those of skill in the art, and these parameters can vary depending on, for example, the type and extent of the disorder treated, the overall health status of the subject, the therapeutic index of the compound, and the route of administration. Standard clinical trials can be used to optimize the dose and dosing frequency for any particular pharmaceutical composition comprising one or more crystalline compounds or compositions described herein as described herein. Exemplary routes of administration that can be used include oral, parenteral, intravenous, intra-arterial, subcutaneous, intramuscular, topical, intracranial, intraorbital, ophthalmic, intraventricular, intracapsular, intraspinal, intracisternal, intraperitoneal, intranasal, aerosol, or administration by suppository. Methods for making formulations that can be used with the methods and compositions described herein are well known in the art and can be found, for example, in Remington: The Science and Practice of Pharmacy (20th edition, Ed., A. R. Gennaro), Lippincott Williams & Wilkins, 2000.

Inhibition of BMP Signaling in Insects

One or more crystalline compounds or compositions described herein may have activity against, and perhaps even selectivity for the BMP receptors of arthropods versus those of chordates. Inhibiting BMP signaling in arthropod larvae or eggs is likely to cause severe developmental abnormalities and perhaps compromise their ability to reproduce, e.g., via the same dorsalization that is observed in zebrafish and *drosophila* when this pathway is inhibited. BMP antagonists having very strong selectivity for arthropod BMP receptors versus those of humans can be used as insecticides or pest control agents that are demonstrably less toxic or more environmentally sound than current strategies Ex Vivo Applications In addition to being administered to patients in therapeutic methods, one or more crystalline compounds or compositions described herein as described herein can also be used to treat cells and tissues, as well as structural materials to be implanted into patients (see above), ex vivo. For example, the one or more crystalline compounds or compositions described herein can be used to treat explanted tissues that may be used, for example, in transplantation.

Treatment of Hypercholesterolemia or Hyperlipoproteinemia

Treatment with small molecule or recombinant BMP inhibitors reduces vascular inflammation (via macrophage accumulation and cathepsin activity), atheroma formation, and vascular calcification in mice deficient in low-density lipoprotein receptor (LDLR$^{-/-}$). Without wishing to be bound by theory, as potential explanations for impact on vascular inflammation, oxidized LDL (oxLDL) has been found to increase BMP2 expression and induce the production of reactive oxygen species (ROS) in human aortic endothelial cells. ROS production induced by oxLDL appears to require BMP signaling, based on inhibition by small molecule or recombinant BMP inhibitors. Treatment with small molecule BMP inhibitors reduces plasma low-density lipoprotein levels without inhibiting HMG-CoA reductase activity, suggesting a role of BMP signaling in the regulation of LDL cholesterol biosynthesis. Small molecule BMP inhibitors have also been found to inhibit hepatosteatosis seen in LDLR-deficient mice fed a high-fat diet. Small molecule or recombinant BMP inhibitors inhibit the synthesis of ApoB-100 in hepatoma cells in vitro. These findings implicate BMP signaling in vascular calcification and atherogenesis and provide at least two novel mechanisms by which BMP signaling may contribute to the pathogenesis of atherosclerosis. These studies highlight the BMP signaling pathway as a therapeutic target in the treatment of atherosclerosis while identifying several novel functions of BMP signaling in the regulation of vascular oxidative stress, inflammation and lipid metabolism.

In various embodiments, one or more crystalline compounds or compositions described herein as described herein may be used for the reduction of circulating levels of ApoB-100 in patients. In various embodiments, one or more crystalline compounds or compositions described herein as described herein may be used for the reduction of circulating levels of LDL in patients. In various embodiments, one or more crystalline compounds or compositions described herein as described herein may be used for the treatment of hypercholesterolemia, hyperlipidemia, or hyperlipoproteinemia, including congenital or acquired hypercholesterolemia, hyperlipidemia, or hyperlipoproteinemia. In some embodiments, the congenital hypercholesterolemia, hyperlipidemia, or hyperlipoproteinemia is autosomal dominant hypercholesterolemia (ADH), familial hypercholesterolemia (FH), polygenic hypercholesterolemia, familial combined hyperlipidemia (FCHL), hyperapobetalipoproteinemia, or small dense LDL syndrome (LDL phenotype B).

In some embodiments, the acquired hypercholesterolemia, hyperlipidemia, or hyperlipoproteinemia is associated with diabetes mellitus, hyperlipidemic diet and/or sedentary lifestyle, obesity, metabolic syndrome, intrinsic or secondary liver disease, primary biliary cirrhosis or other bile stasis disorders, alcoholism, pancreatitis, nephrotic syndrome, endstage renal disease, hypothyroidism, iatrogenesis due to administration of thiazides, beta-blockers, retinoids, highly active antiretroviral agents, estrogen, progestins, or glucocorticoids. In various embodiments, one or more crystalline compounds or compositions described herein as described herein may be used for the treatment of diseases, disorders, or syndromes associated with defects in lipid absorption or metabolism, such as sitosterolemia, cerebrotendinous xanthomatosis, or familial hypobetalipoproteinemia.

In various embodiments, one or more crystalline compounds or compositions described herein as described herein may be used for the treatment of diseases, disorders, or syndromes caused by hyperlipidemia, such as coronary artery disease and its manifestations (e.g., myocardial infarction; angina pectoris; acute coronary artery syndromes, such as unstable angina pectoris; cardiac dysfunction, such as congestive heart failure, caused by myocardial infarction; or cardiac arrhythmia associated with myocardial ischemia/infarction), stroke due to occlusion of arteries supplying portions of the brain, cerebral hemorrhage, peripheral arterial disease (e.g., mesenteric ischemia; renal artery stenosis; limb ischemia and claudication; subclavian steal syndrome; abdominal aortic aneurysm; thoracic aortic aneurysm, pseudoaneurysm, intramural hematoma; or penetrating aortic ulcer, aortic dissection, aortic stenosis, vascular calcification, xanthoma, such as xanthoma affecting tendons or scleral and cutaneous xanthomas, xanthelasma, or hepatosteatosis.

In various embodiments, one or more crystalline compounds or compositions described herein or combination thereof as described herein may be used for the treatment of the foregoing diseases, disorders, or syndromes regardless of circulating lipid levels, such as in individuals exhibiting normal circulating lipid levels or metabolism.

In various embodiments, one or more crystalline compounds or compositions described herein as described herein may be used for the reduction of secondary cardiovascular events arising from coronary, cerebral, or peripheral vascular disease. In various embodiments, one or more crystalline compounds or compositions described herein as described herein may be used to treat individuals regardless of lipid levels, such as used in the treatment of individuals exhibiting normal circulating cholesterol and lipid levels. In various embodiments, one or more crystalline compounds or compositions described herein as described herein may be administered conjointly with a HMG-CoA reductase inhibitor.

In various embodiments, one or more crystalline compounds or compositions described herein as described herein may be used for the prevention of cardiovascular disease, such as in individuals with elevated markers of cardiovascular risk (e.g., C-reactive protein) or, for example, an elevated Framingham Risk Score. In various embodiments, one or more crystalline compounds or compositions described herein as described herein as described herein may be used to prevent cardiovascular disease in individuals exhibiting normal circulating cholesterol and lipid levels.

In various embodiments, one or more crystalline compounds or compositions described herein as described herein are used in the treatment or prevention of the foregoing diseases, disorders, or syndromes, the patient being treated is not diagnosed with and/or is not suffering from one or more of the following conditions: vascular inflammation associated with atherosclerosis, autoimmune disease, and other vasculitis; atherosclerotic disease, atheromatous plaques, and/or vascular calcification; an aneurysm and/or aneurysm formation; acute coronary syndromes (angina pectoris and heart attack), transient ischemic attacks, stroke, peripheral vascular disease, or other vascular ischemic events.

In various embodiments, one or more crystalline compounds or compositions described herein as described herein are used in the treatment or prevention of the foregoing diseases, disorders, or syndromes (e.g., for the reduction of circulating levels of ApoB-100 and/or LDL in patients; for the treatment of hypercholesterolemia, hyperlipidemia, or hyperlipoproteinemia, including congenital or acquired hypercholesterolemia, hyperlipidemia, or hyperlipoproteinemia; for the treatment of diseases, disorders, or syndromes associated with defects in lipid absorption or metabolism; for the treatment of diseases, disorders, or syndromes caused by hyperlipidemia; for the reduction of secondary cardiovascular events arising from coronary, cerebral, or peripheral vascular disease; or for the reduction of secondary cardiovascular events arising from coronary, cerebral, or peripheral vascular disease), the patient being treated is also diagnosed with and/or is also suffering from one or more of the following conditions: vascular inflammation associated with atherosclerosis, autoimmune disease, and other vasculitis; atherosclerotic disease, atheromatous plaques, and/or vascular calcification; an aneurysm and/or aneurysm formation; acute coronary syndromes (angina pectoris and heart attack), transient ischemic attacks, stroke, peripheral vascular disease, or other vascular ischemic events T. Treatment of Cartilage Defects The selective inhibition of specific BMP receptors enables cartilage formation by preventing calcification and mineralization of scaffolds produced by mesenchymal stem cells (Hellingman et al. Tissue Eng Part A. 2011 April; 17(7-8): 1157-67. Epub 2011 Jan. 17.) Accordingly, in some embodiments compounds of the invention as described herein may be useful to promote cartilage repair/regeneration in patients with cartilage injuries or defects, as well as in the ex vivo or in vitro production of cartilage tissue, e.g., for implantation, from appropriate cells, such as mesenchymal stem cells.

U. Application of Compounds with Varying Degrees of Selectivity: Compounds which
inhibit BMP signaling via particular BMP type I receptors, or compounds which also affect signaling via TGF-β, Activin, AMP kinase, or VEGF receptors.

In various embodiments several of the compounds of the present invention described herein will have relative greater selectivity for particular BMP type I receptors. The pathogenesis of certain diseases might be attributed to the dysfunctional signaling of one particular receptor. For example, fibrodysplasia ossificans progressiva is a disease caused by aberrant (constitutively active) ALK2 function (Yu et al. Nat. Chem. Biol. 4:33-41, 2008). In such instances, in various embodiments compounds of the present invention as described herein which specifically antagonize the function of a subset of the BMP type I receptors may have the advantage of reduced toxicity or side effects, or greater effectiveness, or both.

In some embodiments compounds of the invention as described herein may have a high degree of selectivity for BMP vs. TGF-β, Activin, AMP kinase, and VEGF receptor signaling. Other compounds may be less specific and may target other pathways in addition to BMP signaling. In the treatment of tumors, for example, agents which inhibit BMP signaling as well as one or more of the above pathways can have beneficial effects (e.g., decrease tumor size), when molecular phenotyping of specific patients' tumors reveals dysregulation of multiple pathways.

In some embodiments compounds of the invention as described herein (e.g., one or more crystalline compounds or compositions described herein have a high degree of selectivity for ALK2 versus ALK1 or ALK3 or ALK4 or ALK5 or ALK6. Selective inhibition of ALK2 versus ALK1 or ALK3 or ALK4 or ALK5 or ALK6 may minimize unwanted effects or toxicity. Chronic ALK3 inhibition might impair normal mucosal epithelial turnover due to known importance in intestinal crypt stem cell recycling, and implication of ALK3 function in juvenile familial polyposis. ALK1 inhibition might impair normal vascular remodeling and lead to complications similar to human hereditary telangiectasia syndrome type 2 (HHT2), such as leaky capillaries, AV malformations, and bleeding. Accordingly, compounds that selectively inhibit ALK2 relative to ALK3 and ALK1 may help avoid toxicities of this type that might be encountered through the use of an unselective inhibitor.

In certain embodiments, the invention provides a method of inhibiting the activity of ALK2 in a human, comprising administering to the human one or more crystalline compounds or compositions described herein that selectively inhibits the activity of human ALK2 relative to the activity of human ALK1. In some such embodiments, the one or more crystalline compounds or compositions described herein inhibits the activity of human ALK2 with an $IC_{50}$ that is lower by a factor of about 2 than its $IC_{50}$ for inhibiting the activity of human ALK1. In some such embodiments, the one or more crystalline compounds or compositions described herein inhibits the activity of human ALK2 with an $IC_{50}$ that is lower by a factor of 5 than its $IC_{50}$ for inhibiting the activity of human ALK1. In some such embodiments, the one or more crystalline compounds or compositions described herein inhibits the activity of human ALK2 with an $IC_{50}$ that is lower by a factor of 10 than its $IC_{50}$ for inhibiting the activity of human ALK1. In some such embodiments, the one or more crystalline compounds or compositions described herein inhibits the activity of human ALK2 with an $IC_{50}$ that is lower by a factor of 15 or 20 or 30 or 40 or 50 or 100 or 200 or 300 or 400 or 500 or 600 or 800 or 1000 or 1500 or 2000 or 5000 or 10000 or 15,000 or 20,000 or 40,000 or 50,000 or 60,000 or 70,000 or 80,000 or 90,000 or 100,000 than its $IC_{50}$ for inhibiting the activity of human ALK1.

In certain embodiments, the invention provides a method of inhibiting the activity of ALK2 in a human, comprising administering to the human one or more crystalline compounds or compositions described herein that selectively inhibits the activity of human ALK2 relative to the activity of human ALK3. In some such embodiments, the one or more crystalline compounds or compositions described herein inhibits the activity of human ALK2 with an $IC_{50}$ that is lower by a factor of 15 than its $IC_{50}$ for inhibiting the activity of human ALK3. In some such embodiments, the one or more crystalline compounds or compositions described herein inhibits the activity of human ALK2 with an $IC_{50}$ that is lower by a factor of 20 than its $IC_{50}$ for inhibiting the activity of human ALK3. In some such embodiments, the one or more crystalline compounds or compositions described herein inhibits the activity of human ALK2 with an $IC_{50}$ that is lower by a factor of 30 than its $IC_{50}$ for inhibiting the activity of human ALK3. In some such embodiments, the one or more crystalline compounds or compositions described herein inhibits the activity of human ALK2 with an $IC_{50}$ that is lower by a factor of 50 or 100 or 200 or 300 or 400 or 500 or 600 or 800 or 1000 or 1500 or 2000 or 5000 or 10000 or 15,000 or 20,000 or 40,000 or 60,000 or 70,000 or 80,000 or 90,000 or 100,000 than its $IC_{50}$ for inhibiting the activity of human ALK3.

In certain embodiments, the invention provides a method of inhibiting the activity of ALK2 in a human, comprising administering to the human one or more crystalline compounds or compositions described herein that selectively inhibits the activity of human ALK2 relative to the activity of human ALK4. In some such embodiments, the one or more crystalline compounds or compositions described herein inhibits the activity of human ALK2 with an $IC_{50}$ that is lower by a factor of 1000 than its $IC_{50}$ for inhibiting the activity of human ALK4. In some such embodiments, the one or more crystalline compounds or compositions described herein inhibits the activity of human ALK2 with an $IC_{50}$ that is lower by a factor of 2000 than its $IC_{50}$ for inhibiting the activity of human ALK4. In some such embodiments, the one or more crystalline compounds or compositions described herein inhibits the activity of human ALK2 with an $IC_{50}$ that is lower by a factor of 3000 than its $IC_{50}$ for inhibiting the activity of human ALK4. In some such embodiments, the one or more crystalline compounds or compositions described herein inhibits the activity of human ALK2 with an $IC_{50}$ that is lower by a factor of 4000 or 5000 or 6000 or 7000 or 8000 or 9000 or 10,000 or 12,000 or 14,000 or 16,000 or 18,000 or 20,000 or 25,000 or 30,000 or 40,000 or 50,000 or 60,000 or 70,000 or 80,000 or 90,000 or 100,000 than its $IC_{50}$ for inhibiting the activity of human ALK4.

In certain embodiments, the invention provides a method of inhibiting the activity of ALK2 in a human, comprising administering to the human one or more crystalline compounds or compositions described herein that selectively inhibits the activity of human ALK2 relative to the activity of human ALK6. In some such embodiments, the one or more crystalline compounds or compositions described herein inhibits the activity of human ALK2 with an $IC_{50}$ that is lower by a factor of 2 than its $IC_{50}$ for inhibiting the activity of human ALK6. In some such embodiments, the one or more crystalline compounds or compositions described herein inhibits the activity of human ALK2 with an $IC_{50}$ that is lower by a factor of 5 than its $IC_{50}$ for inhibiting the activity of human ALK6. In some such embodiments, the one or more crystalline compounds or compositions described herein inhibits the activity of human ALK2 with an $IC_{50}$ that is lower by a factor of 10 than its $IC_{50}$ for inhibiting the activity of human ALK6. In some such embodiments, the one or more crystalline compounds or compositions described herein inhibits the activity of human ALK2 with an $IC_{50}$ that is lower by a factor of 15 or 20 or 30 or 40 or 50 or 100 or 200 or 300 or 400 or 500 or 600 or 800 or 1000 or 1500 or 2000 or 5000 or 10000 or 15,000 or 20,000 or 40,000 or 50,000 or 60,000 or 70,000 or 80,000 or 90,000 or 100,000 than its $IC_{50}$ for inhibiting the activity of human ALK6 In one aspect, the invention provides a method of inhibiting the activity of ALK2 in a human, comprising administering to the human one or more crystalline compounds or compositions described herein that selectively inhibits the activity of human ALK2 relative to the activity of human ALK5. In some such embodiments, the one or more crystalline compounds or compositions described herein inhibits the activity of human ALK2 with an $IC_{50}$ that is lower by a factor of 1000 than its $IC_{50}$ for inhibiting the activity of human ALK5. In some such embodiments, the one or more crystalline compounds or compositions described herein inhibits the activity of human ALK2 with an $IC_{50}$ that is lower by a factor of 2000 than its $IC_{50}$ for inhibiting the activity of human ALK5. In some such embodiments, the one or more crystalline compounds or compositions described herein inhibits the activity of human ALK2 with an $IC_{50}$ that is lower by a factor of 3000 than its $IC_{50}$ for inhibiting the activity of human ALK5. In some such embodiments, the one or more crystalline compounds or compositions described herein inhibits the activity of human ALK2 with an $IC_{50}$ that is lower by a factor of 4000 or 5000 or 6000 or 7000 or 8000 or 9000 or 10,000 or 12,000 or 14,000 or 16,000 or 18,000 or 20,000 or 25,000 or 30,000 or 40,000 or 50,000 or 60,000 or 70,000 or 80,000 or 90,000 or 100,000 than its $IC_{50}$ for inhibiting the activity of human ALK5.

As used herein, a therapeutic that "prevents" a disorder or condition refers to a compound that, in a statistical sample, reduces the occurrence or frequency of the disorder or condition in the treated sample relative to an untreated control sample, or delays the onset or reduces the severity of one or more symptoms of the disorder or condition relative to the untreated control sample. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

Combination Therapies

In certain instances one or more crystalline compounds or compositions described herein as described herein can be used in combination with other current or future drug therapies, because the effects of inhibiting BMP alone may be less optimal by itself, and/or can be synergistic or more highly effective in combination with therapies acting on distinct pathways which interact functionally with BMP signaling, or on the BMP pathway itself. In certain instances, conjoint administration of a BMP inhibitor as described herein (e.g., one or more crystalline compounds or compositions described herein with an additional drug therapy reduces the dose of the additional drug therapy such that it is less than the amount that achieves a therapeutic effect when used in a monotherapy (e.g., in the absence of a BMP inhibitor as described herein).

Some non-limiting examples of combination therapies could include the following.

Coadministration of erythropoietin (Epogen) and BMP antagonists as described herein may be especially effective for certain types of anemia of inflammation, as described above, particularly in diseases such as end-stage renal disease in which chronic inflammation and erythropoietin insufficiency both act to promote anemia.

In certain embodiments, BMP inhibitors as described herein (e.g., one or more crystalline compounds or compositions described herein may be administered conjointly with other antihyperlipidemic agents or antilipidemic agents including, but not limited to, HMG-CoA reductase inhibitors (e.g., atorvastatin, cerivastatin, fluvastatin, lovastatin, mevastatin, pitavastain, pravastatin, rosuvastatin, or simvastatin), fibrates (e.g., bezafibrate, ciprofibrate, clofibrate, gemfibrozil, or fenofibrate), ezetimibe, niacin, cholesteryl ester transfer protein (CETP) inhibitors (e.g., torcetrapib, anacetrapib, or dalcetrapib), cholestyramine, colestipol, probucol, dextrothyroxine, bile acid sequestrants, or combinations of the above.

In certain embodiments, BMP inhibitors as described herein (e.g., one or more crystalline compounds or compositions described herein may be administered conjointly with a treatment for diabetes including, but not limited to, sulfonyl ureas (e.g., chlorpropamide, tolbutamide, glyburide, glipizide, or glimepiride), medications that decrease the amount of glucose produced by the liver (e.g., metformin), meglitinides (e.g., repaglinide or nateglinide), medications that decrease the absorption of carbohydrates from the intestine (e.g., alpha glucosidase inhibitors such as acarbose), medications that effect glycemic control (e.g., pramlintide or exenatide), DPP-IV inhibitors (e.g., sitagliptin), insulin treatment, thiazolidinones (e.g., troglitazone, ciglitazone, pioglitazone, or rosiglitazone), oxadiazolidinediones, alpha-glucosidase inhibitors (e.g., miglitol or acarbose), agents acting on the ATP-dependent postassium channel of the beta cells (e.g., tolbutamide, glibenclamide, glipizide, glicazide, or repaglinide), nateglinide, glucagon inhibitors, inhibitors of hepatic enzymes involved in stimulation of gluconeogenesis and/or glycogenolysis, or combinations of the above.

In certain embodiments, BMP inhibitors as described herein (e.g., one or more crystalline compounds or compositions described herein may be administered conjointly with a treatment for obesity including, but not limited to, orlistat, sibutramine, phendimetrazine, phentermine, diethylpropion, benzphetamine, mazindol, dextroamphetamine, rimonabant, cetilistat, GT 389-255, APD356, pramlintide/AC137, PYY3-36, AC 162352/PYY3-36, oxyntomodulin, TM 30338, AOD 9604, oleoyl-estrone, bromocriptine, ephedrine, leptin, pseudoephedrine, or pharmaceutically acceptable salts thereof, or combinations of the above.

In certain embodiments, BMP inhibitors as described herein (e.g., one or more crystalline compounds or compositions described herein may be administered conjointly with an antihypertensive agent including, but not limited to, beta-blockers (e.g., alprenolol, atenolol, timolol, pindolol propranolol and metoprolol), ACE (angiotensin converting enzyme) inhibitors (e.g., benazepril, captopril, enalapril, fosinopril, lisinopril, quinapril and ramipril), calcium channel blockers (e.g., nifedipine, felodipine, nicardipine, isradipine, nimodipine, diltiazem and verapamil), and alpha-blockers (e.g., doxazosin, urapidil, prazosin and terazosin), or combinations of the above. In certain embodiments, BMP inhibitors as described herein may be administered conjointly with a treatment for anemia (e.g., anemia of inflammation associated with renal failure and hemodialysis), including but not limited to erythopoiesis-stimulating agents (e.g. erythropoietin).

Tyrosine kinase receptor inhibitors, such as SU-5416, and BMP inhibitors as described herein (e.g., one or more of a compound of) may have synergistic effects at inhibiting angiogenesis, particularly for anti-angiogenic therapy against tumors. BMP signals (BMP-4) are thought to be critical for the commitment of stem or precursor cells to a hematopoietic/endothelial common progenitor, and may promote the proliferation, survival, and migration of mature endothelial cells necessary for angiogenesis (Park et al. Development 131:2749-2762, 2004). Thus antagonism of BMP signals using compounds as described herein may provide additional inhibition of angiogenesis at the level of endothelial precursors and cells. Similarly, co-treatment with BMP inhibitors as described herein (e.g., one or more crystalline compounds or compositions described herein and other tyrosine kinase receptor inhibitors such as imatinib (Gleevec) could be used to inhibit vascular remodeling and angiogenesis of certain tumors.

The combination of a sonic hedgehog agonist and a BMP inhibitor as described herein (e.g., one or more crystalline compounds or compositions described herein may be particularly useful for promoting hair growth, as SHH activity is known to stimulate the transition of follicles out of telogen (resting) phase (Paladini et al. J. Invest. Dermatol. 125:638-646, 2005), while inhibiting the BMP pathway shortens the telogen phase (Plikus et al. Nature 451:340-344, 2008). The use of both would be expected to cause relatively increased time in the anagen or growth phase.

Combined use of Notch modulators (e.g., gamma-secretase inhibitors) and BMP antagonists as described herein (e.g., one or more crystalline compounds or compositions described herein may be more effective than either agent alone in applications designed to inhibit bone differentiation, because increasing evidence suggests both pathways function cooperatively to effect cell differentiation (Kluppel et al. Bioessays 27:115-118, 2005). These therapies may be synergistic in the treatment of tumors in which one or both pathways is deranged (Katoh, Stem Cell Rev. 3:30-38, 2007).

Combined use of an Indian Hedgehog (IHH) antagonist and a BMP antagonist (e.g., one or more crystalline compounds or compositions described herein as described herein may inhibit pathologic bone formation. IHH is responsible for the commitment of bone precursors to chondrocyte or cartilage forming cells. Endochondral bone formation involves coordinated activity of both chondrogenesis (promoted by BMP signals and IHH signals) and their subsequent calcification by mineralization programs initiated by BMP signals (Seki et al. J. Biol. Chem. 279:18544-18549, 2004; Minina et al. Development 128:4523-4534, 2001). Coadministration of an IHH antagonist with one or more crystalline compounds or compositions described herein as described herein, therefore, may be more effective in inhibiting pathological bone growth due to hyperactive BMP signaling (such as in FOP), or in any of the inflammatory or traumatic disorders of pathologic bone formation described above.

Strong experimental evidence exists for an effect of both Smo antagonism and BMP antagonism for treating glioblastoma. Compounds as described herein (e.g., one or more crystalline compounds or compositions described herein may be used in combination with Smo antagonists to treat glioblastoma.

In some embodiments, one or more crystalline compounds or compositions described herein is administered in combination with an agent selected from the group consisting of: a corticosteroid, a non-steroidal anti-inflammatory drug (NSAID), a lipoxygenase inhibitor, a leukotriene inhibitor, a mast cell stabilizing agent, an anti-histamine, a tumor necrosis factor (TNF) inhibitor, an IL-23 blocker, an IL1-RA therapy, a cytotoxic therapy, a bisphosphonate, an anti-rheumatic drug, CTA4-Ig therapy, anti-growth factor therapies, and an inhibitor of interleukin-1 signaling.

Exemplary corticosteroids for use in combination with one or more crystalline compounds or compositions described herein include, but are not limited to, prednisone, cortisol, and hydrocortisone. In one embodiment, the corticosteroid is prednisone.

Exemplary NSAIDs for use in combination with one or more crystalline compounds or compositions described herein include, but are not limited to, naproxen, ibuprofen, meloxicam, diclofenac, aspirin, piroxicam, sulindac, meclofenamic acid, and indomethacin.

In some embodiments, one or more crystalline compounds or compositions described herein is administered in combination with a lipoxygenase inhibitor such as meclofenamate sodium or zileuton.

Exemplary leukotriene inhibitors for use in combination with one or more crystalline compounds or compositions described herein include e.g., montelukast, zafirlukast, and pranlukast.

Non-limiting examples of mast cell stabilizing agents for use in combination with one or more crystalline compounds or compositions described herein include, but are not limited to, cromolyn sodium, cromoglicic acid, ketotifen, olopatadine, omalizumab, pemirolast, quercetin, theophylline, caffeine, paraxanthine, aminophylline, and theobromine.

In some embodiments, one or more crystalline compounds or compositions described herein is administered in combination with an anti-histamine, for example, diphenhydramine, cetirizine, ranitidine, famotidine, chlorphenamine, chlorodiphenhydramine, and fexofenidine, among others.

Exemplary anti-tumor necrosis factor (anti-TNF) drugs contemplated for use with one or more crystalline compounds or compositions described herein include, but are not limited to, infliximab, etanercept, adalimumab, certolizumab, bupropion, and golimumab.

Exemplary inhibitors of interleukin-23 (IL-23) signaling contemplated for use with one or more crystalline compounds or compositions described herein include, but are not limited to, ustekinumab and BI-855066.

Exemplary inhibitors of interleukin-1 (IL-1) signaling or IL-1RA therapies contemplated for use with one or more crystalline compounds or compositions described herein include, but are not limited to, anakinra, canakinumab, and rilonacept.

Exemplary cytotoxic therapies for use in combination with one or more crystalline compounds or compositions described herein include, but are not limited to, methotrexate, cyclophosphamide, 5-fluorouracil, doxorubicin, vincristine, bleomycin, procarbazine, prednisilone, dacarbazine, etoposide, cisplatin, oxaliplatin, among others Exemplary bisphosphonates for use in combination with one or more crystalline compounds or compositions described herein include, but are not limited to, alendronate (FOSAMAX™), ibandronate (BONIVA™), risedronate (ACTONEL™, ATELVIA™), and zoledronic acid (RECLAST™).

Exemplary anti-growth factor therapies for use in combination with one or more crystalline compounds or compositions described herein include, but are not limited to, anti-PDGF, anti-FGF, and anti-VEGF therapies.

Exemplary disease modifying anti-rheumatic drugs for use in combination with one or more crystalline compounds or compositions described herein include, but are not limited to, azathioprine (IMURAN™), cyclophosphamide (CYTOXAN™), cyclosporine (NEORAL™) hydroxychloroquine (PLAQUENIL™), leflunomide (ARAVA™), methotrexate (RHEUMATREX™, TREXALL™), sulfasalazine (AZULFIDINE™), and tofacitinib (XELJANZ™), among others.

In further embodiments, one or more crystalline compounds or compositions described herein can be administered in combination with cyclosporine, mycophenylate mofetil, among others.

In some embodiments, one or more crystalline compounds or compositions described herein is administered in combination with at least one additional agent, wherein the at least one additional agent comprises an anti-inflammatory agent. Exemplary anti-inflammatory agents include, but are not limited to, an inhibitor of the activity of substance P; an inhibitor of the secretion of substance P; an inhibitor of the effects of substance P; an inhibitor of the activity of histamine; an inhibitor of the secretion of histamine; an inhibitor of the effects of histamine; an inhibitor of mast cell function; an inhibitor of Toll-like receptor signaling; an inhibitor of MyD88; an inhibitor of TRIF; apyrase; and an agent to catalyze hydrolysis of ATP.

In some embodiments, one or more crystalline compounds or compositions described herein is administered in combination with at least one additional agent, wherein the at least one additional agent comprises an anti-growth factor agent. Exemplary anti-growth factor agents include, but are not limited to, an inhibitor of PDGF ligands; an inhibitor of PDGF-AA; an inhibitor of PDGF-BB; an inhibitor of PDGFR-alpha receptor function; an inhibitor of PDGFR-beta receptor function; a neutralizing antibody against Activin A; a neutralizing antibody against Activin B; a neutralizing antibody against Activin A ligands; a neutralizing antibody against Activin B ligands; a neutralizing antibody against heterodimeric ligands containing Inhibin bA subunits encoded by the INHBA; a neutralizing antibody against heterodimeric ligands containing Inhibin bB subunits encoded by the INHBB gene; a ligand trap of BMP ligands; a ligand trap of Activin ligands; a ligand trap of soluble extracellular domains of a type II Activin receptor ActRIIA; a ligand trap of soluble extracellular domains of a type II Activin receptor ActRIIB; a ligand trap of soluble extracellular domains of a BMP type I receptor ALK2; a ligand trap of soluble extracellular domains of a BMP type I receptor ALK3; and a ligand trap of soluble extracellular domains of a BMP type I receptor ALK6.

In some embodiments, one or more crystalline compounds or compositions described herein is administered in combination with at least one additional agent, wherein the at least one additional agent comprises an anti-osteogenic signaling agent or an anti-chondrogenic signaling agent. Exemplary anti-osteogenic signaling agents or an anti-chondrogenic signaling agents include, but are not limited to a RAR-gamma agonist; a nonselective RAR agonist; an agent that inhibits the activity of osteogenic transcription factor Runx2; an agent that inhibits the expression of osteogenic transcription factor Runx2; an agent that promotes the degradation of osteogenic transcription factor Runx2; an agent that inhibits the activity of chondrogenic transcription factor Sox9; an agent that inhibits the expression of chondrogenic transcription factor Sox9; an agent that promotes the degradation of chondrogenic transcription factor Sox9; an inhibitor of HIF-1 alpha activity; and an inhibitor of HIF-1 alpha expression.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. In some embodiments, the additional therapeutic compound is administered within about 5 minutes to within about 168 hours prior to or after administration of the compound of Formula (I), the compound of Formula (I)I, or the compound of Formula (I)II. Thus, a subject who receives such treatment can benefit from a combined effect of different therapeutic compounds.

In certain embodiments, conjoint administration of compounds of the invention with one or more additional therapeutic agent(s) (e.g., one or more additional chemotherapeutic agent(s)) provides improved efficacy relative to each individual administration of the compound of the invention or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

When used in combination, one or more crystalline compounds or compositions described herein can be administered separately or in different formulations from at least one additional agent as described herein or can be administered in a single formulation comprising one or more crystalline compounds or compositions described herein and the additional agent. One or more crystalline compounds or compositions described herein can be administered simultaneously or concurrently with the at least one additional agent.

Administration of one or more crystalline compounds or compositions described herein can be administered using the same or different modes of administration (e.g., oral, intravenous, injection, etc). Administration of one or more crystalline compounds or compositions described herein and the at least one additional agent can occur simultaneously, within 15 min, within 30 min, or can be separated by at least one hour (e.g., at least 2, at least 3, at least 4, at least 5, at least 6, at least 7, at least 8, at least 9, at least 10, at least 11, at least 12 or more hours). One of skill in the art can easily determine an appropriate dosing regimen for a combination treatment comprising one or more crystalline compounds or compositions described herein and at least one additional agent, for example, to reduce side effects, to prevent metabolic interference from one of the agents, to enhance activity of 4 one or more crystalline compounds or compositions described herein, or to otherwise improve pharmacodynamic or pharmacokinetic factors.

It is contemplated herein that a combination of at least one additional agent as described above with one or more crystalline compounds or compositions described herein can produce a synergistic effect that is greater than the sum of the effects of each agent administered alone. In such embodiments, it is contemplated that a lower dose of one or more crystalline compounds or compositions described herein is administered in combination with a second agent than is required for a therapeutic effect when one or more crystalline compounds or compositions described herein is administered alone.

Dosage and Administration

In one aspect, the methods described herein provide a method for treating a disease or disorder comprising abnormal bone formation in a subject (e.g., a heterotopic ossification diseases). In one embodiment, the subject can be a mammal. In another embodiment, the mammal can be a human, although the approach is effective with respect to all mammals. The method comprises administering to the subject an effective amount of a pharmaceutical composition comprising one or more crystalline compounds or compositions described herein.

The dosage range for the agent depends upon the potency, and includes amounts large enough to produce the desired effect, e.g., reduction in at least one symptom of abnormal bone formation. The dosage should not be so large as to cause unacceptable adverse side effects. Generally, the dosage will vary with the type of inhibitor (e.g., an antibody or fragment, small molecule, siRNA, etc.) and with the age, condition, and sex of the patient. The dosage can be determined by one of skill in the art and can also be adjusted by the individual physician in the event of any complication. Typically, the dosage ranges from 0.1 mg/kg body weight to 1 g/kg body weight. In some embodiments, the dosage range is from 0.1 mg/kg body weight to 1 g/kg body weight, from 0.1 mg/kg body weight to 500 mg/kg body weight, from 0.1 mg/kg body weight to 250 mg/kg body weight, from 0.1 mg/kg body weight to 100 mg/kg body weight, from 0.1 mg/kg body weight to 50 mg/kg body weight, from 0.1 mg/kg body weight to 10 mg/kg body weight, from 10 mg/kg to 100 mg/kg, from 15 mg/kg to 100 mg/kg, from 20 mg/kg to 100 mg/kg, from 25 mg/kg to 100 mg/kg, from 30 mg/kg to 100 mg/kg, from 40 mg/kg to 100 mg/kg, from 50 mg/kg to 100 mg/kg, from 60 mg/kg to 100 mg/kg, from 70 mg/kg to 100 mg/kg, from 75 mg/kg to 100 mg/kg, from 25 mg/kg to 50 mg/kg, from 50 mg/kg to 200 mg/kg, from 75 mg/kg to 250 mg/kg, from 100 mg/kg to 300 mg/kg, from 100 mg/kg to 200 mg/kg, from 100 mg/kg to 400 mg/kg, from 100 mg/kg to 500 mg/kg, from 100 mg/kg to 750 mg/kg from 200 mg/kg to 1000 mg/kg, from 300 mg/kg to 1000 mg/kg, from 400 mg/kg to 1000 mg/kg, from 500 mg/kg to 1000 mg/kg, from 600 mg/kg to 1000 mg/kg, from 700 mg/kg to 1000 mg/kg, from 800 mg/kg to 1000 mg/kg, from 900 mg/kg to 1000 mg/kg, from 250 mg/kg to 750 mg/kg, from 300 mg/kg to 600 mg/kg, or any range there between.

In certain embodiments, the dose of the agent is at least 10 mg/kg/day; in other embodiments the dose of the agent is at least 20 mg/kg/day, at least 25 mg/kg/day, at least 30 mg/kg/day, at least 40 mg/kg/day, at least 50 mg/kg/day, at least 60 mg/kg/day, at least 70 mg/kg/day, at least 80 mg/kg/day, at least 90 mg/kg/day, at least 100 mg/kg/day, at least 125 mg/kg/day, at least 150 mg/kg/day, at least 175 mg/kg/day, at least 200 mg/kg/day, at least 250 mg/kg/day, at least 300 mg/kg/day, at least 400 mg/kg/day, at least 500 mg/kg/day or more.

In some embodiments, the dosage range of the agent for use in a human subject is from 10 mg/day to 250 mg/day, from at 15 mg/day to 200 mg/day, from 20 mg/day to 200 mg/day, from 25 mg/day to 200 mg/day, from 25 mg/day to 175 mg/day, from 25 mg/day to 150 mg/day, from 25 mg/day to 125 mg/day, from 25 mg/day to 100 mg/day, from 25 mg/day to 75 mg/day, from 25 mg/day to 50 mg/day, from 50 mg/day to 200 mg/day, from 75 mg/day to 200 mg/day, from 100 mg/day to 200 mg/day, from 125 mg/day to 200 mg/day, from 150 mg/day to 200 mg/day, from 175 mg/day to 200 mg/day, from 50 mg/day to 200 mg/day, from 50 mg/day to 175 mg/day, from 50 mg/day to 150 mg/day, from 50 mg/day to 100 mg/day, from 50 mg/day to 75 mg/day, from 75 mg/day to 200 mg/day, from 75 mg/day to 175 mg.day, from 75 mg/day to 150 mg/day, from 75 mg/day to 125 mg/day, from 75 mg/day to 100 mg/day, from 100 mg/day to 200 mg/day, from 100 mg/day to 175 mg/day, from 100 mg/day to 125 mg/day, from 125 mg/day to 200 mg/day, from 125 mg/day to 175 mg/day, from 125 mg/day to 150 mg/day, from 150 mg/day to 200 mg/day, from 150 mg/day to 175 mg/day, from 175 mg/day to 200 mg/day, or any range there between.

In one embodiment, the dose of one or more crystalline compounds or compositions described herein used in humans for the treatment of abnormal bone formation in soft tissue is less than the dose of one or more crystalline compounds or compositions described herein typically used in treatment of oncologic diseases and cancers.

Administration of the doses recited above can be repeated for a limited period of time. In some embodiments, the doses are given once a day, or multiple times a day, for example but not limited to three times a day. In another embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

A therapeutically effective amount is an amount of an agent that is sufficient to produce a statistically significant, measurable change in at least one symptom of a cancer (see "Efficacy Measurement" below). Such effective amounts can be gauged in clinical trials as well as animal studies for a given agent.

Agents useful in the methods and compositions described herein can be administered systemically or can be administered orally. It is also contemplated herein that the agents can also be delivered intravenously (by bolus or continuous infusion), by inhalation, intranasally, intraperitoneally, intramuscularly, subcutaneously, intracavity, and can be delivered by peristaltic means, if desired, or by other means known by those skilled in the art.

In some embodiments, the pharmaceutically acceptable formulation used to administer the active compound provides sustained delivery, such as "slow release" of the active compound to a subject. For example, the formulation can deliver the agent or composition for at least one, two, three, or four weeks after the pharmaceutically acceptable formulation is administered to the subject. Preferably, a subject to be treated in accordance with the methods described herein is treated with the active composition for at least 30 days (either by repeated administration or by use of a sustained delivery system, or both).

As used herein, the term "sustained delivery" is intended to include continual delivery of the composition in vivo over a period of time following administration, preferably at least several days, a week, several weeks, one month or longer. Sustained delivery of the active compound can be demonstrated by, for example, the continued therapeutic effect of the composition over time (such as sustained delivery of the agents can be demonstrated by continued improvement or maintained improvement in cancer symptoms in a subject).

Therapeutic compositions containing at least one agent can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as e.g., an antibody or targeted liposome technology. In some embodiments, an agent can be targeted to a tissue by using bispecific antibodies, for example produced by chemical linkage of an anti-ligand antibody (Ab) and an Ab directed toward a specific target. To avoid the limitations of chemical conjugates, molecular conjugates of antibodies can be used for production of recombinant bispecific single-chain Abs directing ligands and/or chimeric inhibitors at cell surface molecules. The addition of an antibody to an agent permits the agent to accumulate additively at the desired target site (e.g., tumor site). Antibody-based or non-antibody-based targeting moieties can be employed to deliver a ligand or the inhibitor to a target site. Preferably, a natural binding agent for an unregulated or disease associated antigen is used for this purpose.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration. Alternatively, continuous intravenous infusion sufficient to maintain concentrations in the blood or skeletal muscle tissue in the ranges specified for in vivo therapies are contemplated.

Efficacy Measurement

The efficacy of a given treatment for a disorder comprising abnormal bone growth as described herein can be determined by the skilled clinician. However, a treatment is considered "effective treatment," as the term is used herein, if any one or all of the signs or symptoms of the disease or disorder is/are altered in a beneficial manner (e.g., reduced ossification, regression of abnormal bone growths, reduced pain, increased range of motion etc.), other clinically accepted symptoms or markers of disease are improved, or even ameliorated, e.g., by at least 10% following treatment with an agent comprising one or more crystalline compounds or compositions described herein. Efficacy can also be measured by failure of an individual to worsen as assessed by stabilization of the disease or disorder, hospitalization or need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing progression of abnormal bone growth; or (2) relieving the disease, e.g., causing regression of symptoms; and (3) preventing or reducing the likelihood of the development of a disease (e.g., ossification following trauma).

An effective amount for the treatment of a disease means that amount which, when administered to a mammal in need thereof, is sufficient to result in effective treatment as that term is defined herein, for that disease. Efficacy of an agent can be determined by assessing physical indicators of abnormal bone growth, such as e.g., reduced size of abnormal bone growth, slowed deposition of abnormal bone, regression of bone growth, improvement in mobility etc.

Pharmaceutical Compositions

In certain embodiments, the present invention relates to pharmaceutical compositions comprising a crystalline compound of Formula (I) and one or more pharmaceutically acceptable excipients, as well as formulations prepared using such a crystalline compound and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for intravenous use in a human patient. In certain embodiments, the invention also relates to preparations suitable for nutraceutical, veterinary, and agriculturally-relevant uses.

Exemplary pharmaceutically acceptable excipients are presented herein, and include, for example binders, disintegrating agents, lubricants, corrigents, solubilizing agents, suspension aids, emulsifying agents, coating agents, cyclodextrins, and/or buffers. Although the dosage will vary depending on the symptoms, age and body weight of the patient, the nature and severity of the disorder to be treated or prevented, the route of administration and the form of the drug, in general, a daily dosage of from 0.01 to 3000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

In certain embodiments, the individual to which the composition is administered is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as an eye drop, through ophthalmic mucous membrane administration.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the compounds. These salts can be prepared in situ during the final isolation and purification of the compounds, or by separately reacting a purified compound in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. Preparation of the crystalline salts is detailed in the Examples, below (See, for example, Berge et al. (1977) "Pharmaceutical Salts," J. Pharm. Sci. 66: 1-19.).

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound. These salts can likewise be prepared in situ during the final isolation and purification of the compound, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); anally, rectally or vaginally (for example, as a pessary, cream or foam); parenterally (including intramuscularly, intravenously, subcutaneously or intrathecally as, for example, a sterile solution or suspension); nasally; intraperitoneally; subcutaneously; transdermally (for example as a patch applied to the skin); and topically (for example, as a cream, ointment or spray applied to the skin, or as an eye drop). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound of the present invention as an active ingredient. Compositions or compounds may also be administered as a bolus, electuary or paste.

To prepare solid dosage forms for oral administration capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the compositions of the present invention can also include adjuvants such as wetting agents, lubricants, emulsifying and suspending agents such as sodium lauryl sulfate and magnesium stearate, or sweetening, flavoring, coloring, perfuming, preservative, or anti oxidant agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions for rectal, vaginal, or urethral administration may be presented as a suppository, which may be prepared by mixing one or more active compounds with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the pharmaceutical compositions for administration to the mouth may be presented as a mouthwash, or an oral spray, or an oral ointment.

Alternatively or additionally, compositions can be formulated for delivery via a catheter, stent, wire, or other intraluminal device. Delivery via such devices may be especially useful for delivery to the bladder, urethra, ureter, rectum, or intestine.

Formulations which are suitable for vaginal administration also include pessaries, tampons, creams, gels, pastes, foams or spray formulations containing such carriers as are known in the art to be appropriate.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compounds described herein can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention. Exemplary ophthalmic formulations are described in U.S. Publication Nos. 2005/0080056, 2005/0059744, 2005/0031697 and 2005/004074 and U.S. Pat. No. 6,583,124, the contents of which are incorporated herein by reference. If desired, liquid ophthalmic formulations have properties similar to that of lacrimal fluids, aqueous humor or vitreous humor or are compatable with such fluids. A preferred route of administration is local administration (e.g., topical administration, such as eye drops, or administration via an implant).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinacious biopharmaceuticals. A variety of biocompatible polymers (including hydrogels), including both biodegradable and non-degradable polymers, can be used to form an implant for the sustained release of a compound at a particular target site.

These compounds may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the compounds, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts. In general, the compositions of this invention may be provided in an aqueous solution containing about 0.1-30% w/v of a compound disclosed herein, among other substances, for parenteral administration. Typical dose ranges are from about 0.01 to about 50 mg/kg of body weight per day, given in 1 single or 2-4 divided doses. Each divided dose may contain the same or different compounds of the invention.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans, and other mammals such as equines, cattle, swine and sheep; and poultry and pets in general.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

This invention includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts.

The pharmaceutically acceptable acid addition salts can also exist as various solvates, such as with water, methanol, ethanol, dimethylformamide, dimethylsulfoxide, and the like. Mixtures of such solvates can also be prepared. The source of such solvate can be from the solvent of crystallization, inherent in the solvent of preparation or crystallization, or adventitious to such solvent. In some embodiments, a solvate of a disclosed compound can be a dimethylsulfoxide solvate.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

The invention now being generally described, it will be more readily understood by reference to the following examples which are included merely for purposes of illustration of certain aspects and embodiments of the present invention, and are not intended to limit the invention.

EXAMPLES

Example 1: Synthesis of the Compound of Formula I Free Base

Step 1: Synthesis of Compoound 4

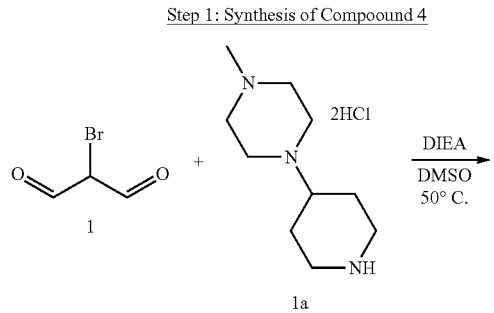

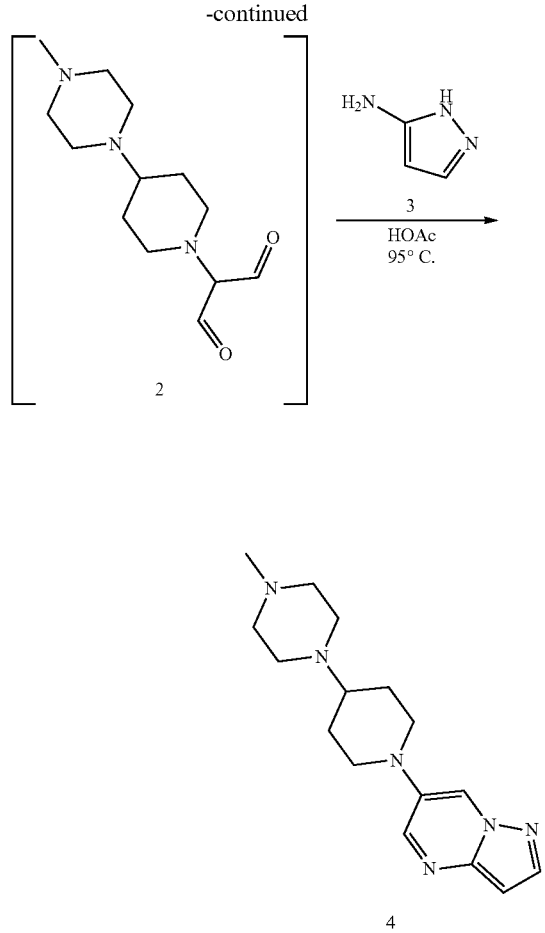

To a solution of 2-bromomalonaldehyde (700 g, 4.64 moles) in DMSO (2100 mL, 3 vol), and DIEA (889 mL, 5.1 moles) was added a solution of 1-methyl-4-(piperidin-4-yl)piperazine (1020 g, 5.56 moles) in DMSO (1050 mL, 1.5 vol). The reaction was heated to 50° C. and was stirred overnight. To the resulting solution was added a 40° C. solution of 3-aminopyrazole (385.2 g, 4.64 moles) in DMSO (350 mL, 0.5 vol). Glacial Acetic Acid (1.30 L, 22.4 moles) was added by addition funnel. An exotherm from 50.8° C. to 63.6° C. was observed upon addition. The reaction was heated to 95° C. for 6 hours, cooled to room temperature and stirred overnight. The resulting solid was removed by filtration, washed with DMSO (2×350 mL), and transferred to a 3 L 4-neck RBF. MTBE (3000 mL) was added and the slurry stirred for 3 hours. The solid was filtered, washed with MTBE (2×700 mL), and dried under vacuum at 55° C. for 2 hours. Isolated 505.0 g of compound 4. Yield=36.3%

$^1$H NMR (400 MHz, CHLOROFORM-d) δ=8.43 (d, J=2.5 Hz, 1H), 8.09 (d, J=2.7 Hz, 1H), 7.94 (d, J=2.3 Hz, 1H), 6.57 (s, 1H), 3.55 (br d, J=12.3 Hz, 2H), 2.73-2.53 (m, 7H), 2.47 (br s, 3H), 2.40-2.25 (m, 5H), 1.99 (br d, J=12.7 Hz, 2H), 1.73 (dq, J=4.0, 12.0 Hz, 3H)

Step 2: Synthesis of compound 5

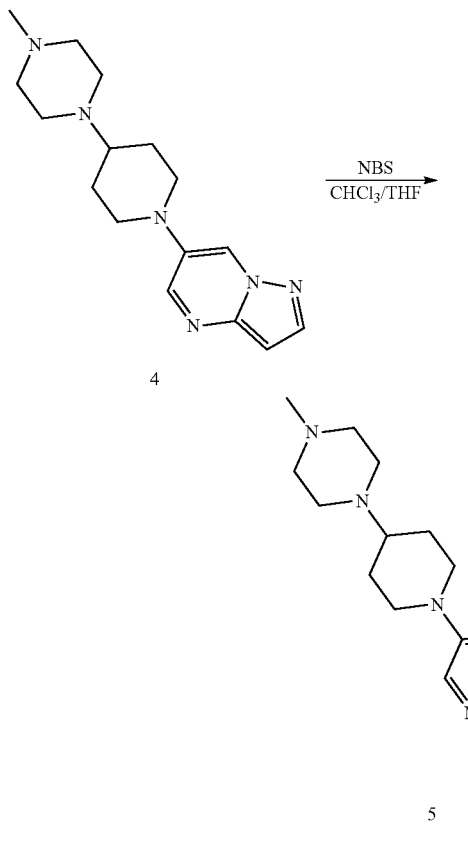

To a 0-5° C. solution of 6-(4-(4-methylpiperazin-1-yl)piperidin-1-yl)pyrazolo[1,5-a]pyrimidine (800 g, 2.66 moles), chloroform (9600 mL), and THF (2400 mL) was added solid NBS (477 g, 2.66 moles) portion wise over 3 hours while keeping the internal temperature<5° C. The resulting slurry was allowed to warm to room temperature while stirring overnight. The reaction was filtered and the undesired solids were rinsed with chloroform (2×800 mL). The filtrate was transferred to a separatory funnel and washed with sat. NaHCO$_3$ (6000 mL, 7.5 vol). The layers were separated, and the aqueous layer was back extracted with chloroform (1600 mL, 2 vol). The bottom organic layers were combined and washed with brine (5000 mL). The top aqueous layer was back extracted with chloroform (1600 mL, 2 vol). The bottom organic layer was concentrated until ~4 vol remained. The concentrated slurry was solvent swapped with heptane (3×2400 mL), concentrating back to 4 volumes each time and the resulting slurry was stirred overnight at ambient temperature. The slurry was filtered, washed with MTBE (2×1600 mL), and dried under vacuum at 40° C. overnight to yield 889 g of tan solid compound 5. Yield=85.6%

$^1$H NMR (400 MHz, CHLOROFORM-d) δ=8.48 (d, J=2.5 Hz, 1H), 8.03 (d, J=2.7 Hz, 1H), 7.92 (s, 1H), 3.55 (br d, J=12.3 Hz, 2H), 3.07-2.81 (m, 1H), 2.76-2.65 (m, 4H), 2.62 (br s, 4H), 2.50-2.27 (m, 8H), 1.98 (br d, J=12.7 Hz, 2H), 1.73 (dq, J=3.8, 12.0 Hz, 3H)

Step 3: Synthesis of Compound of Formula I free base

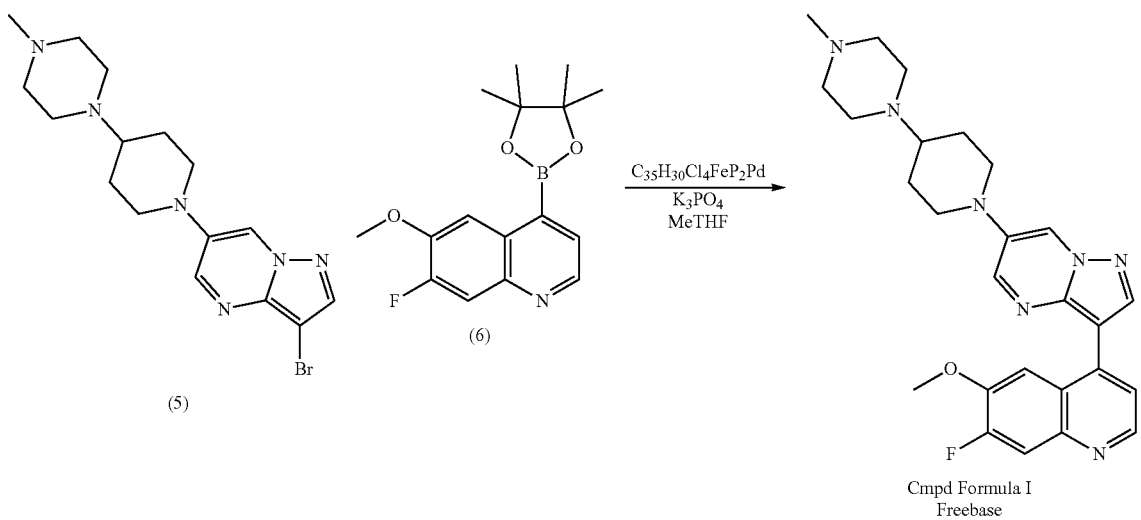

A slurry of 3-bromo-6-(4-(4-methylpiperazin-1-yl)piperidin-1-yl)pyrazolo[1,5-a]pyrimidine (Compound 5, 500 g, 1.32 moles), 7-fluoro-6-methoxy-4-(4,4,5,5-tetramethyl-1,3,2-dioxaborolan-2-yl)quinoline (420 g, 1.05 eq), 2-MeTHF (7.5 liters, 15 volumes) and 3 M K$_3$PO$_4$ (1.32 liters, 2.64 volumes, 3 eq) into a flask was degassed for 30 min with a nitrogen stream at room temperature. To the degassed slurry was added PdCl$_2$(dppf)DCM (75.4 g) and the resulting mixture was degassed with nitrogen for an additional 30 minutes. The reaction was heated to 60° C. and stirred overnight at 60° C. The resulting mixture was cooled and concentrated to minimum volume. To the concentrate was added CHCl$_3$ (7 liters, 14 volumes) and water (3.5 liters, 7 volumes) and after stirring for 30 min the layers are separated. The aqueous layer (top layer) was extracted with 2×5 liters (2×10 volumes) of CHCl$_3$. The combined organic layers were concentrated to a minimum volume and was taken up to 8.5 liters (17 volumes) of 1:1 MeOH: CHCl$_3$. To the resulting solution was added 250 g of Nexagen Thiopropyl silical gel and 250 g of Norit CAI carbon. The resulting slurry was heated to 50° C. overnight. The slurry was filtered at room temperature to remove solids and the resulting filtrate was concentrated to minimal volume. The thick slurry was taken up in 8.5 liters (17 volumes) of DCM and to the resulting solution was added 250 g of Nexagen Thiopropyl silical gel and 250 g of Norit CAI carbon and the resulting slurry was heated to 35° C. overnight. The slurry was filtered at room temperature to remove solids. The filtrate was placed in a separatory funnel and aqueous layer was removed. The resulting solution was solvent swapped with EtOAc where solids formed. The resulting slurry was diluted with EtOAc to a total volume of 5 liters (10 volumes). MTBE (2.5 liters) were added and the resulting slurry was stirred at room temperature overnight. Solids were filtered and washed with 2×2.5 liters (2×5 volumes) of MTBE yielding 430 g of title compound. (68.5% overall yield)

$^1$H NMR (400 MHz, CHLOROFORM-d) δ=8.83 (d, J=4.5 Hz, 1H), 8.57 (d, J=2.7 Hz, 1H), 8.31 (s, 1H), 8.22 (d, J=2.7 Hz, 1H), 7.80 (d, J=12.0 Hz, 1H), 7.60-7.53 (m, 2H), 3.90 (s, 3H), 3.75-3.55 (m, 3H), 2.89-2.73 (m, 2H), 2.68 (br s, 4H), 2.60-2.39 (m, 5H) 2.33 (s, 3H), 2.16-1.98 (m, 2H, 1.79 (dq, J=3.7, 11.9 Hz, 2H).

Example 2A: Synthesis of Amorphous Compound of Formula I Monosuccinate Salt

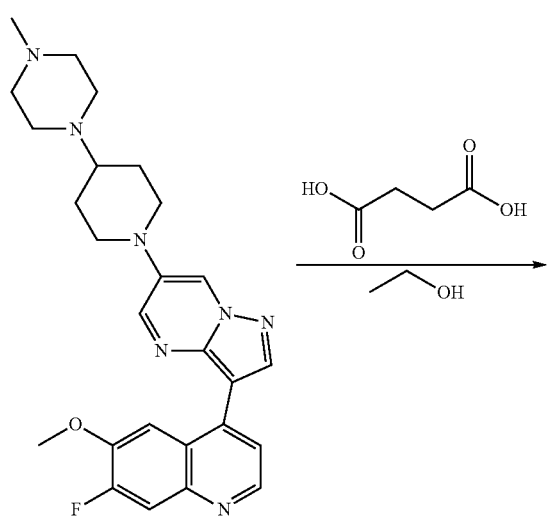

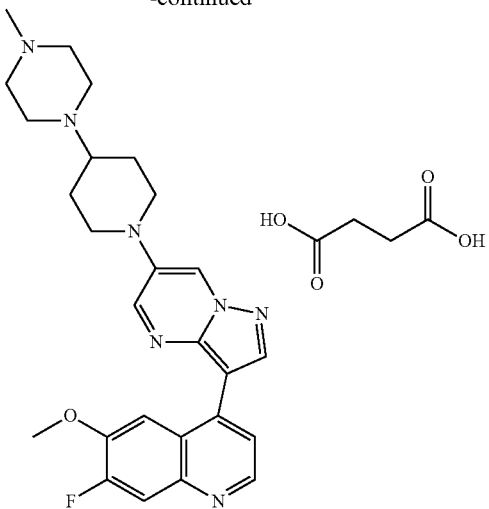

7-fluoro-6-methoxy-4-(6-(4-(4-methylpiperazin-1-yl) piperidin-1-yl)pyrazolo[1,5-a]pyrimidin-3-yl)quinoline (701.93 g, 1.48 moles) and ethanol (14 liters, 200 Proof) were allowed to stir at 70° C. for 2 hours. A solution of succinic acid (176 g, 1.49 moles and ethanol (5 liters, 200 proof) was slowly added and contents were allowed to stir at 75° C. for 8 hours to allow complete salt formation. The resulting slurry was concentrated under vacuum to 5 liters while keeping the internal temperature above 20° C. at all times during the concentration. Heptane was added to a total volume of 14 liters and the slurry was concentrated again while keeping the internal temperature above 20° C. The above concentration/reconstitution was done 6 times to achieve a solvent ration of ethanol in heptane of less than 5 Wt. %. as determined by proton NMR (CDCl$_3$). The final slurry was cooled to 20° C. and solids were filtered and not washed. Placed solids in a 45° C. oven under vacuum to constant weight to yield the title compound as yellow solid. (864.1 g, 98.6% Yield)

$^1$H NMR (400 MHz, DMSO-d6) δ=8.83 (d, J=2.6 Hz, 1H), 8.79 (d, J=4.6 Hz, 1H), 8.66 (d, J=2.7 Hz, 1H), 8.61 (s, 1H), 7.83 (d, J=12.3 Hz, 1H), 7.70 (s, 1H), 7.68 (d, J=4.6 Hz, 1H), 3.90 (s, 3H), 3.74 (br d, J=12.6 Hz, 2H), 2.78-2.62 (m, 3H), 2.61-2.52 (m, 3H), 2.47-2.33 (m, 9H), 2.23 (s, 3H), 1.90 (br d, J=11.7 Hz, 2H), 1.65-1.55 (m, 2H)

Example 2B: Synthesis of Amorphous Compound of Formula I Monosuccinate Salt

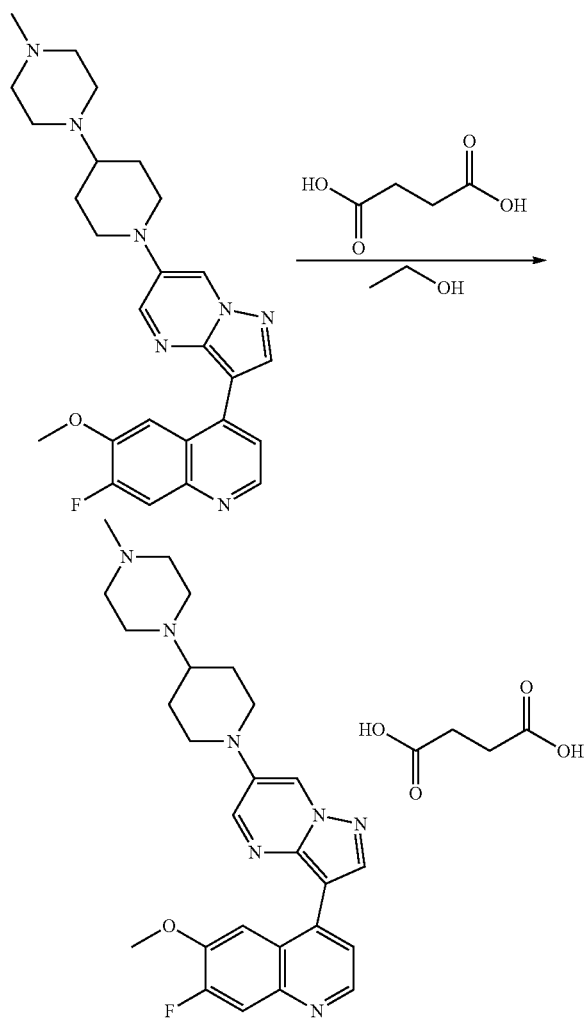

7-fluoro-6-methoxy-4-(6-(4-(4-methylpiperazin-1-yl)piperidin-1-yl)pyrazolo[1,5-a]pyrimidin-3-yl)quinoline (16 g, 0.336 moles) and ethanol (360 mL, 200 Proof) were allowed to stir at 70° C. for 2 hours. A solution of succinic acid (4.0 g, 0.339 moles and ethanol, 160 mL, 200 proof) was slowly added and contents were allowed to stir at 75° C. for 8 hours to allow complete salt formation. The resulting slurry was concentrated under vacuum to 160 mL while keeping the internal temperature above 20° C. (important for correct polymorph). Heptane was added to a total volume of 160 mL and the slurry was stirred above 20° C. for 8 hours. The final slurry was cooled to 20° C. and solids were filtered and washed with 2×23 mL of 1:1 ethanol: heptane. Placed solids in a 45° C. oven under vacuum and dried to constant weight to afford the title compound as solid. (18.26 g, 91% Yield)

$^1$H NMR (400 MHz, DMSO-d6) δ=8.83 (d, J=2.6 Hz, 1H), 8.79 (d, J=4.6 Hz, 1H), 8.66 (d, J=2.7 Hz, 1H), 8.61 (s, 1H), 7.83 (d, J=12.3 Hz, 1H), 7.70 (s, 1H), 7.68 (d, J=4.6 Hz, 1H), 3.90 (s, 3H), 3.74 (br d, J=12.6 Hz, 2H), 2.78-2.62 (m, 3H), 2.61-2.52 (m, 3H), 2.47-2.33 (m, 9H), 2.23 (s, 3H), 1.90 (br d, J=11.7 Hz, 2H), 1.65-1.55 (m, 2H)

Analytical Methods for Examples 3-7

X-Ray Powder Diffraction

X-ray powder diffraction (XRPD) patterns were collected on a Bruker D8 diffractometer using Cu Kα radiation (40 kV, 40 mA), θ-2θ goniometer and divergence of 0.6 mm and receiving slits, and a Lynxeye detector. The instrument is performance checked using a certified Corundum standard (NIST 1976). The software used for data collection was Diffrac Plus XRD Commander v2.6.1 and the data were analyzed and presented using Materials Data Jade Software v 9.7.0. Samples were prepared by transferring 2 to 50 mg of sample to a zero background holder coated with a thin layer of petroleum jelly and leveled with a glass plate and analyzed at ambient temperature. The sample was rotated in its own plane during analysis. Instrument parameters are provided in Table 1 below.

TABLE 1

| Analysis Parameters | |
|---|---|
| Scan Mode | Continuous PSD Fast |
| Time Per Step | 1 Second (192 sec Effective) |
| Scan Range | 2°-40° (2Θ) |
| Step Size | 0.05° |
| Sample Rotation | 15 Revolutions Per Minute |
| CuKα Radiation | 40 kV: 40 mA |
| Primary Beam Optics | |
| Divergence Slit | 0.6 mm |
| Primary Soller Slit | 2.5° |
| Secondary Beam Optics | |
| Secondary Soller Slit | 2.5° |
| Detector Slit Opening | None |
| Antiscatter Slit | 3 mm |
| Knife Edge | Present |
| Detector | 2.940° |

Differential Scanning Calorimetry

Differential scanning calorimetry (DSC) analysis was conducted with a TA Instruments Q1000 DSC, s/n 1000-0189. Samples were weighed into an aluminum hermetic pan and a lid with a manual pinhole. Pans were crimped using a Tzero press. Samples were analyzed at 10° C./minute from 25 to 350° C. Data was processed using Universal Analysis 2000, v 4.5A.

Thermogravimetric Analysis

Thermogravimetric analysis (TGA) was conducted with a TA Instruments Q50 TGA, s/n 50-0180. Samples were loaded in to a tared platinum TGA pan and analyzed at 10° C./minute from 25 to 350° C. Data was processed using Universal Analysis 2000, v 4.5A.

Dynamic Vapor Sorption/Desorption

Dynamic vapor sortion/desportion (DVS) analysis was conducted with a Hiden Isochema, IGAsorp, s/n IGSA 126. Samples were loaded in to a tared basket on the instrument and dried for 1 hour at 40° C. Samples were then analyzed at 25° C. with the following percent relative humidity (% RH) steps: Adsorption (% RH): 0.0, 10.0, 20.0, 30.0, 40.0, 50.0, 60.0, 70.0, 80.0, 90.0, 95.0, Desorption (% RH): 90.0, 80.0, 70.0, 60.0, 50.0, 40.0, 30.0, 20.0, 10.0, 0.0.

Example 3A: Compound of Formula I Free Base Characterization

Figure 4:
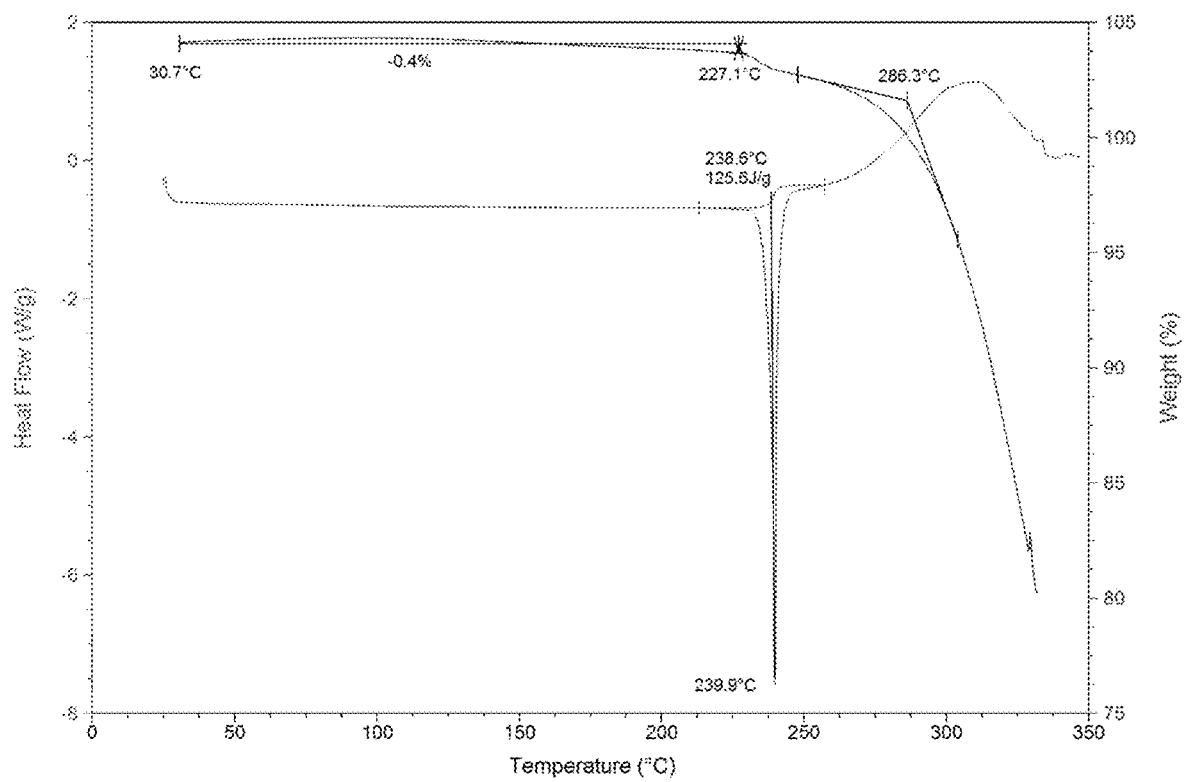
FIG. 4 shows the differential scanning calorimetry (DSC) and thermogravimetric analysis (TGA) spectra for the compound of Formula (I) free base.
Figure 5:
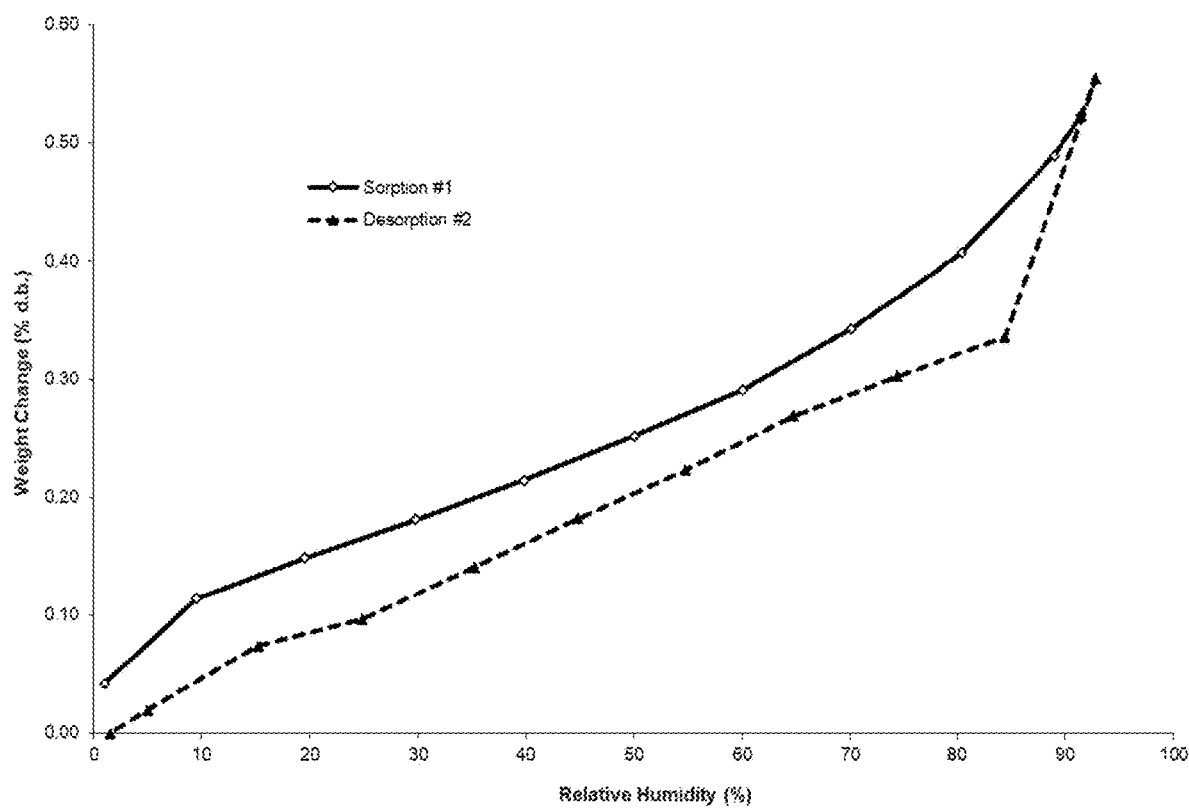
FIG. 5 shows the dynamic vapor sorption spectra (DVS) for the compound of Formula (I) free base.

Using the XRPD techniques detailed above, the compound of Formula I free base was crystalline and exhibited the following peaks: pg. 4 FIG. 3 In addition, the thermal data shows the free base is anhydrous and non-solvated (FIG. 4). The DSC exhibits a sharp endotherm with an onset of 238.6° C., indicative of a melt. Minimal weight loss (0.4%) is observed in the TGA until decomposition at 266.3° C. The DVS data indicates the material is non-hygroscopic with a weight gain and loss of 0.5% with slight hysteresis upon desorption (FIG. 5). No change is observed by XRPD after DVS analysis.

Figure 6:
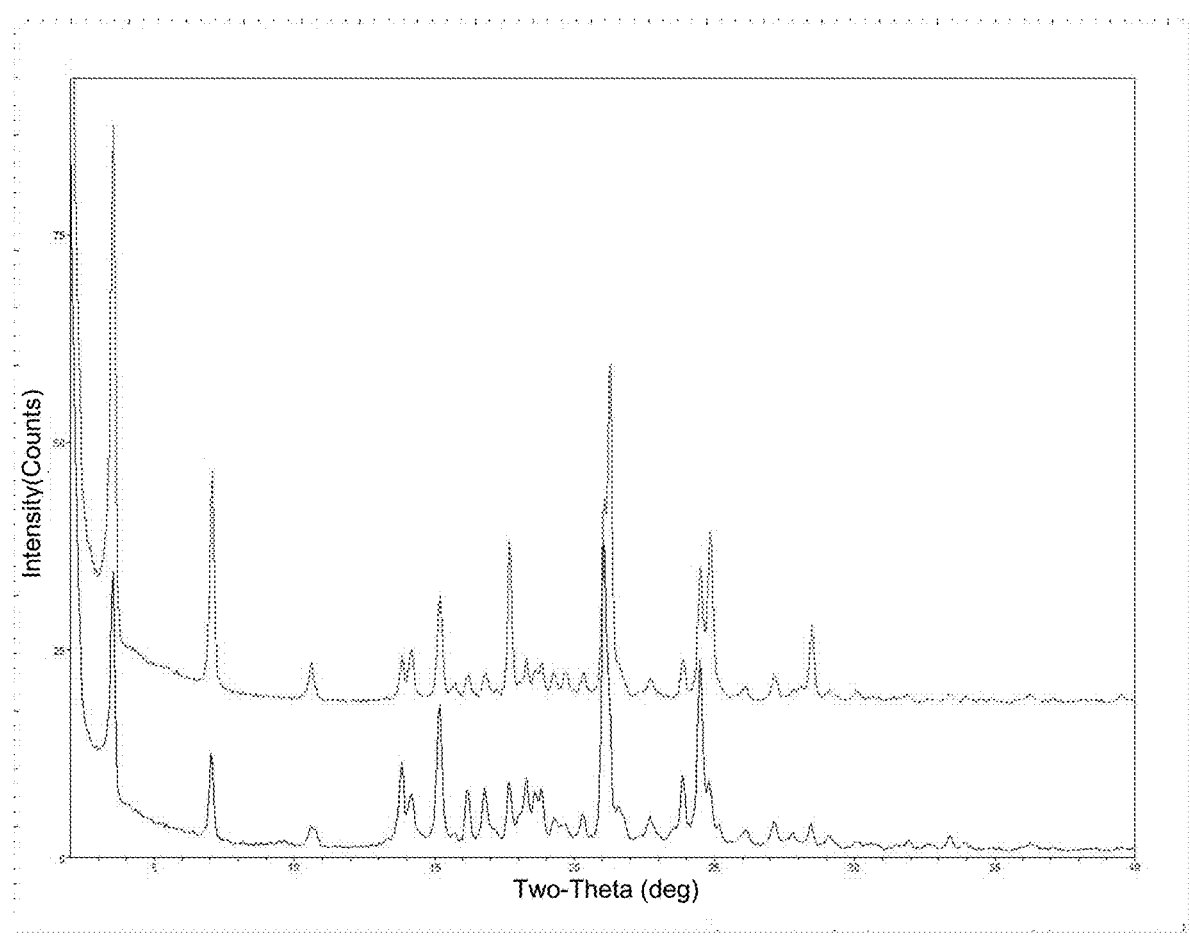
FIG. 6 shows the XRPD pattern of the compound of Formula (I) mono-succinate salt Form A reference sample and Form A prepared in THF.
Figure 7:
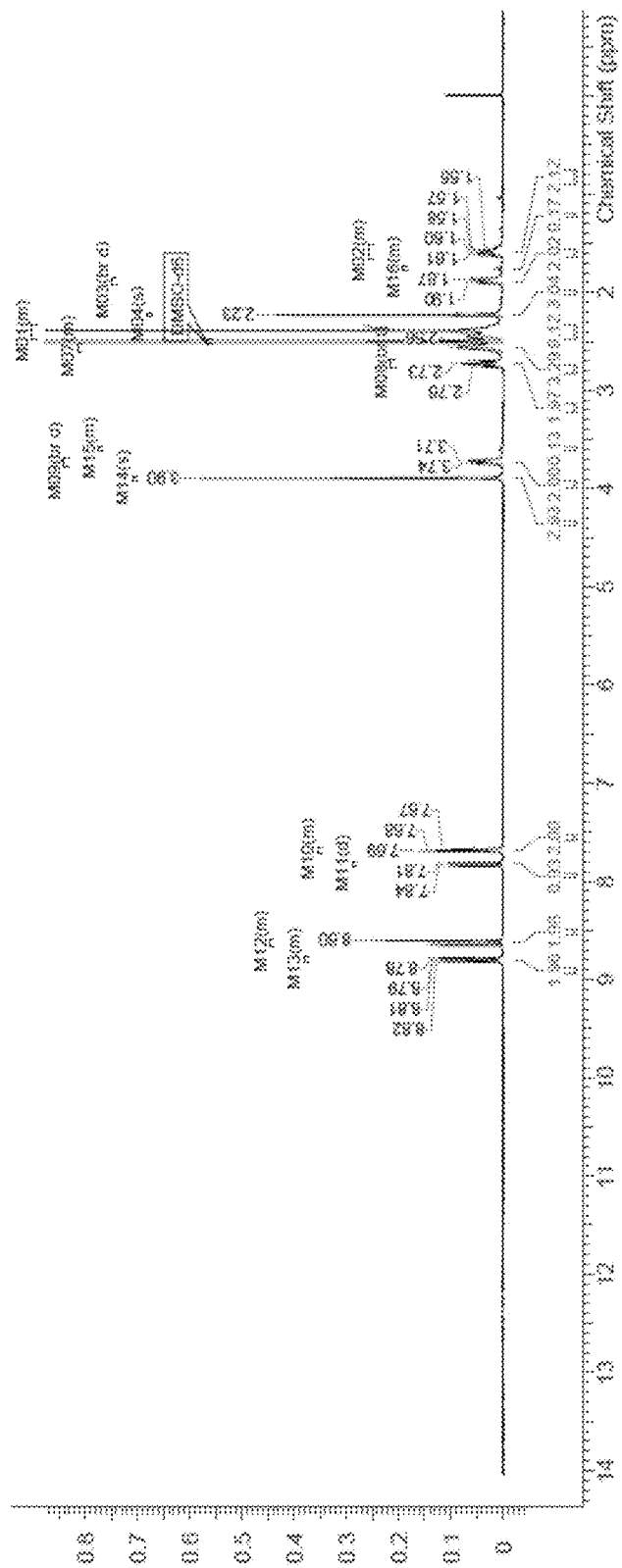
FIG. 7 shows an $^1$H-NMR spectrum of the compound of Formula (I) mono-succinate salt Form A.

Example 4A: Synthesis of Crystalline Compound of Formula I Mono-Succinate Salt Form A 2 g of Compound of Formula I free base was added to a 60 mL container. 0.5 g succinic acid was dissolved in 30 mL of THF, then the acid solution was added to the free base solids and allowed to stir at ambient temperature overnight. Solids were isolated by centrifugation using 0.45 μm nylon filter tubes and dried under vacuum for ~2 hours before XRPD (FIG. 6) and NMR (FIG. 7) analysis. Both analyses indicated that Form A was isolated from the scale-up. The peak at 2.6 ppm is attributed to one mole of succinic acid. The yield for the scale-up was 88%.

Figure 8:
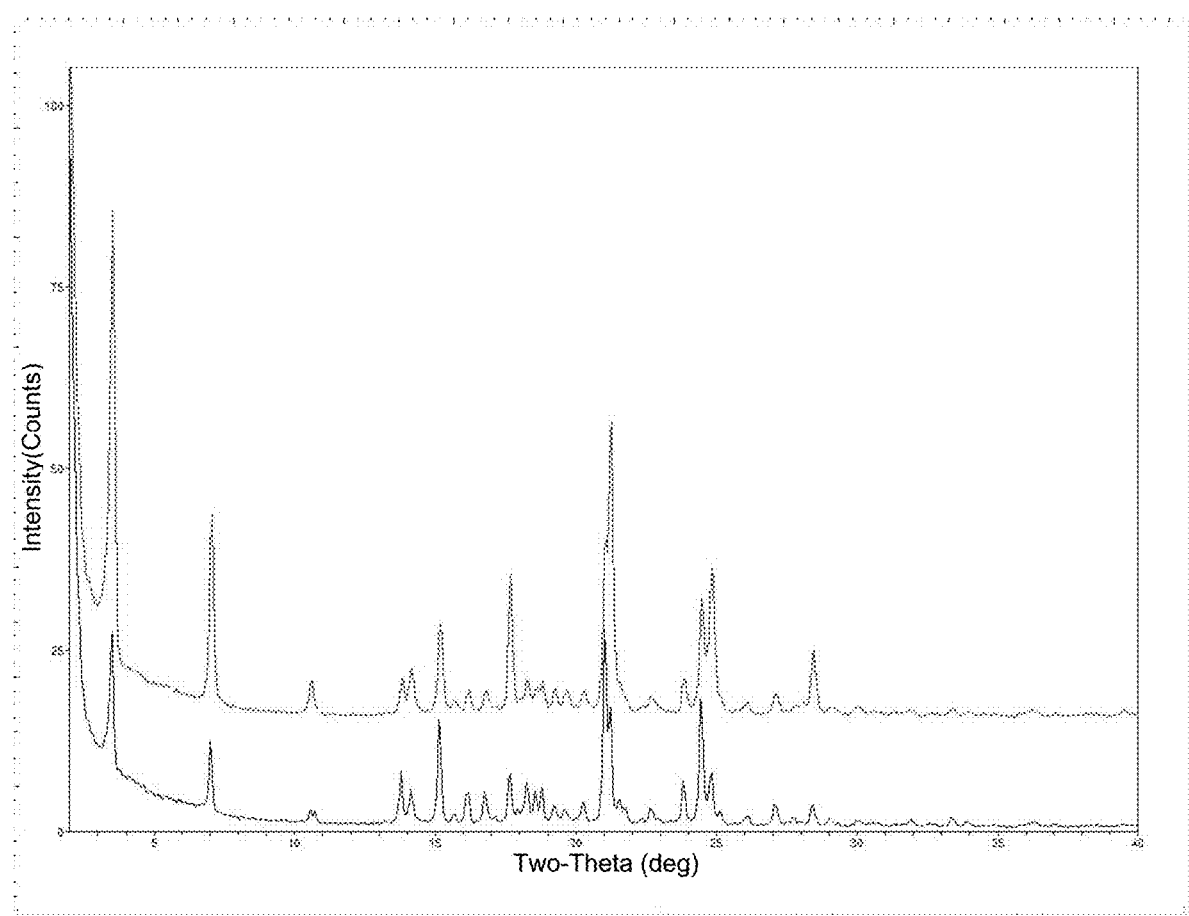
FIG. 8 shows the XRPD pattern of the compound of Formula (I) mono-succinate salt Form A reference sample and Form A prepared in EtOH.
Figure 9:
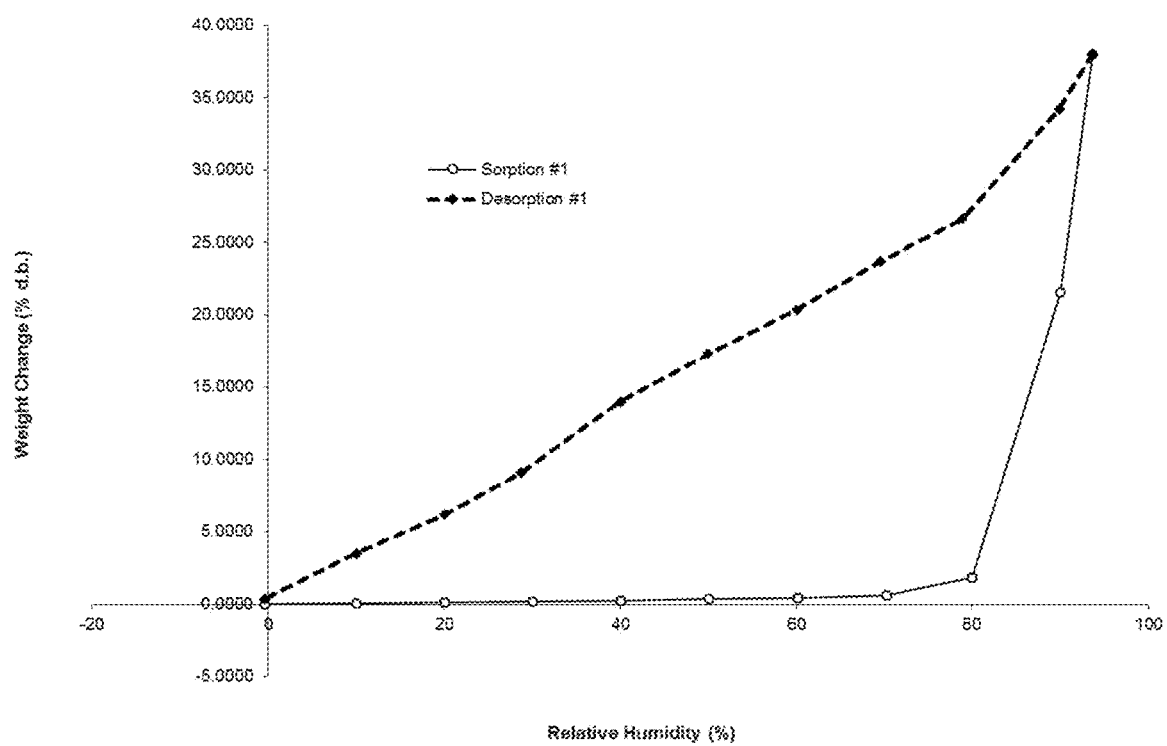
FIG. 9 shows the DVS for the compound of Formula (I) mono-succinate salt Form A prepared in EtOH.
Figure 10:
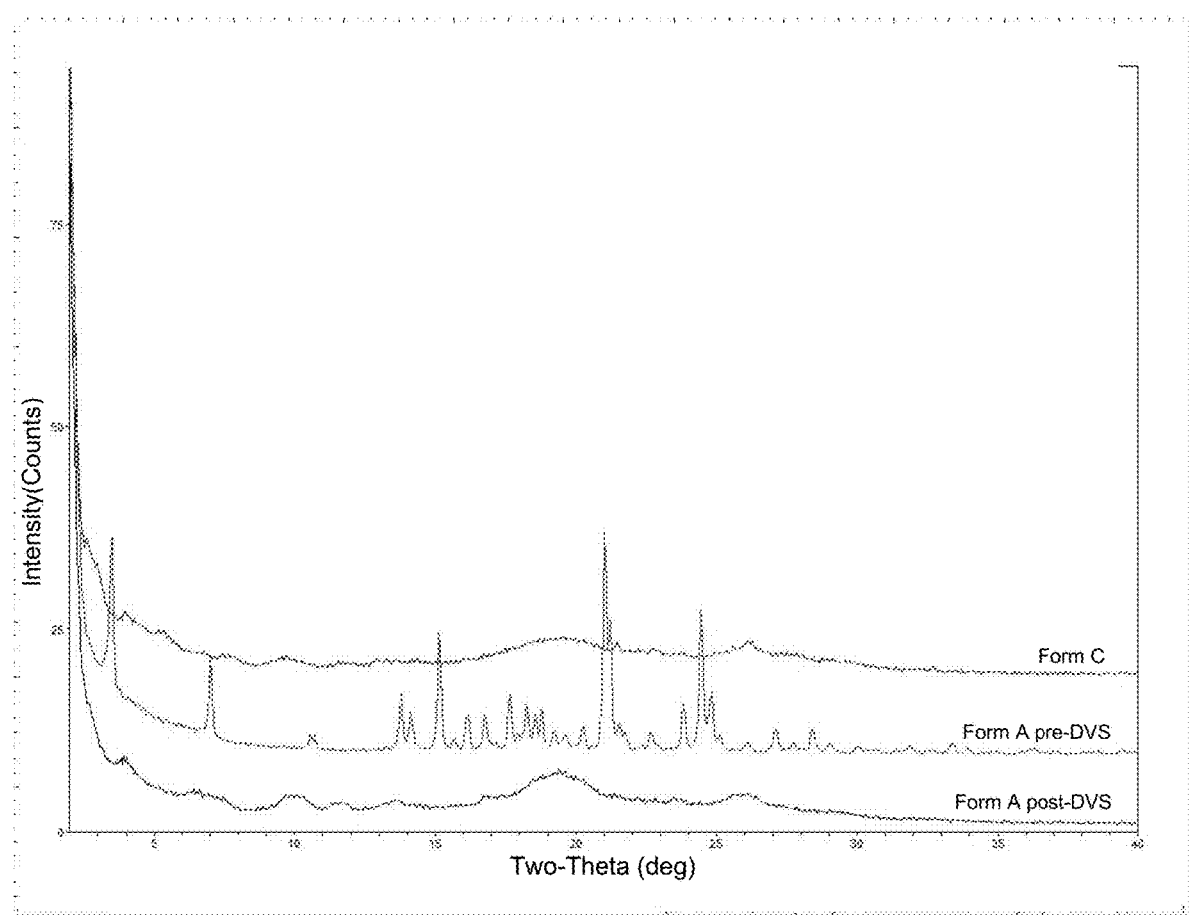
FIG. 10 shows an overlay of XRPD spectra for the compound of Formula (I) mono-succinate salt Form A pre- and post DVS analysis, along with the compound of Formula (I) mono-succinate salt Form C.

Example 4B: Synthesis of Crystalline Compound of Formula I Mono-Succinate Salt Forms a and C 2 g of Compound of Formula I free base was added to a 20 mL scintillation vial. 0.5 g succinic acid was dissolved in 20 mL of EtOH, then the acid solution was added to the free base solids and allowed to stir at ambient temperature overnight. Solids were isolated by centrifugation using 0.45 μm nylon filter tubes and dried under ambient conditions before XRPD analysis (FIG. 8), which indicated that Form A was isolated from the scale-up. The yield for the scale-up was 79%. This material was also analyzed by DVS (FIG. 9). The DVS indicates the material is hygroscopic with a weight gain and loss of 38% with significant hysteresis upon desorption. This is similar to the product of Example 3A. The material is non-hygroscopic below 80% RH. The post-DVS XRPD analysis (FIG. 10) indicates the material becomes highly disordered and converts to the hydrate, Form C.

Figure 11:
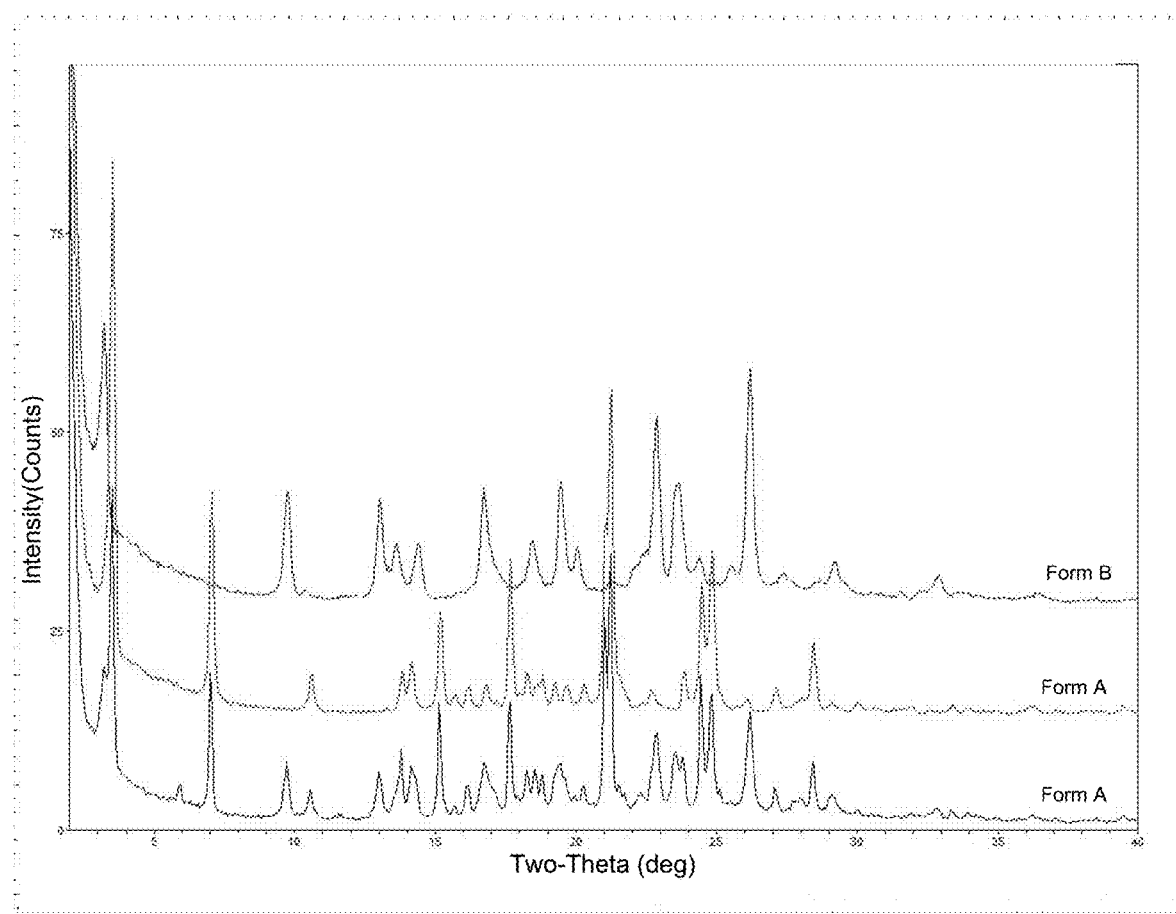
FIG. 11 shows an overlay of XRPD spectra for the compound of Formula (I) mono-succinate salt Form A prepared in EtOH, the compound of Formula (I) mono-succinate salt Form A reference sample, along with the compound of Formula (I) mono-succinate salt Form B.

Example 4C: Synthesis of Crystalline Compound of Formula I Mono-Succinate Salt Forms A and B 100 mg of Compound of Formula I free base was added to a 1 dram vial. 25 mg of succinic acid was dissolved in 1 mL of EtOH then the acid solution was added to the free base solids and slurried for 1 day. Solids were isolated by centrifugation using 0.45 μm nylon filter tubes and dried under ambient conditions before XRPD analysis, which indicates the material is a mixture of Form A and Form B (FIG. 11).

Example 5: Polymorph Solvent Screening Studies

Thirty experiments were initially conducted as part of the stable polymorph screen of compound of Formula I mono-succinate and are detailed in Table 2 and Table 3 gives nineteen experiments that began with compound of Formula I mono-succinate and were conducted using crystallization techniques that promote the formation of more stable polymorphs, such as slow cooling, slow evaporation, vapor diffusion, and slurries over an extended period of time. Table 4.3 gives eleven experiments were conducted to study the succinate salt formation of the compound of Formula I starting from the free base and varying ratios of succinic acid to determine if any other stoichiometries exist.

The stable polymorph and salt formation experiments resulted in either Form A, Form B, Form C, or a mixture of forms. Form C may be a hydrate, as it resulted from systems that contained water or solvents that are known to contain water (i.e. ethanol or THF). Form B was characterized to be an anhydrous polymorph that came from a variety of conditions and solvent systems during the screen. All polymorphs were confirmed to be a 1:1 stoichiometric salt with the compound of Formula I free base and succinic acid. No other stoichiometries of the succinate salt were identified.

TABLE 2

Polymorph screening study with the compound of Formula (I) mono-succinate salt

| Solvent | Experimental Conditions | Observations | XRPD Result |
|---|---|---|---|
| CHCl$_3$ | Attempted slow cool from 55° C. to RT | Thin slurry | Form B |
| Dioxane | Slow cool from 65° C. to RT | Clear soln then precipitate | Form A + Form B |
| EtOAc | Attempted slow cool from 65° C. to RT | Thin slurry | Form A + Form B |
| EtOH | Slurry, RT, 6 d | Yellow slurry | Form A |
| EtOH | Vapor diffusion w/heptane | Yellow slurry | Form A |
| IPA | Attempted slow cool from 65° C. to RT | Thin slurry | Form A |
| MeOH | Slurry, RT, 6 d | Yellow slurry | Form A |
| MeOH | Vapor diffusion w/ MTBE | Yellow slurry | Form A |
| THF | Slurry, RT, 6 d | Yellow slurry | Form A |
| Water | Slow cool from 55° C. to refrigerator, then fast evaporation | Thick, viscous gel with no solids | — |
| Water | RT slurry | Thick, viscous gel with no solids | — |
| — | 97% RH stress, RT | Dark yellow solids | Form C, disordered |
| 20:80 THF/H2O (a$_w$ = 0.96) | Slurry, RT, 6 d | Sticky solids, unable to isolate | — |
| 50:50 EtOH/H2O (a$_w$ = 0.84) | Slow cool from 55° C. to refrigerator | Clear soln then sticky solids, unable to isolate | — |
| 90:10 acetone/H2O (a$_w$ = 0.71) | Slurry, RT, 6 d | Yellow slurry | Form B + Form C |
| 90:10 acetone/H2O (a$_w$ = 0.71) | Slow cool from 55° C. to RT | Clear soln then precipitate | Form C, disordered |
| 90:10 EtOH/H2O (a$_w$ = 0.53) | Slurry, RT, 6 d | Yellow slurry | Form B + Form C |
| 90:10 EtOH/H2O (a$_w$ = 0.53) | Slow cool from 55° C. to refrigerator | Clear soln then precipitate | Form B |
| 98:2 IPA/H2O (a$_w$ = 0.28) | Slurry, RT, 6 d | Yellow slurry | Form A |

TABLE 3

Salt Formation Experiments with the Compound of Formula (I) free base and succinic acid

| Solvent | Experimental Conditions | Observations | XRPD Result |
|---|---|---|---|
| Acetone | 1:1 Compound of Formula I/succinic acid, heat to 55° C., cool to RT, isolate solids, dry under RT vacuum | Thin slurry | Form A |
| ACN | 1:1 Compound of Formula I/succinic acid, heat to 55° C., cool to RT, isolate solids, dry under RT vacuum | Thin slurry | Form A |
| EtOH | 1:1 Compound of Formula I/succinic acid, heat to 55° C., cool to RT, isolate solids, dry under RT vacuum | Clear soln then precipitate | Form A + minor Form C |
| EtOH | 1:2 Compound of Formula I/succinic acid, heat to 65° C., cool to RT, isolate solids | Clear soln then precipitate | Form A |
| EtOH | 2:1 Compound of Formula I/succinic acid, heat to 65° C., cool to RT, isolate solids | Clear soln then precipitate | Form A + minor Form C |
| EtOH | 1:6 Compound of Formula I/succinic acid, heat to 65° C., cool to RT, isolate solids | Thin slurry | Form B |
| EtOH | 1:1 Compound of Formula I/succinic acid, heat 100 mg API to 65° C. in 5 mL EtOH, add 25 mg acid in 5 mL EtOH at 65° C., add seeds of Form A, SC to RT | Clear soln then precipitate | Form A |
| EtOH | 1:1 Compound of Formula I/succinic acid, heat 100 mg API to 65° C. in 5 mL EtOH, add 25 mg acid in 5 mL EtOH at 65° C., add seeds of Form B, SC to RT | Clear soln then precipitate | Form A |
| THF | 1:2 Compound of Formula I/succinic acid, heat to 65° C., cool to RT, isolate solids, dry under RT vacuum | Thick slurry | Form B |
| THF | 2:1 Compound of Formula I/succinic acid, heat to 65° C., cool to RT, isolate solids, dry under RT vacuum | Thin slurry | Form A + minor Form C |
| EtOH | 500 mg free base in 10 mL EtOH, stir for 3.5 hours at 70° C., 125 mg succinic acid in 4 mL EtOH, heat at 75° C. for 6 hours, crash cool to freezer | Yellow slurry then upon addn of acid, solution cleared then yellow precipitate began to form, yellow solids after isolation | Form A |

Example 6: Stable Polymorph Solvent Screening Studies

Using compound of Formula (I) Form A as a starting material, the experiments below in Table 4 identified differences between Forms A and B, as both are anhydrous. Varying the ratios of ethanol and heptane, as well temperature conditions with these solvents were explored since these were selected as the final crystallization conditions. Additional experiments were conducted using crystallization techniques that promote the formation of more stable polymorphs, such as slow cooling and slurries over an extended period of time. Other experiments targeting metastable forms were also conducted, such as crash precipitation, crash cool, and fast evaporation techniques.

In addition to Forms A, B, and C, a new polymorph was identified in a mixture as Form D. Based on characterization data, this material is likely a hydrate. The disordered XRPD pattern of Form C is different that of the more crystalline Form D.

TABLE 4

Polymorph screening study beginning with the Compound of Formula (I) mono-succinate salt Form A

| Solvent | Experimental Conditions | Observations | XRPD Result |
|---|---|---|---|
| CHCl₃ | Slurry at 55° C., cool to refrigerator | Yellow slurry | Form B |
| CHCl₃ | Heat slurry to 55° C., isolate hot | Yellow slurry | Form B |
| CHCl₃ | RT slurry, 3 days | Yellow slurry | Form B |
| EtOAc | Crash cool from 70° C. to dry ice/IPA, isolate solids | Clear solution with yellow solids crashing out, then tacky yellow solids | Discontinued |
| EtOAc | Crash cool from 75° C. to freezer, then fast evaporation, cycle 1X | Clear soln then yellow solids | Form A |
| EtOH | Subambient slurry, 3 days | Yellow slurry | Form A |
| EtOH | Attempt crash precipitation w/heptane then freezer | Clear solution then yellow precipitate | Form A + Form D |
| EtOH | Ambient slurry, 3 d | Yellow slurry | Form A |
| EtOH | 40° C. slurry, 3 d | Yellow slurry | Form A |
| EtOH | Heat to 70° C., filter, add heptane in 1:1 ratio, freezer, then fast evaporation | Clear soln then yellow precipitate | Form A + Form B |
| EtOH | Heat to 70° C., filter, add heptane in 1:5 ratio, freezer, then fast evaporation | Clear soln then yellow precipitate | Form A + Form B |
| EtOH | Heat to 70° C., filter, add heptane in 1:10 ratio, freezer, then fast evaporation | Clear soln then yellow precipitate | Form B + Form D |
| EtOH | Heat to 70° C., filter, add heptane in 1:20 ratio, freezer, isolate solids | Clear soln then yellow precipitate, sticky yellow solids upon isolation | Discontinued |
| EtOH | Heat to 70° C., filter, add heptane in 1:5 ratio, refrigerator | Clear soln then yellow precipitate | Form A |
| EtOH | Heat to 70° C., filter, add heptane in 1:5 ratio, room temperature | Clear soln then yellow precipitate | Form A |
| MeOH | Subambient slurry, 3 days | Yellow slurry | Form A + Form B |
| MeOH | Ambient slurry, 3 d | Yellow slurry | Form A + Form B |

TABLE 4-continued

Polymorph screening study beginning with the
Compound of Formula (I) mono-succinate salt Form A

| Solvent | Experimental Conditions | Observations | XRPD Result |
|---|---|---|---|
| MeOH | 40° C. slurry, 3 d | Yellow slurry | Form A + Form B |
| THF | Crash cool from 60° C. to freezer, then fast evaporation, cycle 1X | Clear soln then yellow solids | Form A + minor Form B |

Figure 12:
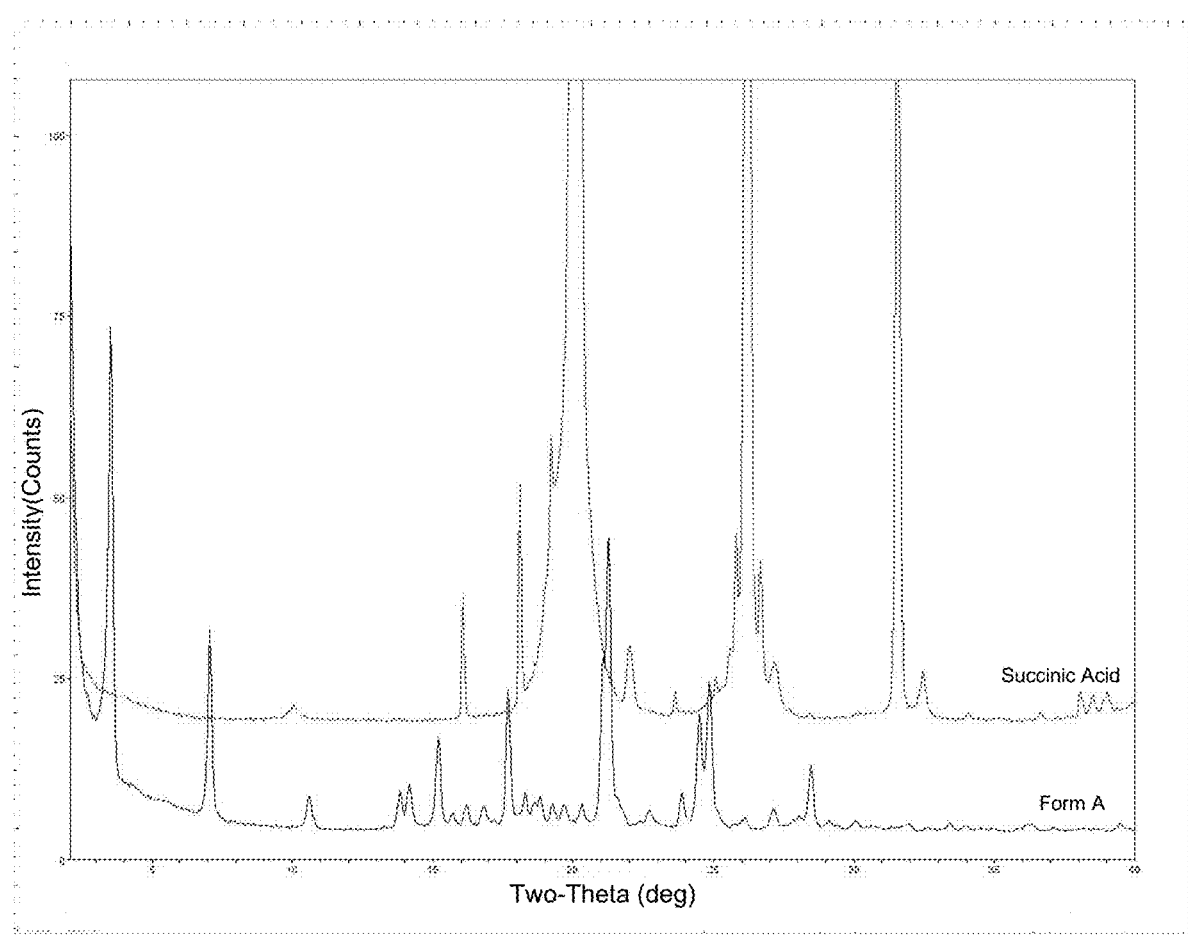
FIG. 12 shows the XRPD spectra of the compound of Formula (I) mono-succinate salt Form A and that of succinic acid.
Figure 13:
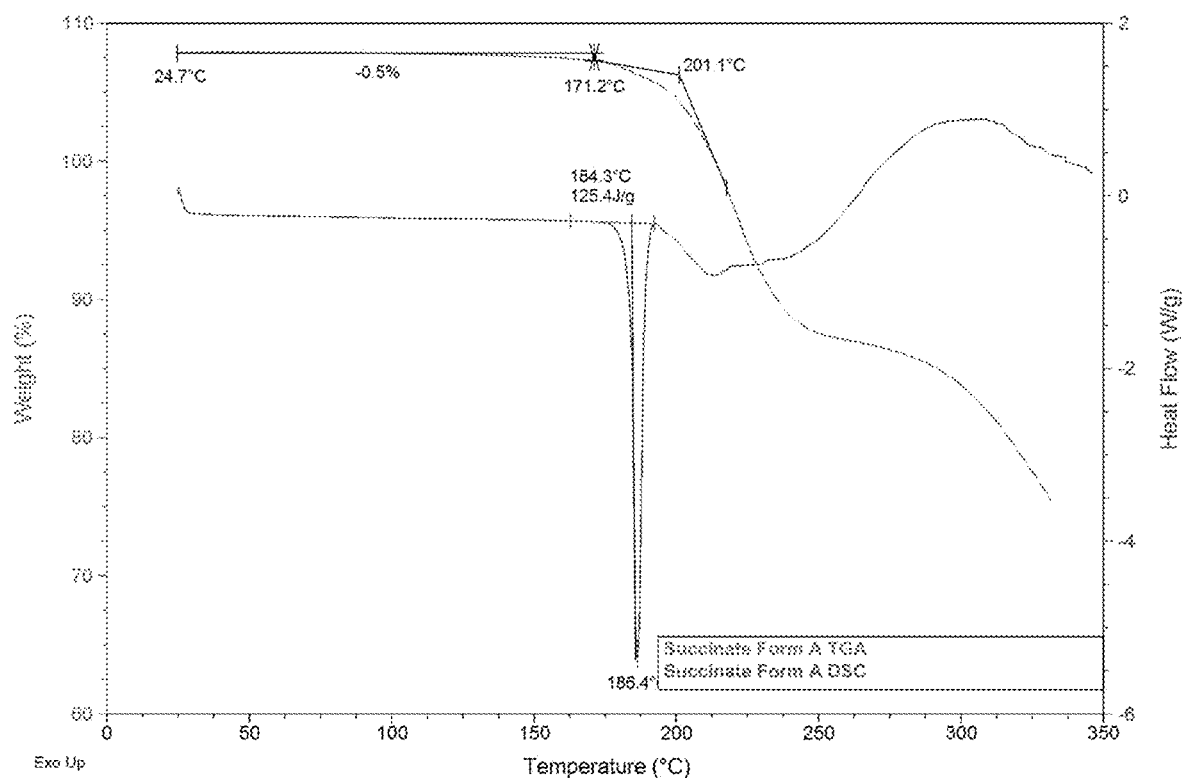
FIG. 13 shows the differential scanning calorimetry (DSC) and thermogravimetric analysis (TGA) spectra for the compound of Formula (I) mono-succinate salt Form A.

Form A is a crystalline solid that is anhydrous and non-solvated (FIG. 12). The DSC exhibits a sharp endotherm with an onset of 184.3° C. (FIG. 13). Minimal weight loss (0.5%) is observed in the TGA until decomposition at 201.1° C.

Figure 14:
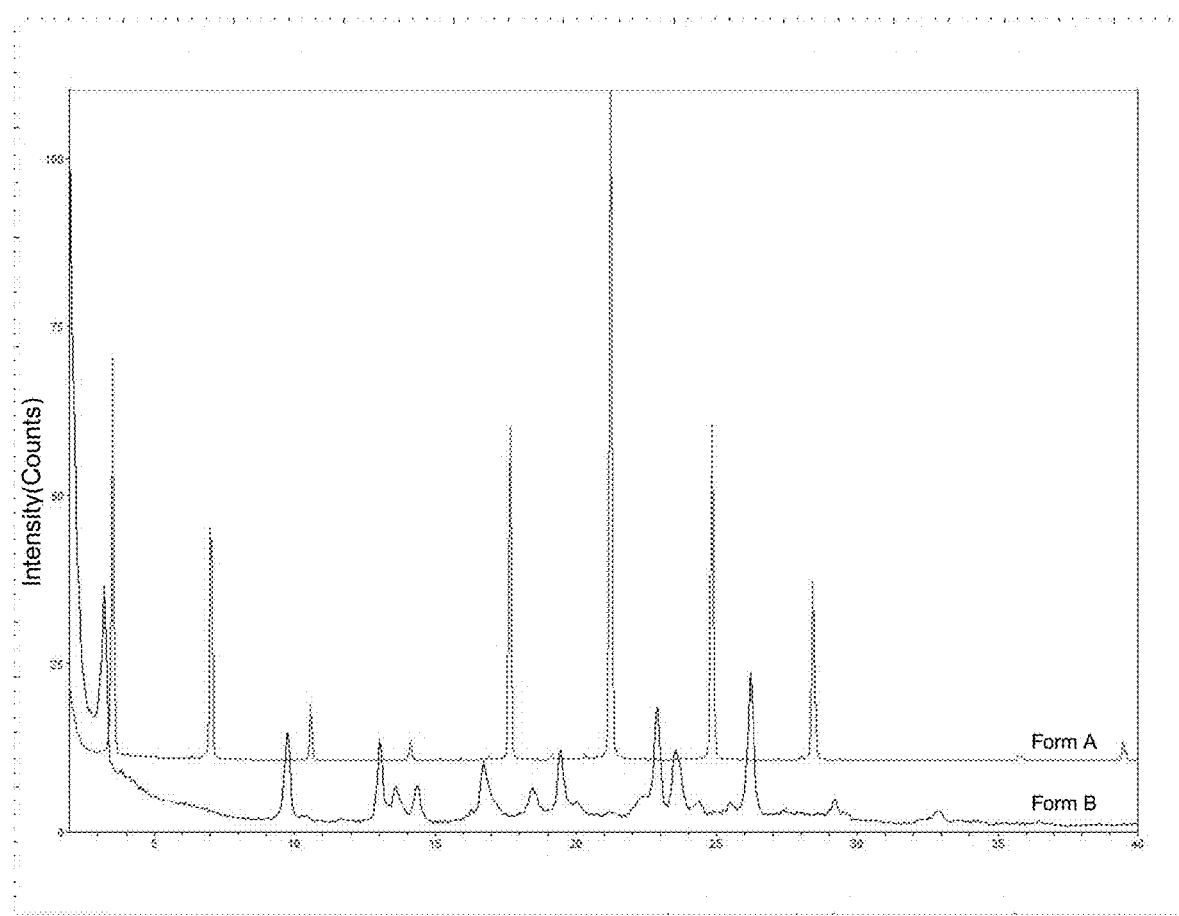
FIG. 14 shows the XRPD spectra of the compound of Formula (I) mono-succinate salt Form A and Form B.
Figure 15:
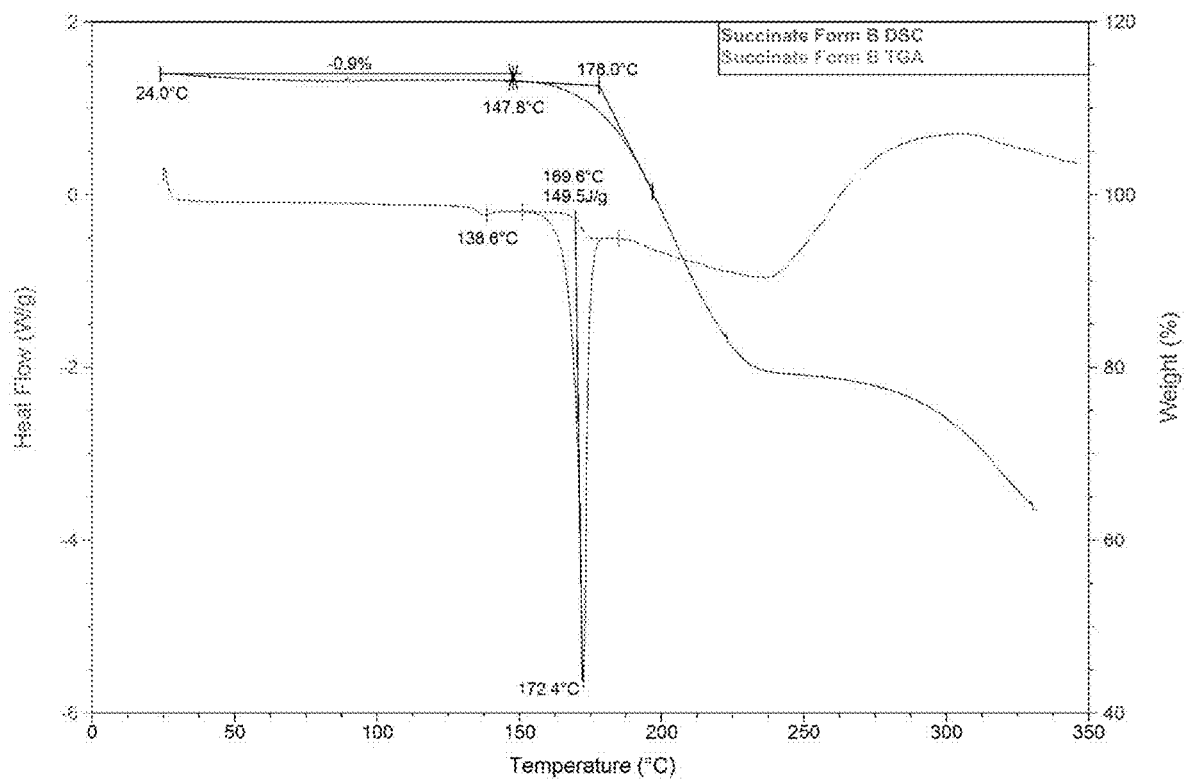
FIG. 15 shows the differential scanning calorimetry (DSC) and thermogravimetric analysis (TGA) spectra for the compound of Formula (I) mono-succinate salt Form B.
Figure 16:
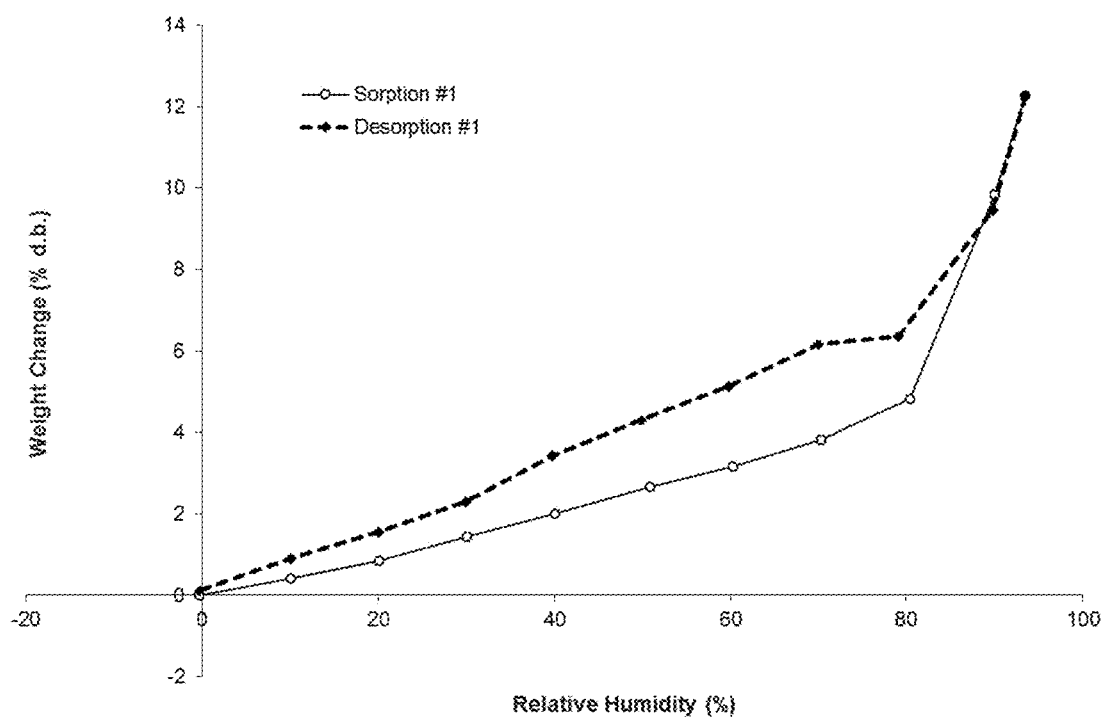
FIG. 16 shows the DVS for the compound of Formula (I) mono-succinate salt Form B.
Figure 17:
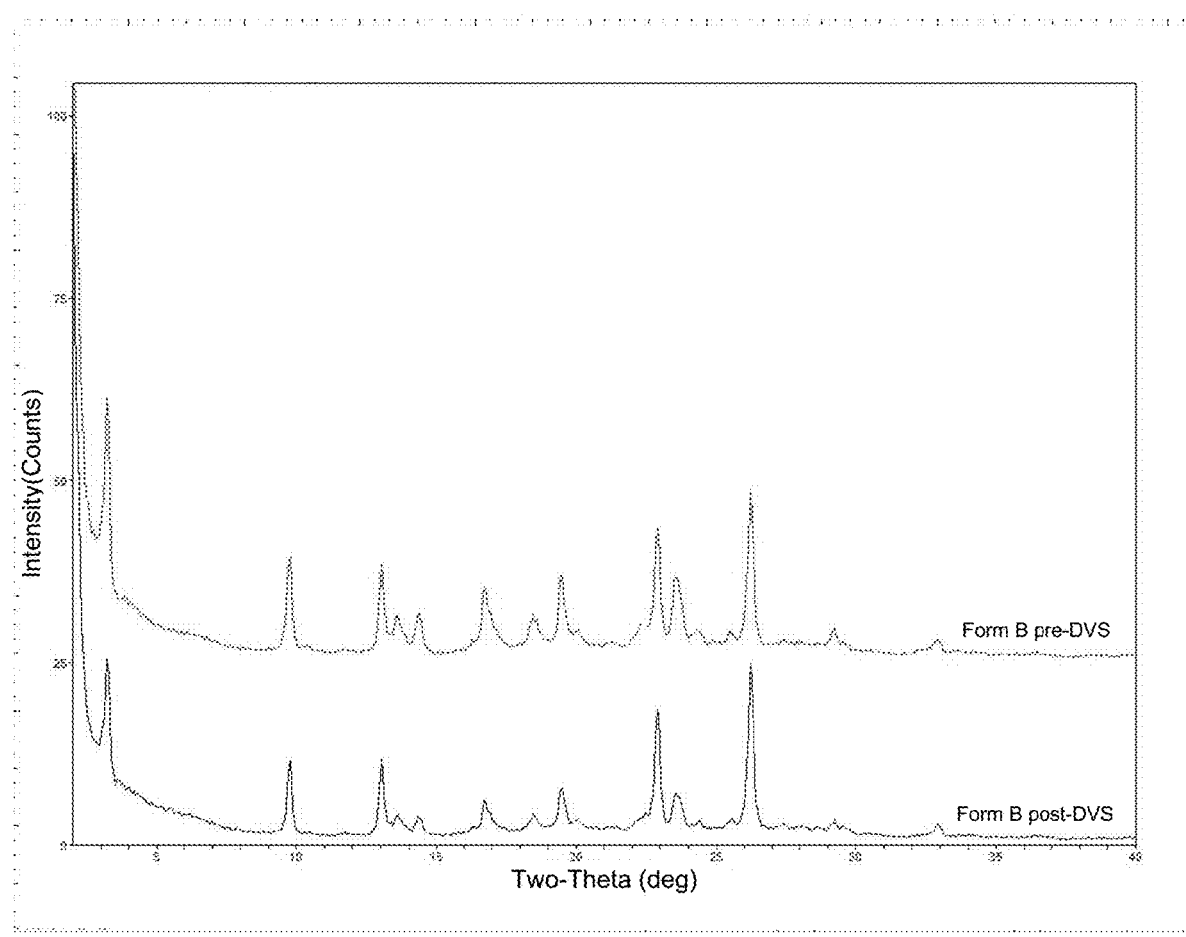
FIG. 17 shows an overlay of XRPD spectra for the compound of Formula (I) mono-succinate salt Form B pre- and post DVS analysis.
Figure 18:
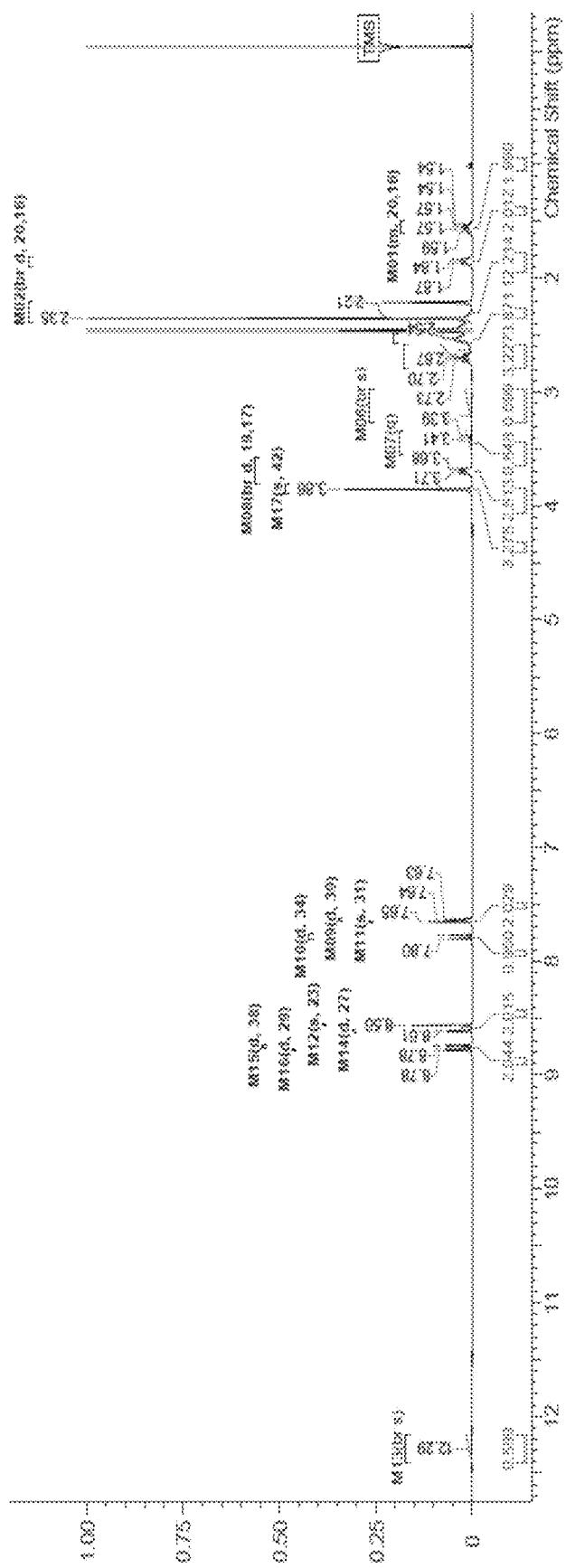
FIG. 18 shows an $^1$H-NMR spectrum of the compound of Formula (I) mono-succinate salt Form B.

Form B is a poorly crystalline solid that is anhydrous and non-solvated (FIG. 14). The DSC exhibits a small endotherm at 138.6° C. followed by a sharp endotherm with an onset of 169.6° C. Hotstage microscopy would be needed to determine the nature of the first small endothermic event. Minimal weight loss (0.9%) is observed in the TGA until decomposition at 178.0° C. (FIG. 15). The DVS data indicates the material is slightly hygroscopic with a weight gain and loss of 12% with slight hysteresis upon desorption (FIG. 16). Although Form B absorbs less moisture overall, the moisture gain of Form B begins immediately even at low relative humidities. The post-DVS XRPD analysis is consistent with Form B as well (FIG. 17). Chemical shifts in the proton NMR indicate the material is consistent with the chemical structure with no residual solvent present (FIG. 18). The peak at 2.6 ppm is attributed to one mole of succinic acid.

Figure 19:
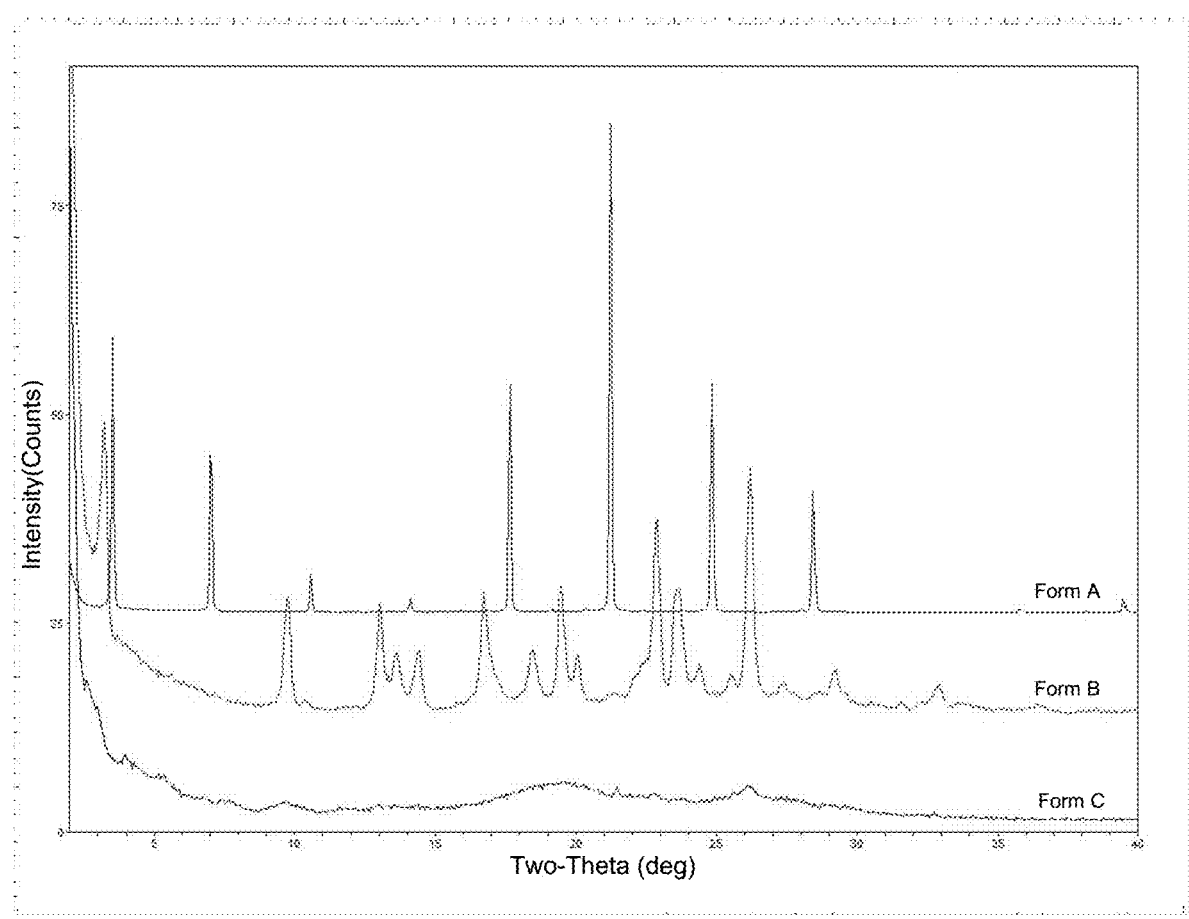
FIG. 19 shows an overlay of XRPD spectra for the compound of Formula (I) mono-succinate salt Form A, Form B and Form C.
Figure 20:
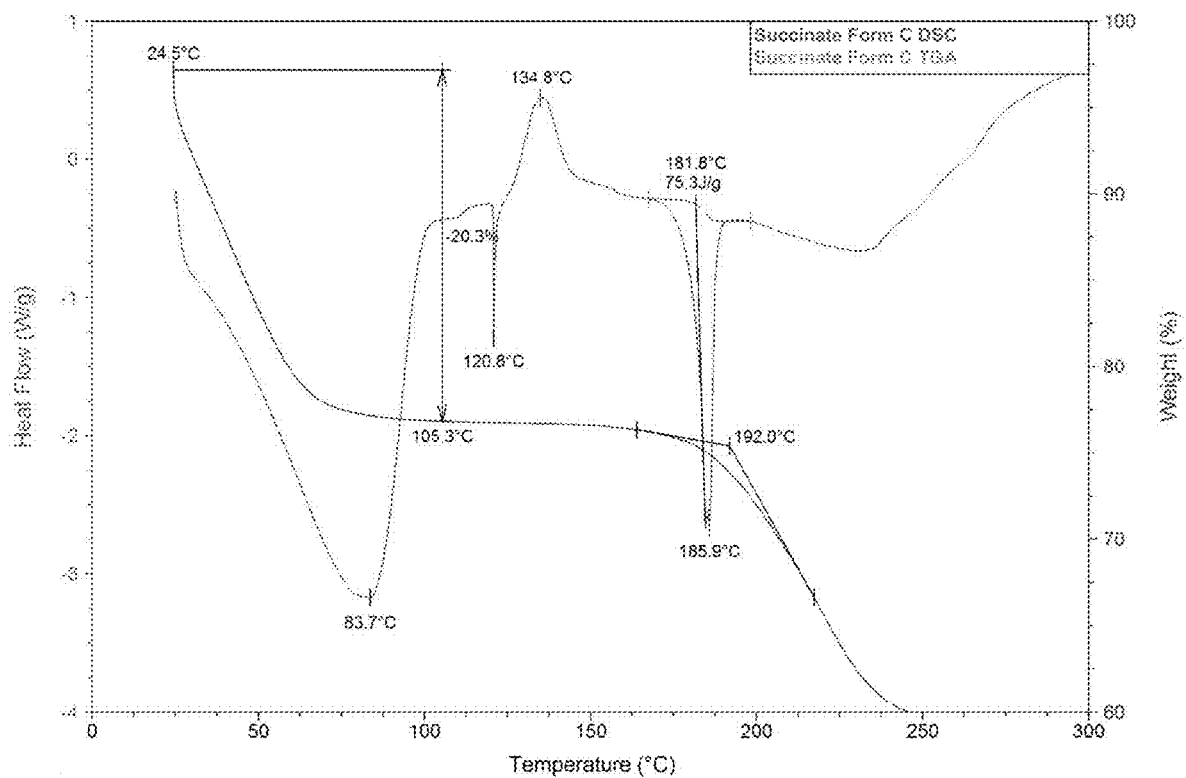
FIG. 20 shows the differential scanning calorimetry (DSC) and thermogravimetric analysis (TGA) spectra for the compound of Formula (I) mono-succinate salt Form C.
Figure 21:
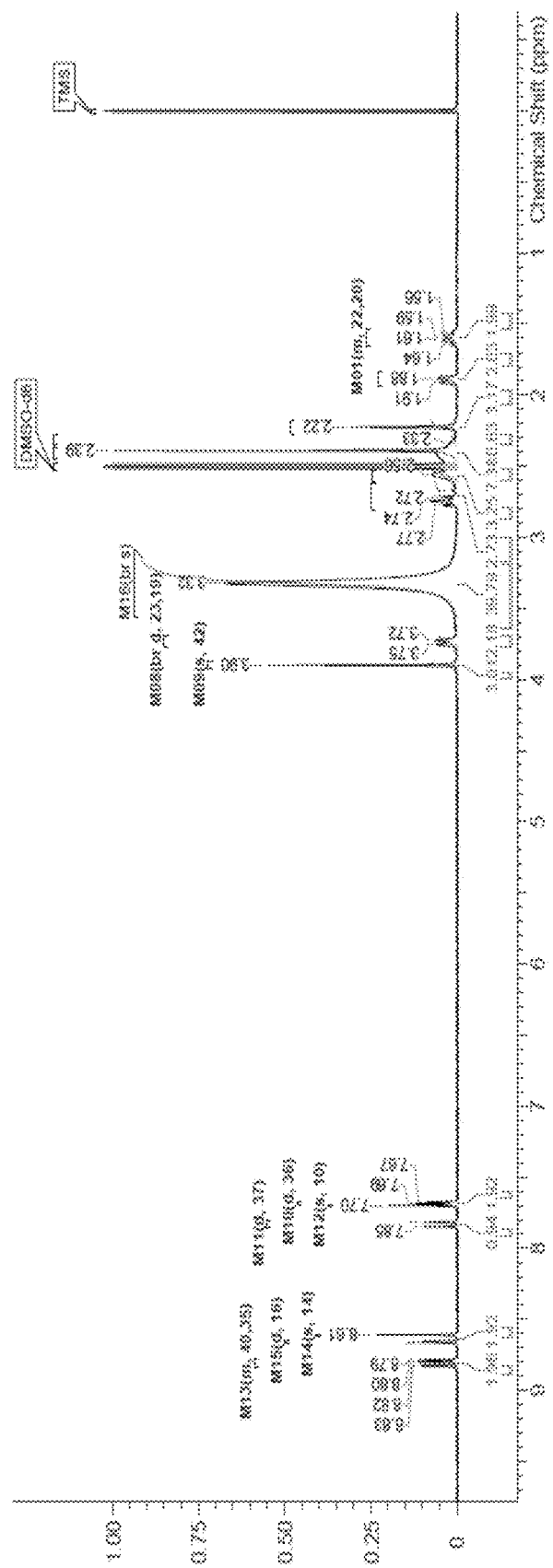
FIG. 21 shows an $^1$H-NMR spectrum of the compound of Formula (I) mono-succinate salt Form C.

Form C is a disordered material that is either hydrated or solvated (FIG. 19). The DSC exhibits an initial broad endotherm with a maximum of 83.7° C. followed by another endotherm with a maximum of 120.8° C. which is immediately followed by an exotherm with a maximum of 134.8° C. A final sharp endotherm is observed with an onset of 181.8° C. This suggests that Form C may desolvate and recrystallize to Form A, which has a melt of 184° C. (FIG. 20). Chemical shifts in the proton NMR are consistent with the chemical structure, with no residual solvent present, indicating that Form C is indeed a hydrate (FIG. 21). The peak at 2.6 ppm is attributed to one mole of succinic acid.

Figure 22:
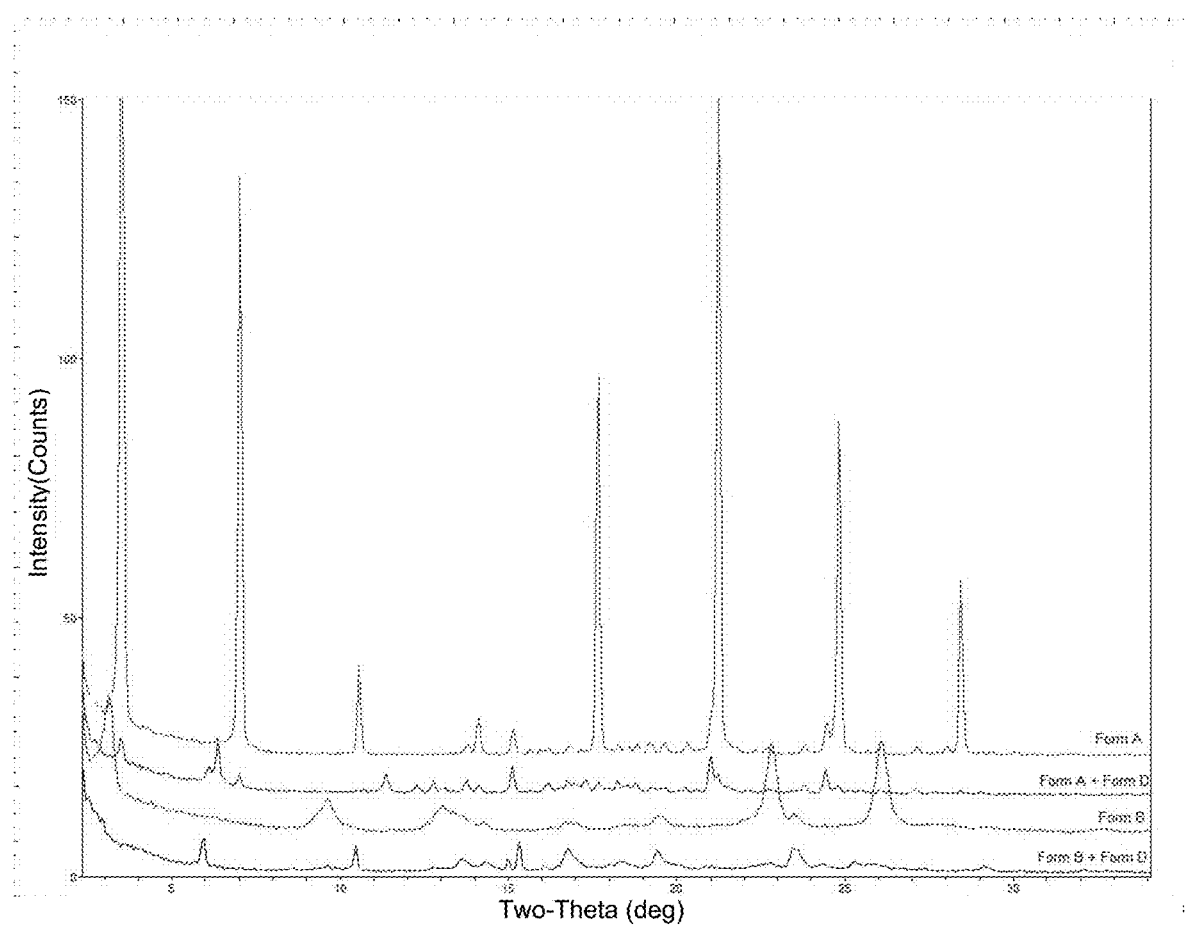
FIG. 22 shows an overlay of XRPD spectra for the compound of Formula (I) mono-succinate salt Form A, Form B and Form D.
Figure 23:
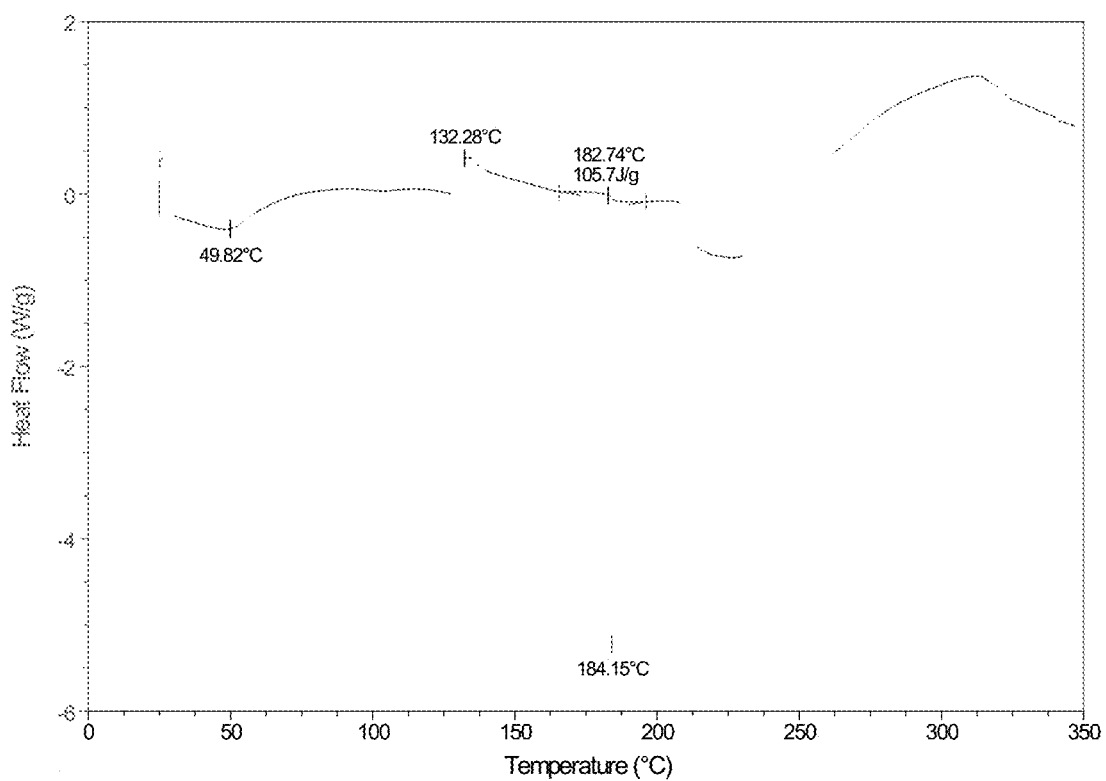
FIG. 23 shows the differential scanning calorimetry (DSC) for a mixture of Forms A and D of the compound of Formula (I) mono-succinate salt.
Figure 24:
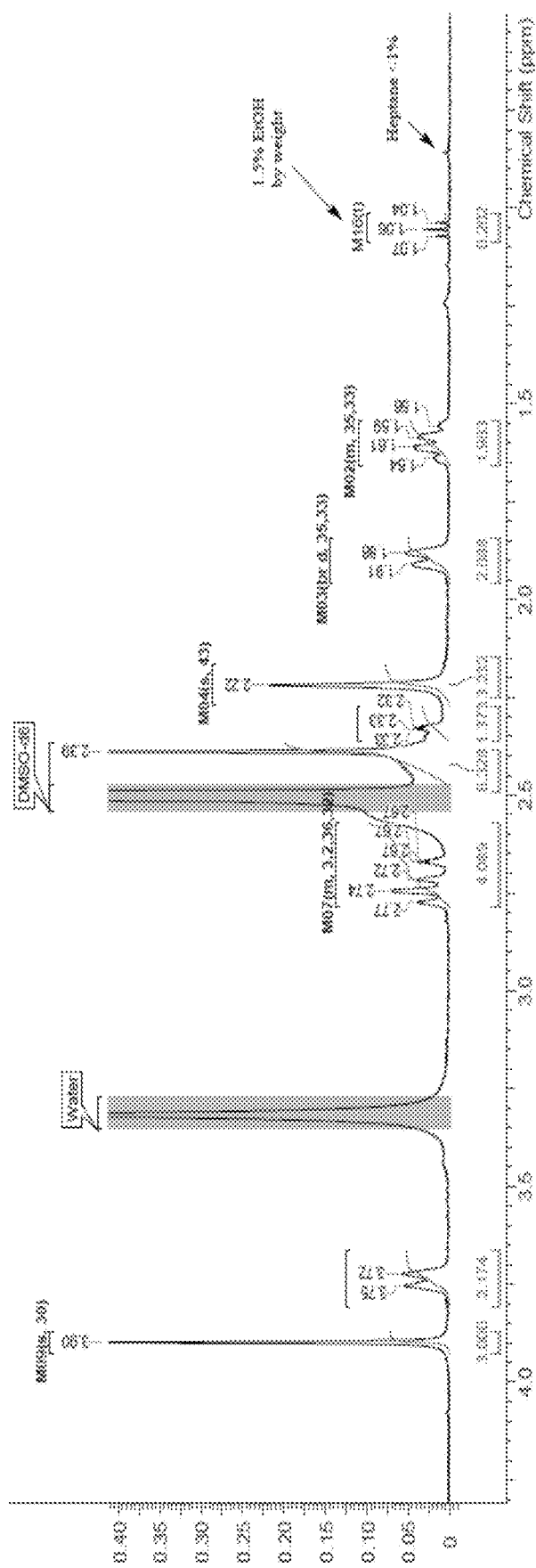
FIG. 24 shows an $^1$H-NMR spectrum of the compound of Formula (I) mono-succinate salt Form D.
Figure 25:
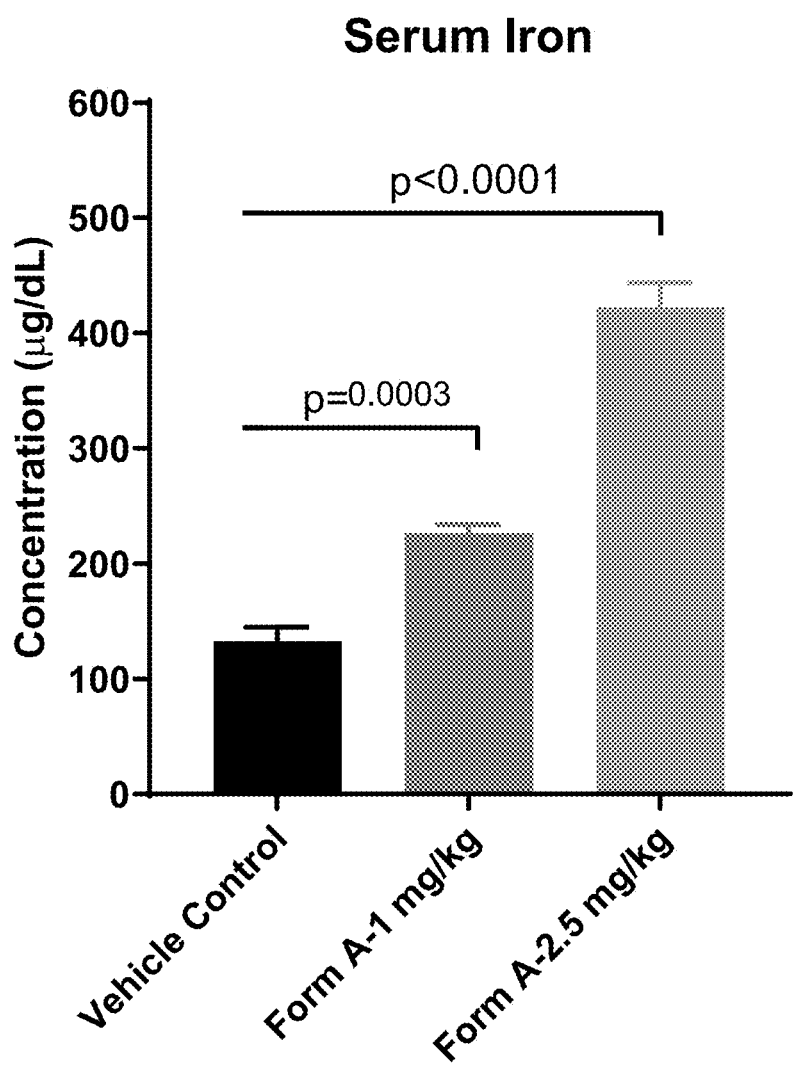
FIG. 25 shows serum concentration of iron resulting from dosing of Form A.
Figure 26:
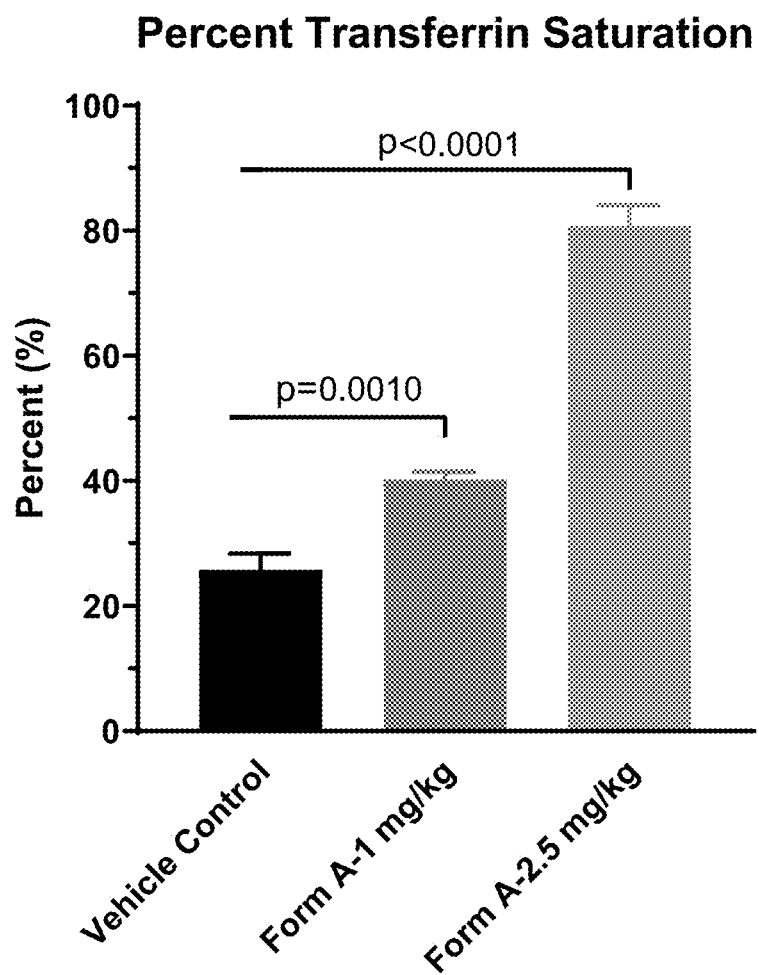
FIG. 26 shows percent transferrin saturation resulting from dosing of Form A.

Form D was obtained as described above as a mixture with Form A or Form B, as shown by arrows in the comparative XRPD spectra shown in FIG. 22. Form D was obtained using either ethanol or heptane. The thermal data shows Form D is hydrated or solvated (FIG. 23). The DSC exhibits an initial broad endotherm with a maximum of 49.8° C. followed by a small exotherm with a maximum of 132.3° C. which is immediately followed by an exotherm with a maximum of 134.8° C. A final sharp endotherm is observed with an onset of 182.7° C. Thus, Form D may desolvate and recrystallize to Form A, which has a melt of 184° C. Because this sample also contained a mixture of Form A, there were seeds of Form A present which may have promoted the recrystallization. Chemical shifts in the proton NMR are consistent with the chemical structure, with little residual solvent present (1.5% EtOH by weight), indicating that Form D is possibly a hydrate (FIG. 24). The peak at 2.6 ppm is attributed to one mole of succinic acid.

Example 7: Compound of Formula I Form A and B Competitive Slurries

To determine the thermodynamically stable polymorph between anhydrous Forms A and B, competitive slurries were conducted in three different solvent systems: ethanol, tetrahydrofuran, and 2-butanone (MEK)/water (95:5). Each solvent system was evaluated at three different temperatures: 5° C., ambient (RT), and 40° C. as shown in Table 5. Ethanol and tetrahydrofuran were chosen based on the solubility of the material. MEK was chosen as a potential process solvent and water was added to boost the solubility.

TABLE 5

Form A and Form B Competitive Slurries Part 1

| Solvent | Experimental Conditions | Observations | XRPD Result |
|---|---|---|---|
| EtOH | 5° C., slurry 5 days | Yellow slurry | Form A + Form B |
| THF | 5° C., slurry 5 days | Yellow slurry | Form A + Form B |
| MEK/H2O 95:5 | 5° C., slurry 5 days | Yellow slurry | Form C + Form B, highly disordered |
| EtOH | RT, slurry 5 day | Yellow slurry | Form A + Form B |
| THF | RT, slurry 5 days | Yellow slurry | Form A + Form B |
| MEK/H2O 95:5 | RT, slurry 5 days | Yellow slurry | Form C + Form B, highly disordered |
| EtOH | 40° C., slurry 5 days | Yellow slurry | Form A |
| THF | 40° C., slurry 5 days | Yellow slurry | Form A + Form B + minor Form C |
| MEK/H2O 95:5 | 40° C., slurry 5 days | Yellow slurry | Form C + Form B, highly disordered |

The addition of 5% of water resulted in partial conversion to the hydrate, Form C. The use of solvents known to contain water, such as THF, also resulted in partial conversion to Form C. Thus, additional competitive slurries were conducted in three additional solvent systems: ethanol/heptane (1:5), ethyl acetate/water (97:3), and isopropanol/water (99:1). The ethanol/heptane system was evaluated at −15° C., 5° C., ambient (RT), and 40° C. The water containing systems were only evaluated at ambient temperature. The results are shown below in Table 6. The slurries were conducted for 7 days instead of 5 days, as done in the above slurries. Form D was also included in the competitive slurries containing water.

TABLE 6

Form A and Form B Competitive Slurries Part 2

| Solvent | Experimental Conditions | Observations | XRPD Result |
|---|---|---|---|
| EtOH/heptane 1:5 | Form A + Form B slurry, 40° C., 7 days | Yellow slurry | Form A + minor Form B |
| | Form A + Form B slurry, RT, 7 days | Yellow slurry | Form A + minor Form B |
| | Form A + Form B, 5° C., 7 days | Yellow slurry | Form A + minor Form B |
| | Form A + Form B slurry, −15° C., 7 days | Yellow slurry | Form A + minor Form B |
| EtOAc/water 97:3 ($a_w$ = 0.93) | Form A + Form B + Form D slurry, RT, 7 days | Dark yellow slurry | Form C |
| IPA/water 99:1 ($a_w$ = 0.13) | Form A + Form B + Form D slurry, RT, 7 days | Yellow slurry | Form A |

The above results indicate that over time, Form A is the most stable polymorph, due to the decrease in the presence of Form B compared to slurries conducted over 5 days. The wide temperature range studied (~40° C. down to −15° C.) was designed to determine if a critical transition temperature existed between Forms A and B. Although Form A had the higher melting endothermic event, the heat of fusion of Form B was higher, such that thermodynamical stability may rest with Form A.

The 97:3 EtOAc/water slurry resulted in full conversion to Form C, however the 99:1 IPA/water slurry resulted in Form A. These data indicate that at low water activity, the anhydrous Form A is most thermodynamically stable. At high water activity, the hydrate Form C is more favored.

Example 8: Serum Iron Levels

This study evaluated blood iron parameters upon administration of Form A. 8-week-old healthy male Sprague Dawley rats were dosed daily, by oral gavage, with vehicle or Form A at doses of 1 and 2.5 mg. After 90 days of dosing, the study was terminated and serum samples taken for analysis of iron parameters. Sampled blood was allowed to clot at room temperature before spinning down in a centrifuge and serum aliquoted. Serum iron and unsaturated iron binding capacity (UIBC) were determined with the use of a Cobas 6000 (Roche) blood chemistry analyzer. Transferrin saturation was calculated as the percentage of total iron binding capacity to total serum iron levels.

Example 9: Effect of Form a on Iron-Refractory Iron Deficiency Anemia

The effect of Form A in iron-refractory iron deficiency anemia (IRIDA) is determined using a mouse model of IRIDA. Briefly, eight-week old C57BL/6 mice are dosed intravenously every 3 days with a lipid encapsulated siRNA targeted against either Luciferase (control) or TMPRSS6 (0.75 mg/kg). Mice receive siRNA treatment until the point that the cohort receiving TMPRSS6 siRNA has increased hepcidin and decreased serum hemoglobin and serum iron. At this point, mice are further randomized to receive either vehicle or Form A. Mice are euthanized at 12 d after their first siRNA administration. Whole blood is collected and assayed for hematological parameters. Additionally, serum is collected and assayed for hepcidin concentration by ELISA and total iron content by colorimetric assay.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. An anhydrous crystalline compound having the structure of Formula (I),

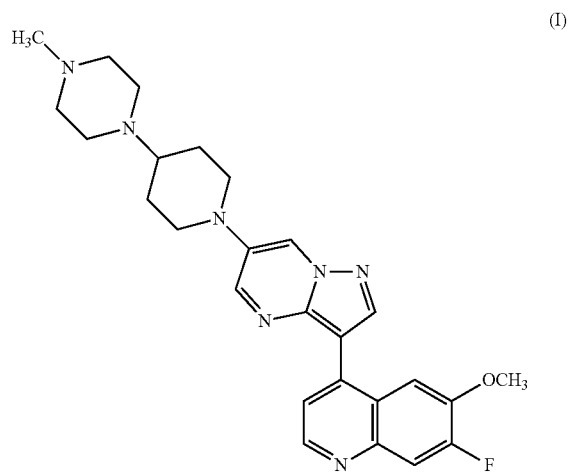 [SMILES: COc1cc2c(-c3cnn4cc(N5CCC(N6CCN(C)CC6)CC5)cnc34)ccnc2cc1F]

mono-succinate salt.

2. The anhydrous crystalline compound of claim 1, having 2θ values of about 7.05±0.2, 15.16±0.2, 21.05±0.2, 21.26±0.2, and 24.47±0.2.

3. The anhydrous crystalline compound of claim 2, having 2θ values of about 3.58±0.2, 7.05±0.2, 13.8±0.2, 14.16±0.2, 15.16±0.2, 16.18±0.2, 16.80±0.2, 17.15±0.2, 17.69±0.2, 18.29±0.2, 18.84±0.2, 20.29±0.2, 21.05±0.2, 21.26±0.2, 22.68±0.2, 23.84±0.2, 24.47±0.2, 24.84±0.2, and 28.47±0.2.

4. The anhydrous crystalline compound of claim 3, having 2θ values of about 3.58±0.2, 7.05±0.2, 10.59±0.2, 10.75±0.2, 13.80±0.2, 14.16±0.2, 15.16±0.2, 15.68±0.2, 16.18±0.2, 16.80±0.2, 17.15±0.2, 17.69±0.2, 17.97±0.2, 18.29±0.2, 18.59±0.2, 18.84±0.2, 19.27±0.2, 20.29±0.2, 21.05±0.2, 21.26±0.2, 21.56±0.2, 21.78±0.2, 22.68±0.2, 23.84±0.2, 24.47±0.2, 24.84±0.2, 25.15±0.2, 26.10±0.2, 27.12±0.2, 27.78±0.2, 28.47±0.2, and 29.06±0.2.

5. The anhydrous crystalline compound of claim 1, having an XRPD pattern substantially as shown in FIG. 1, labeled Form A.

6. The anhydrous crystalline compound of claim 1, having 2θ values of about 9.79±0.2, 13.05±0.2, 22.91±0.2, 23.60±0.2, and 26.25±0.2.

7. The anhydrous crystalline compound of claim 6, having 2θ values of about 3.25±0.2, 9.79±0.2, 13.05±0.2, 16.75±0.2, 19.50±0.2, 22.91±0.2, 23.60±0.2, and 26.25±0.2.

8. The anhydrous crystalline compound of claim 7, having 2θ values of about 3.25±0.2, 9.79±0.2, 13.05±0.2, 13.61±0.2, 14.39±0.2, 16.75±0.2, 18.50±0.2, 19.50±0.2, 22.91±0.2, 23.60±0.2, and 26.25±0.2.

9. The anhydrous crystalline compound of claim 1, having an XRPD pattern substantially as shown in FIG. 2, labeled Form B.

10. A method for preparing an anhydrous crystalline compound having the structure of Formula (I):

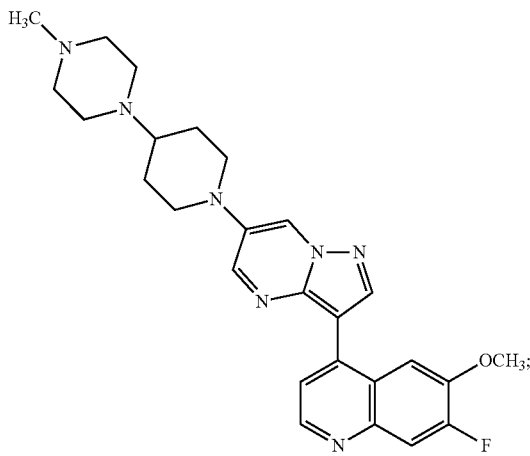

comprising:
   a) providing a compound of Formula (I);
   b) adding a succinic acid to form a mixture; and
   c) crystallizing the compound of Formula (I) from the mixture comprising the compound of Formula (I),
   wherein the anhydrous crystalline compound is a mono-succinate salt.

11. A method of treating a subject having anemia, comprising administering to the subject a therapeutically effective amount of the anhydrous crystalline compound of claim 1.

12. A method of treating abnormal bone formation in a soft tissue of a subject, comprising administering to the subject a therapeutically effective amount of the anhydrous crystalline compound of claim 1.

13. The method of claim 12, wherein the subject is determined to
   a) have or be at risk of having abnormal bone formation prior to treatment; and/or
   b) have been subjected to a musculoskeletal trauma, a spinal cord injury or a central nervous system injury.

14. The method of claim 13, wherein the abnormal bone formation is associated with a heterotopic ossification disease.

15. A method of treating a subject having hypercholesterolemia, hyperlipidemia, or hyperlipoproteinemia, comprising administering to the subject a therapeutically effective amount of the anhydrous crystalline compound of claim 1.

16. A method of treating a subject having a disease, disorder, or syndrome caused by hyperlipidemia, comprising administering to the subject a therapeutically effective amount of the anhydrous crystalline compound of claim 1.

17. A method of treating a subject having atherosclerosis, comprising administering to the subject a therapeutically effective amount of the anhydrous crystalline compound of claim 1.

* * * * *